US012690774B2

(12) United States Patent
Cabral et al.

(10) Patent No.: US 12,690,774 B2
(45) Date of Patent: Jul. 28, 2026

(54) TECHNIQUES FOR USING INWARD-FACING EYE-TRACKING CAMERAS OF A HEAD-WORN DEVICE TO MEASURE HEART RATE, AND SYSTEMS AND METHODS USING THOSE TECHNIQUES

(71) Applicant: Meta Platforms Technologies, LLC, Menlo Park, CA (US)

(72) Inventors: Brian Keith Cabral, San Jose, CA (US); Michael John Toksvig, Palo Alto, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 227 days.

(21) Appl. No.: 18/495,388

(22) Filed: Oct. 26, 2023

(65) Prior Publication Data

US 2024/0252050 A1 Aug. 1, 2024

Related U.S. Application Data

(60) Provisional application No. 63/482,014, filed on Jan. 27, 2023.

(51) Int. Cl.
| | |
|---|---|
| *A61B 5/024* | (2006.01) |
| *A61B 5/16* | (2006.01) |
| *G02B 27/01* | (2006.01) |
| *G06F 3/01* | (2006.01) |
| *G06V 10/141* | (2022.01) |
| *G06V 10/56* | (2022.01) |

(52) U.S. Cl.
CPC .............. *A61B 5/024* (2013.01); *A61B 5/163* (2017.08); *G02B 27/0172* (2013.01); *G06F 3/013* (2013.01); *G06V 10/141* (2022.01); *G06V 10/56* (2022.01)

(58) Field of Classification Search
None
See application file for complete search history.

(56) References Cited

U.S. PATENT DOCUMENTS

| | | | | |
|---|---|---|---|---|
| 8,928,585 B2 * | 1/2015 | Mondragon | ........... | G06V 40/20 |
| | | | | 345/156 |
| 10,405,808 B2 * | 9/2019 | Draeger | ............... | A61B 5/0205 |

(Continued)

OTHER PUBLICATIONS

European Search Report for European Patent Application No. 24151982.6, dated Jun. 24, 2024, 7 pages.

(Continued)

*Primary Examiner* — Benjamin J Klein
(74) *Attorney, Agent, or Firm* — Morgan, Lewis & Bockius LLP

(57) ABSTRACT

The various implementations described herein include methods and systems for monitoring biometric information. In one aspect, a method includes (i) capturing, via an inward-facing camera of an artificial-reality headset, a plurality of images of a region of a face of the user, the region including an eye of the user, where (a) a first image of the plurality of images includes a first position of a pupil in the eye, and (b) a second image of the plurality of images includes a second position of the pupil in the eye, the second position different than the first position; and (ii) determining heart rate information based on the plurality of images.

20 Claims, 25 Drawing Sheets

(56) References Cited

U.S. PATENT DOCUMENTS

| | | | |
|---|---|---|---|
| 10,806,356 B2 * | 10/2020 | Lee ....................... | A61B 5/0077 |
| 12,019,808 B2 * | 6/2024 | Winters, IV ........... | G06V 40/20 |
| 12,373,040 B2 * | 7/2025 | Winters, IV ........... | G06V 20/20 |
| 2003/0009106 A1 | 1/2003 | Sitzman et al. | |
| 2015/0003819 A1 * | 1/2015 | Ackerman ............. | G03B 13/36 |
| | | | 396/51 |
| 2017/0371408 A1 | 12/2017 | Wilson | |
| 2018/0055392 A1 | 3/2018 | Lee et al. | |
| 2022/0155860 A1 * | 5/2022 | Tzvieli ..................... | G06F 3/013 |
| 2022/0378310 A1 | 12/2022 | Foster et al. | |
| 2025/0166399 A1 * | 5/2025 | Lee ....................... | G06V 10/774 |

OTHER PUBLICATIONS

Wang C., et al., "Arousal Effects on Pupil Size, Heart Rate, and Skin Conductance in an Emotional Face Task," Frontiers in Neurology, Dec. 3, 2018, vol. 9, No. 1029, pp. 1-13.
Office Action mailed Feb. 16, 2026 for European Patent Application No. 24151982.6, filed on Jan. 15, 2024, 6 pages.
Parnandi A., et al., "Contactless Measurement of Heart Rate Variability from Pupillary Fluctuations," 2013 Humaine Association Conference on Affective Computing and Intelligent Interaction, Sep. 2, 2013, XP032530366, pp. 191-196.

* cited by examiner

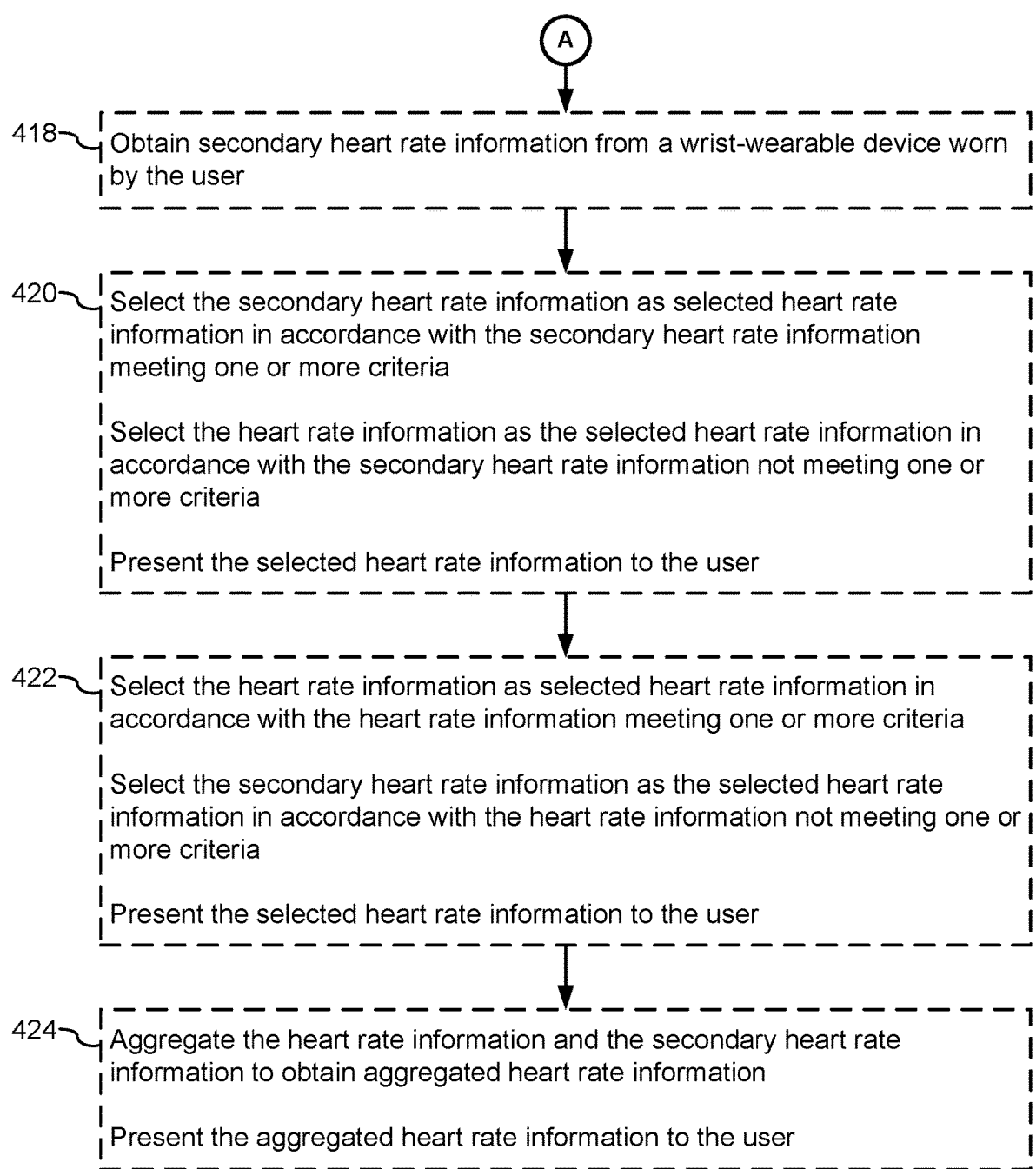

418⟶ Obtain secondary heart rate information from a wrist-wearable device worn by the user 420⟶ Select the secondary heart rate information as selected heart rate information in accordance with the secondary heart rate information meeting one or more criteria Select the heart rate information as the selected heart rate information in accordance with the secondary heart rate information not meeting one or more criteria Present the selected heart rate information to the user 422⟶ Select the heart rate information as selected heart rate information in accordance with the heart rate information meeting one or more criteria Select the secondary heart rate information as the selected heart rate information in accordance with the heart rate information not meeting one or more criteria Present the selected heart rate information to the user 424⟶ Aggregate the heart rate information and the secondary heart rate information to obtain aggregated heart rate information Present the aggregated heart rate information to the user

Figure 4B

AR system 500b

AR system 500c 502          700

800

600

524          520

522

AR system 500c

520

+500

VR device 710

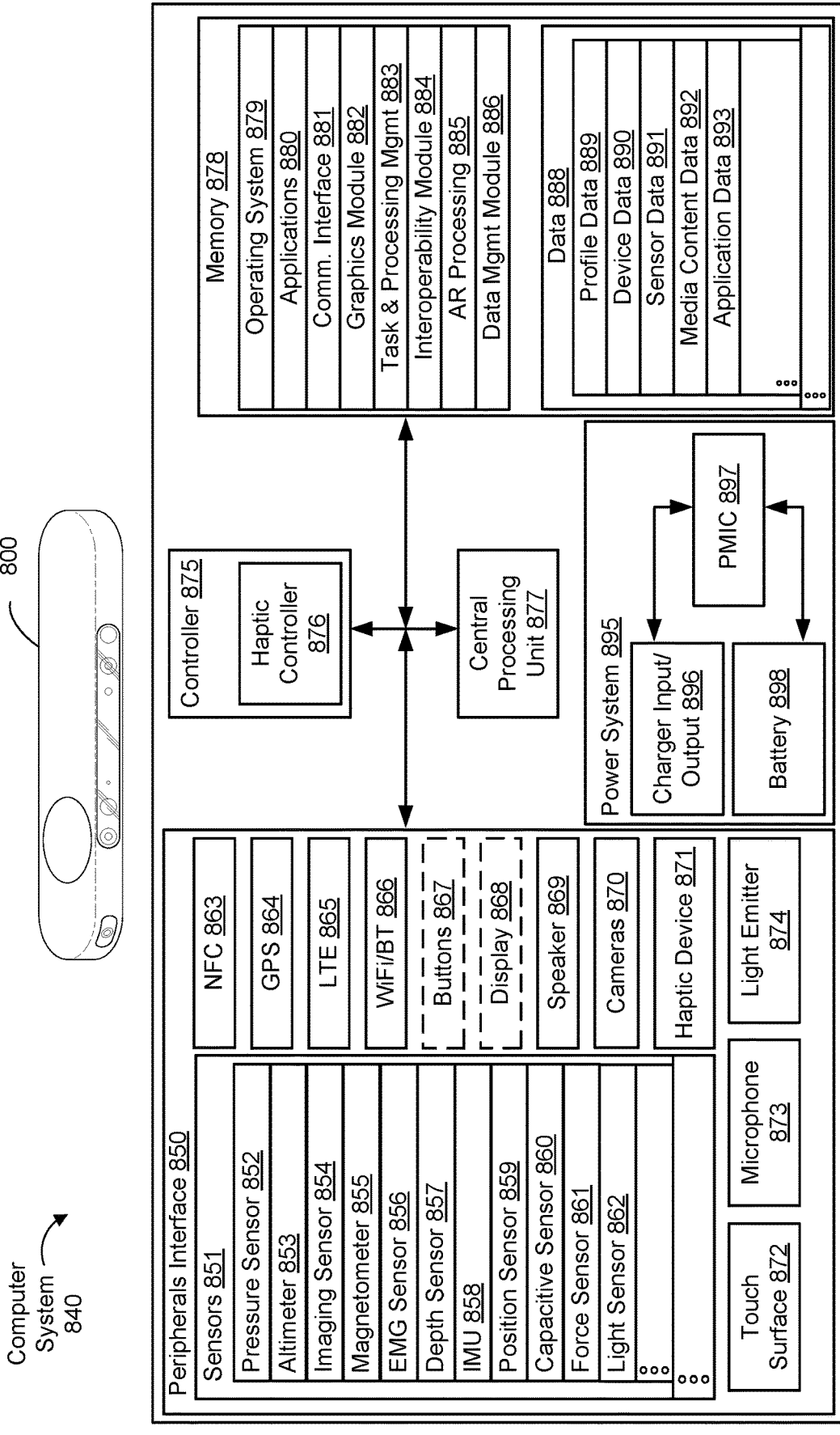

Computer System 800

Computer System 840

Peripherals Interface 850

Sensors 851

Pressure Sensor 852

Altimeter 853

Imaging Sensor 854

Magnetometer 855

EMG Sensor 856

Depth Sensor 857

IMU 858

Position Sensor 859

Capacitive Sensor 860

Force Sensor 861

Light Sensor 862

NFC 863

GPS 864

LTE 865

WiFi/BT 866

Buttons 867

Display 868

Speaker 869

Cameras 870

Haptic Device 871

Light Emitter 874

Touch Surface 872

Microphone 873

Controller 875

Haptic Controller 876

Central Processing Unit 877

Power System 895

Charger Input/Output 896

PMIC 897

Battery 898

Memory 878

Operating System 879

Applications 880

Comm. Interface 881

Graphics Module 882

Task & Processing Mgmt 883

Interoperability Module 884

AR Processing 885

Data Mgmt Module 886

Data 888

Profile Data 889

Device Data 890

Sensor Data 891

Media Content Data 892

Application Data 893

Figure 8B

TECHNIQUES FOR USING INWARD-FACING EYE-TRACKING CAMERAS OF A HEAD-WORN DEVICE TO MEASURE HEART RATE, AND SYSTEMS AND METHODS USING THOSE TECHNIQUES

RELATED APPLICATIONS

This application claims priority to U.S. Prov. App. No. 63/482,014, filed on Jan. 27, 2023 and titled "Techniques for Using Inward-Facing Eye-Tracking Cameras of a Head-Worn Device to Measure Heart Rate, and Systems and Methods Using Those Techniques," which is incorporated herein by reference.

TECHNICAL FIELD

The present disclosure relates generally to devices and methods for eye tracking and biometric monitoring and reporting, including but not limited to devices and methods for using eye-tracking cameras of a head-wearable device to determine a heart rate of a user.

BACKGROUND

A photoplethysmogram (PPG) can be used to detect blood volume changes, e.g., in a microvascular bed of tissue. A PPG can be obtained using an oximeter (e.g., an optical sensor and a light source) that illuminates the skin and measures changes in light absorption. For example, an oximeter can monitor the perfusion of blood to the dermis and subcutaneous tissue of the skin. However, an accurate PPG requires consecutive measurements from a same region of the user to accurately monitor blood perfusion. For that reason, conventional PPG systems may require a user to remain motionless and/or focus on a particular point during the PPG measurement.

SUMMARY

The present disclosure describes systems and methods for using a head-wearable device (e.g., an artificial-reality headset) to obtain a PPG and/or monitor biometrics, such as heart rate, while a user is in motion (e.g., interacting with a user interface of the head-wearable device). Some of the head-wearable devices described herein include one or more inward-facing cameras configured to track a user's eye. As described herein, the inward-facing camera(s) can also be used to monitor blood volume changes in a user's eye and/or facial tissue.

As an example, a user wearing a virtual-reality headset may wish to monitor their heart rate while engaging in a virtual-reality activity such as playing a video game or performing an exercise or fitness routine. In this example, the virtual-reality headset includes one or more inward-facing cameras, e.g., configured to track a wearer's eyes. As described herein, the inward-facing cameras of the virtual-reality headset can be used to monitor blood volume changes in the user's eye or facial tissue while the user engages in the virtual-reality activity. The blood volume changes can be used to obtain a PPG for the user and the PPG can be used to determine a heart rate of the user. In this way the user can monitor their heart rate while engaging in the virtual-reality activity (e.g., without having to remain stationary and/or focus on a fixed point). Having the inward-facing camera(s) as a component of the head-wearable device allows the camera(s) to maintain a fixed position relative to the user's face while the user is moving and interacting with user interfaces and virtual-reality objects. In this way, consecutive measurements of a region of the user's face can be obtained and compared to generate a PPG.

In accordance with some embodiments, a method is provided for monitoring a heart rate of a user. The method includes capturing, via an inward-facing camera of an artificial-reality headset, a plurality of images of a region of a face of the user, the region including an eye of the user. A first image of the plurality of images includes a first position of a pupil in the eye and a second image of the plurality of images includes a second position of the pupil in the eye, the second position different than the first position. The method further includes determining heart rate information based on the plurality of images.

In some embodiments, a computing device (e.g., a wrist-wearable device or a head-mounted device, or an intermediary device such as a smartphone or desktop or laptop computer) includes one or more processors, memory, a display (in some embodiments, the display can be optional, such as for certain example intermediary devices that can coordinate operations at the wrist-wearable device and the head-mounted device, and thus have ample processing and power resources but need not have its own display), and one or more programs stored in the memory. The programs are configured for execution by the one or more processors. The one or more programs include instructions for performing (or causing performance of) any of the methods described herein.

In some embodiments, a non-transitory computer-readable storage medium stores one or more programs configured for execution by a computing device (e.g., a wearable device, or an intermediary device such as a smartphone or desktop or laptop computer that can be configured to coordinate operations at the wrist-wearable device and the head-mounted device) having one or more processors and memory. The one or more programs include instructions for performing (or causing performance of) any of the methods described herein.

Thus, methods, systems, and computer-readable storage media are disclosed for eye tracking and biometric monitoring and reporting. Such methods and systems may complement or replace conventional methods for eye tracking and biometric monitoring and reporting.

The features and advantages described in the specification are not necessarily all inclusive and, in particular, some additional features and advantages will be apparent to one of ordinary skill in the art in view of the drawings, specification, and claims provided in this disclosure. Moreover, it should be noted that the language used in the specification has been principally selected for readability and instructional purposes and has not necessarily been selected to delineate or circumscribe the subject matter described herein.

BRIEF DESCRIPTION OF THE DRAWINGS

So that the present disclosure can be understood in greater detail, a more particular description can be had by reference to the features of various embodiments, some of which are illustrated in the appended drawings. The appended drawings, however, merely illustrate pertinent features of the present disclosure and are therefore not meant to necessarily be considered limiting, for the description can admit to other effective features as the person of skill in this art will appreciate upon reading this disclosure.

FIGS. 4A-4B are a flow diagram illustrating an example method for monitoring heart rate in accordance with some embodiments.

FIGS. 7A, 7B-1, 7B-2, and 7C illustrate example head-wearable devices in accordance with some embodiments.

FIGS. 8A-8B illustrate an example handheld intermediary processing device in accordance with some embodiments.

In accordance with common practice, the various features illustrated in the drawings are not necessarily drawn to scale, and like reference numerals can be used to denote like features throughout the specification and figures.

DETAILED DESCRIPTION

As an example, a user wearing a virtual-reality headset can monitor their heart rate and/or other biometric data using an inward-facing camera of the virtual-reality headset. The virtual-reality headset can be used to monitor blood volume levels in a user's eye and/or facial tissue to obtain PPG information for the user. The heart rate and other biometric data can be obtained from the PPG information and provided to the user. PPG measurements can also be used to determine oxygen saturation (pulse oximetry), respiration rate, blood pressure, and cardiac output. PPG measurements can also be used to assess autonomic functions and detect of peripheral vascular diseases. For example, a user interface presented by the virtual-reality headset can include presentation of the heart rate and/or other biometric data. As a further example, secondary biometric data can be obtained from another wearable device, such as a wrist-wearable device, and combined with the biometric data from the virtual-reality headset.

Figure 1A:
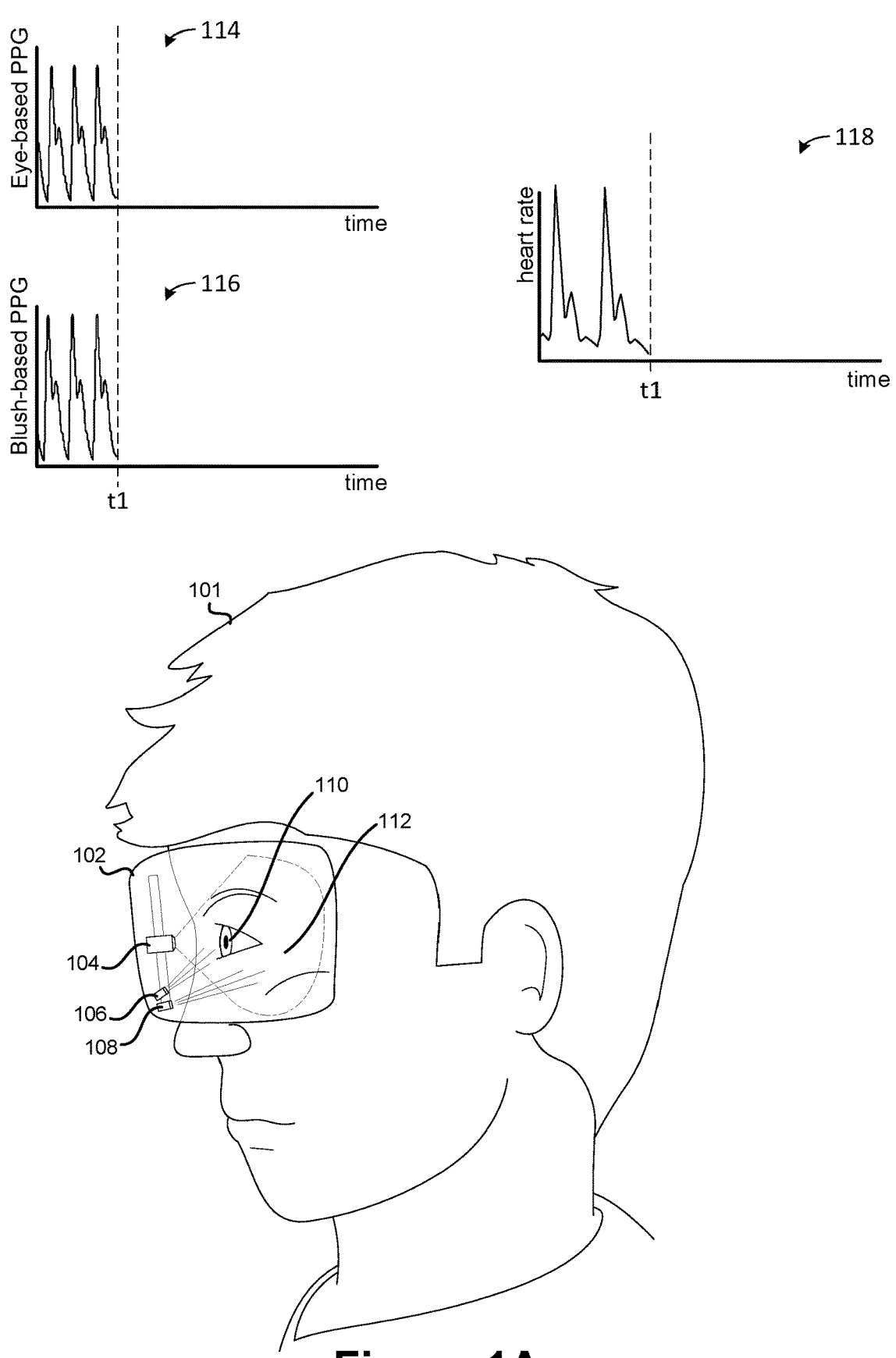
FIGS. 1A-1C illustrate an example of monitoring biometric data via a head-wearable device in accordance with some embodiments.
Figure 1B:
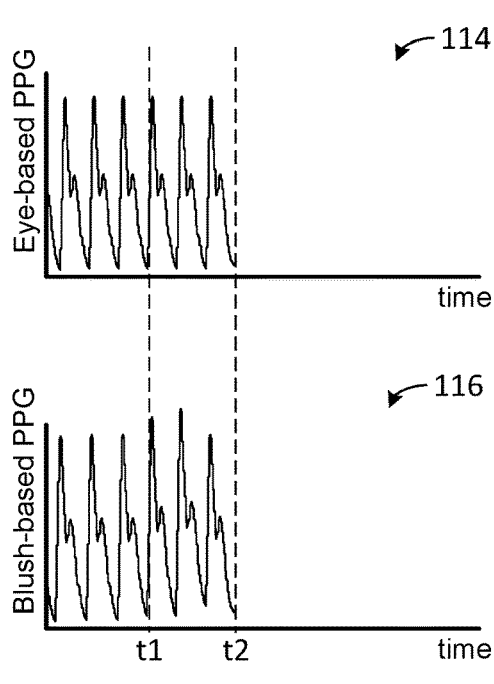
Figure 1B:
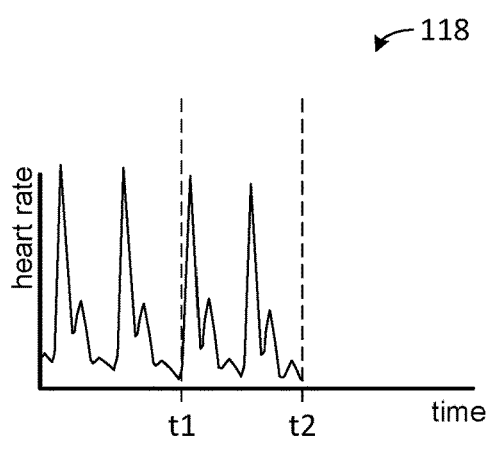
Figure 1B:
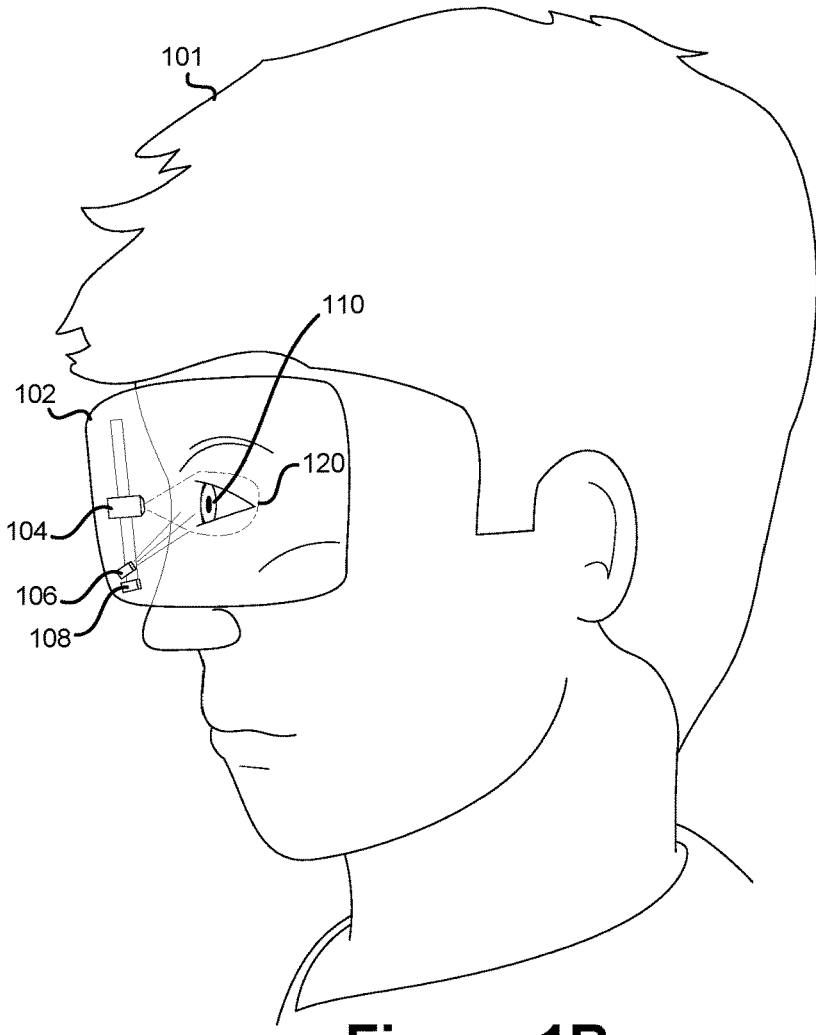
Figure 1C:
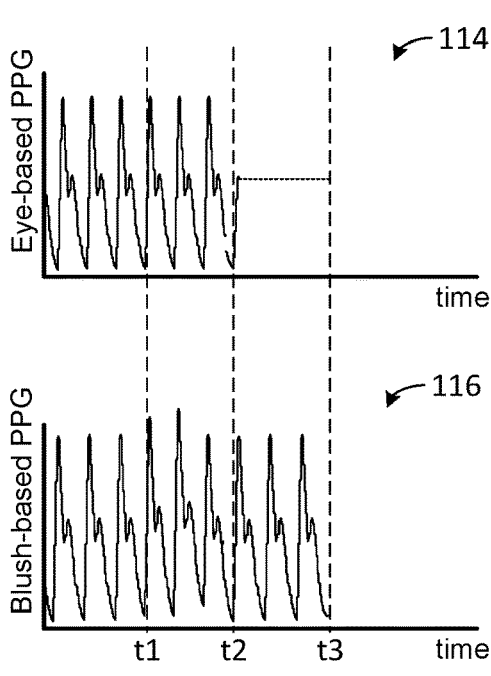
Figure 1C:
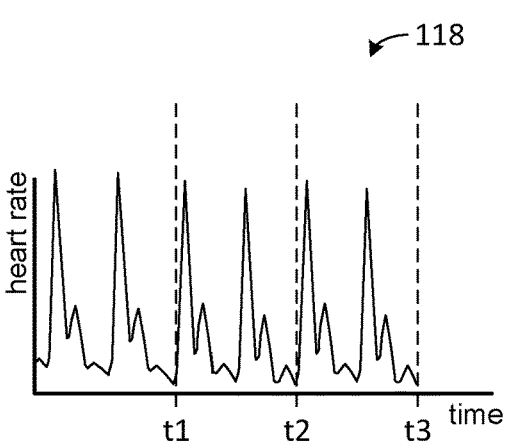
Figure 1C:
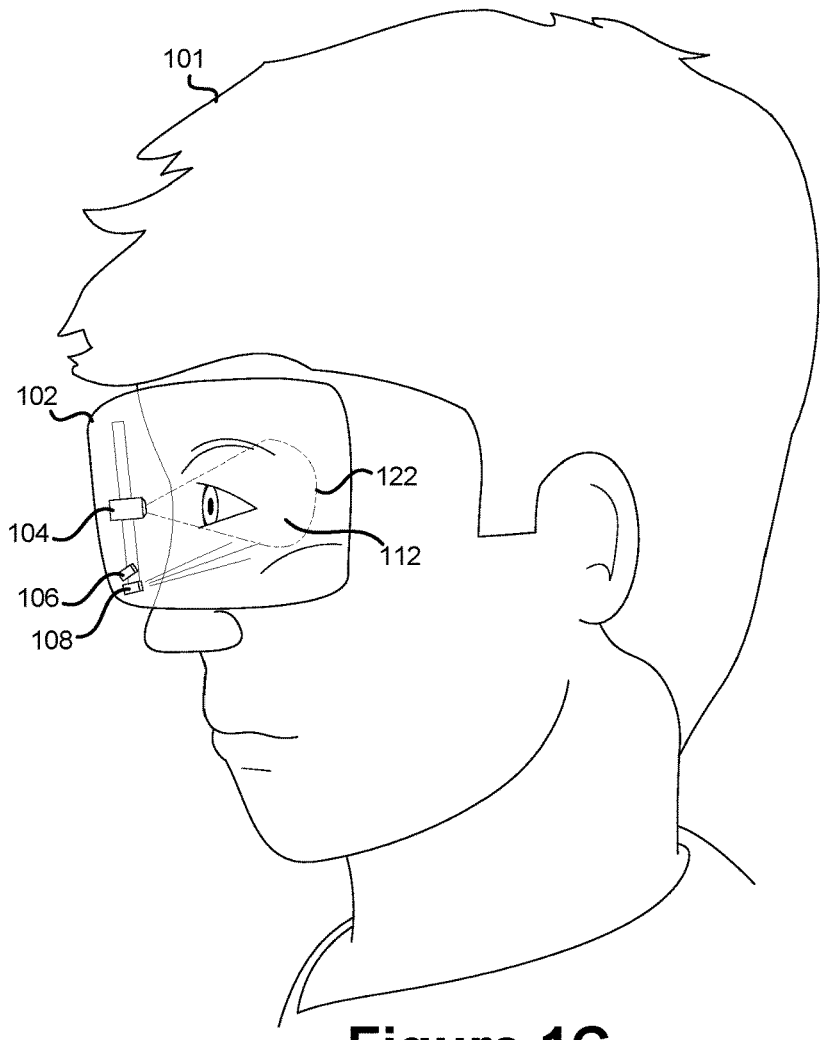

Turning now to the figures. FIGS. 1A-1C illustrate an example of monitoring biometric data via a head-wearable device in accordance with some embodiments. FIG. 1A illustrates a user 101 wearing a head-wearable device 102 at a first time, t1, in accordance with some embodiments. In some embodiments, the head-wearable device 102 is an artificial-reality headset (e.g., a virtual-reality headset). The head-wearable device 102 includes an inward-facing camera 104 (e.g., a camera configured to sense infrared and/or near-infrared wavelengths) positioned to capture images of an eye 110 of the user 101 and facial tissue 112 of the user 101. In accordance with some embodiments, the head-wearable device 102 includes an illumination source 106 positioned to illuminate the eye 110 of the user 101 and an illumination source 108 positioned to illuminate the facial tissue 112 of the user 101. In some embodiments, the illumination source 106 and/or the illumination source 108 is configured to emit infrared and/or near-infrared light. FIG. 1 also shows eye-based PPG information 114 measured based on eye movement and/or blood flow in the user's eye 110 and blush-based PPG information 116 measured based on blood volume levels in the user's facial tissue 112. FIG. 1 further shows heart rate information 118 determined based on the eye-based PPG information 114 and/or the blush-based PPG information 116.

FIG. 1B illustrates the user 101 wearing the head-wearable device 102 at a second time, t2, that is subsequent to the first time in accordance with some embodiments. FIG. 1B further shows the blush-based PPG information 116 having increased noise during the time between t1 and t2 as compared to the eye-based PPG information 114. In some embodiments, the heart rate information 118 between t1 and t2 is based on the eye-based PPG information 114 because it has less noise compared to the blush-based PPG information 116 for that period. In some cases, the additional noise is due to movement of the user relative to the camera and/or changes in lighting levels between the camera and the user. In some cases, the additional noise is due to the camera being focused on the eye 110 of the user. In some embodiments, the camera 104 focuses on the eye 110 in accordance with a determination that the blush-based PPG information is noisier, as indicated by the focus region 120.

FIG. 1C illustrates the user 101 wearing the head-wearable device 102 at a third time, t3, that is subsequent to the second time in accordance with some embodiments. FIG. 1C further shows the eye-based PPG information 114 having no data during the time between t2 and t3. In some embodiments, the heart rate information 118 between t2 and t3 is based on the blush-based PPG information 116 because the eye-based PPG information 114 is unavailable for that period. In some cases, the eye-based PPG information 114 is unavailable because the camera's view of the eye 110 is obstructed (e.g., due to the user closing their eye). In some cases, the eye-based PPG information 114 is unavailable due to movement of the eye relative to the camera and/or changing in lighting levels between the camera and the eye 110 of the user. In some embodiments, the camera 104 focuses on the facial tissue 112 in accordance with a determination that the eye-based PPG information is unavailable, as indicated by the focus region 122.

Figure 2A:
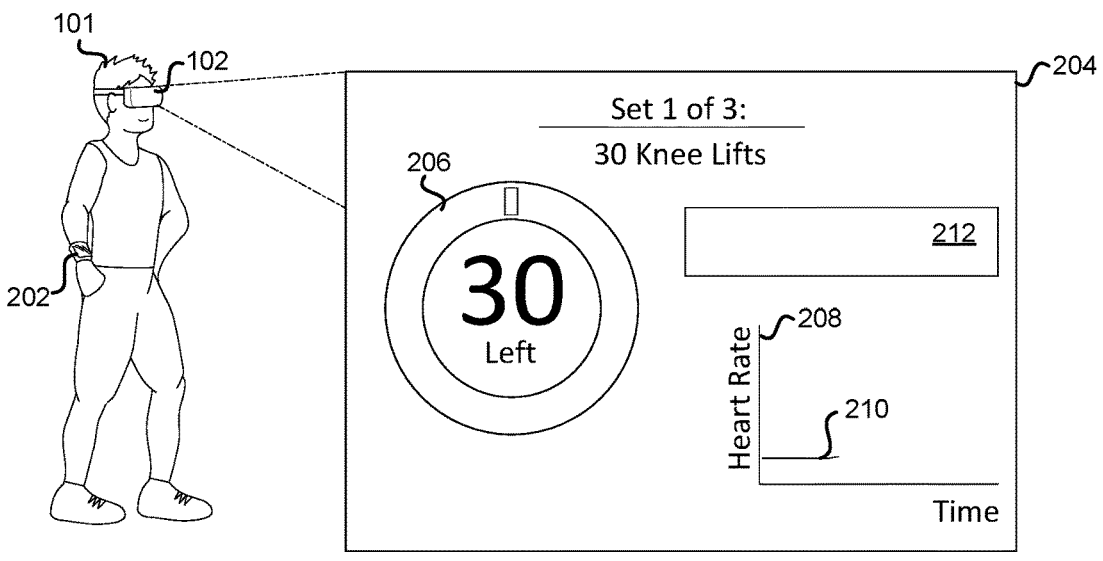
FIGS. 2A-2C illustrate an example user scenario of monitoring biometric data via a head-wearable device in accordance with some embodiments.
Figure 2B:
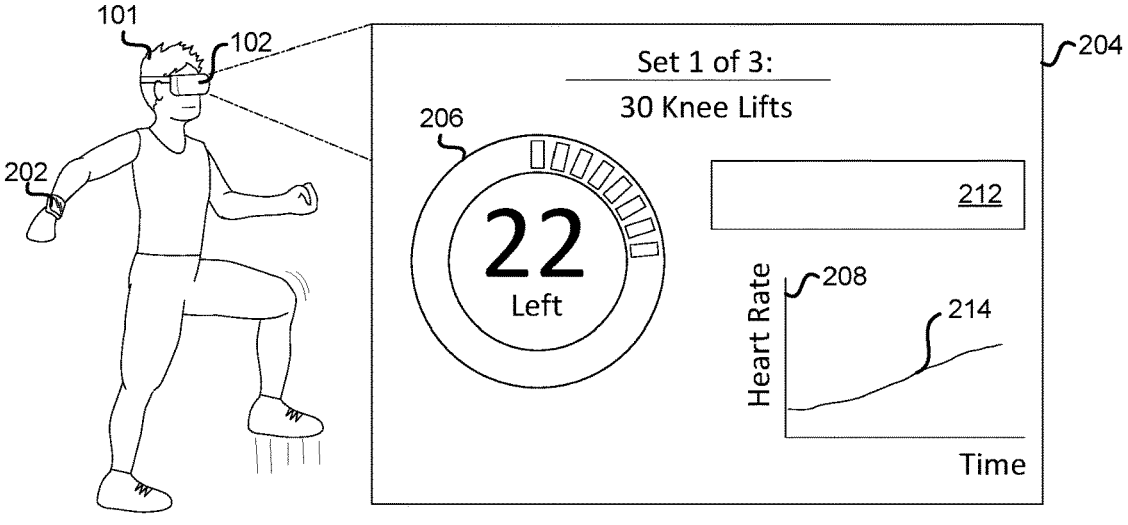
Figure 2C:
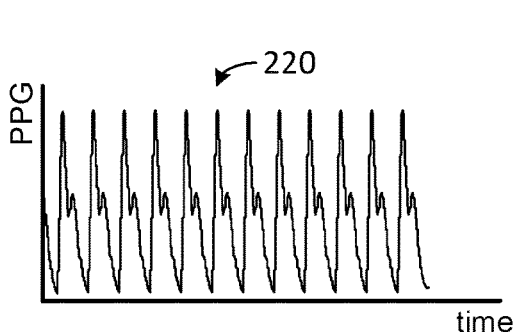
Figure 2C:
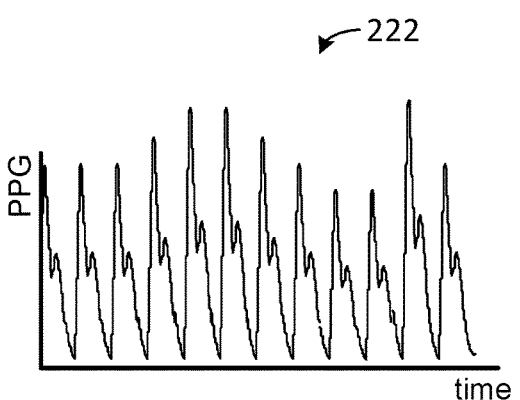
Figure 2C:
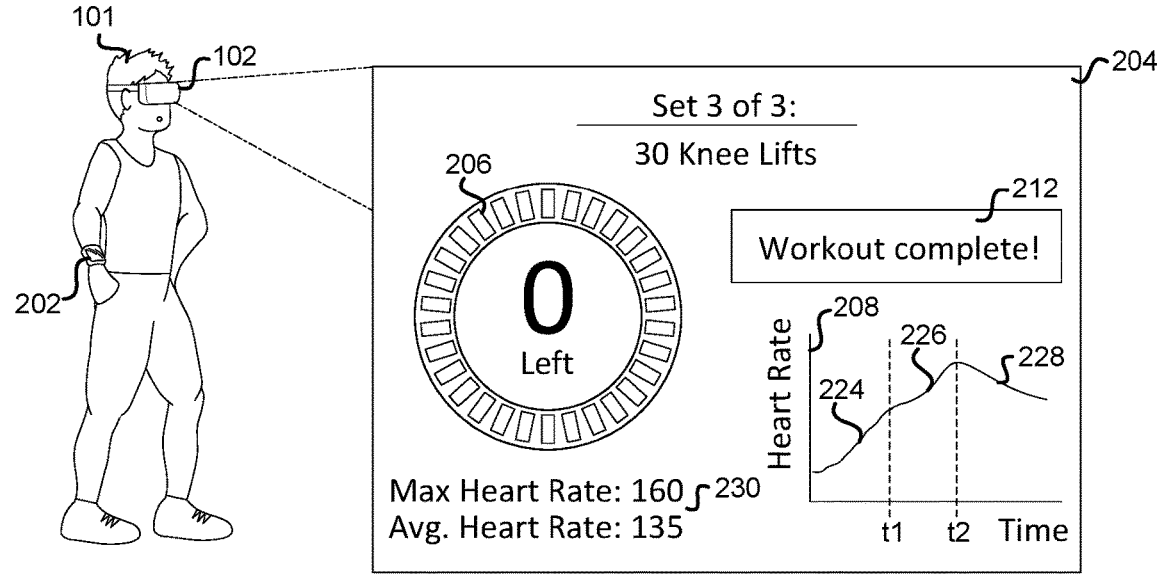

FIGS. 2A-2C illustrate an example user scenario of monitoring biometric data via the head-wearable device 102 in accordance with some embodiments. FIG. 2A shows the user 101 wearing the head-wearable device 102 and a wrist-wearable device 202. FIG. 2A further shows a user interface 204 (e.g., a fitness application user interface) presented to the user 101 via the head-wearable device 102. The user interface 204 includes an exercise counter 206, a message element 212, and a heart rate graph 208 with heart rate information 210 for the user 101. In some embodiments, the heart rate information 210 is determined based on PPG measurements from the head-wearable device 102 (e.g., the eye-based PPG information 114 and/or the blush-based PPG information 116) and/or the wrist-wearable device 202.

FIG. 2B shows the user 101 performing the exercise (knee lifts) and the user interface 204 updating accordingly. The user interface 204 in FIG. 2B shows the exercise counter 206 updating to indicate that the user has performed eight of 30 knee lifts for a first set of knee lifts. The user interface 204 in FIG. 2B further shows the heart rate graph 208 updating with additional heart rate information 214. In some embodiments, the additional heart rate information 214 is determined based on PPG measurements from the head-wearable device 102 (e.g., the eye-based PPG information 114 and/or blush-based PPG information 116) and/or the wrist-wearable device 202.

FIG. 2C shows the user 101 having completed the exercise and the user interface 204 updating accordingly. The user interface 204 in FIG. 2C shows a message ("Workout complete!") in the message element 212. The exercise counter 206 in FIG. 2C shows that the user 101 has completed the set and the heart rate graph 208 shows the user's heart rate during the course of the exercise. The user interface 204 in FIG. 2C also shows heart rate information 230 indicating the user's average and maximum heart rates (e.g., during the sets). In some embodiments, a portion of the heart rate information is based on PPG measurements from the head-wearable device 102 and a portion of the heart rate information is based on PPG measurements from the wrist-wearable device 202. For example, heart rate information 224 may be based on PPG measurements (e.g., PPG 220) from the head-wearable device 102, heart rate information 226 may be based on PPG measurements (e.g., PPG 222) from the wrist-wearable device 202, and heart rate information 228 may be based on PPG measurements from the head-wearable device 102. In some embodiments, the heart rate information is based on the PPG data determined to be most stable (e.g., having the least amount of noise).

Figure 3A:
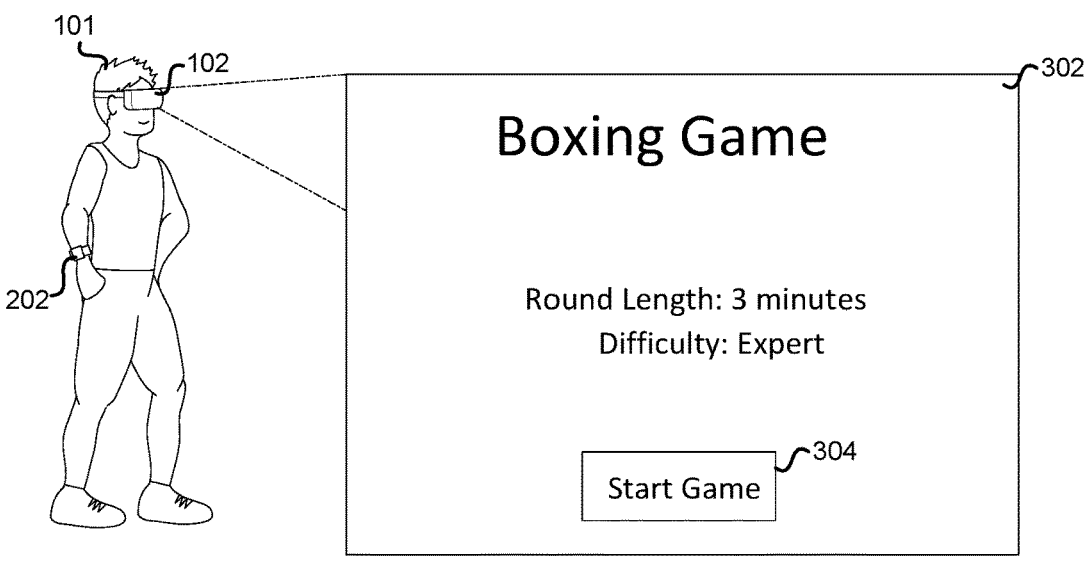
FIGS. 3A-3D illustrate another example user scenario of monitoring biometric data via a head-wearable device in accordance with some embodiments.

FIGS. 3A-3D illustrate another example user scenario of monitoring biometric data via the head-wearable device 102 in accordance with some embodiments. FIG. 3A shows the user 101 wearing the head-wearable device 102 and a wrist-wearable device 202. FIG. 3A further shows a user interface 302 (e.g., a boxing game user interface) presented to the user 101 via the head-wearable device 102. The user interface 302 includes information about the boxing game and a virtual button 304 to start playing the game.

Figure 3B:
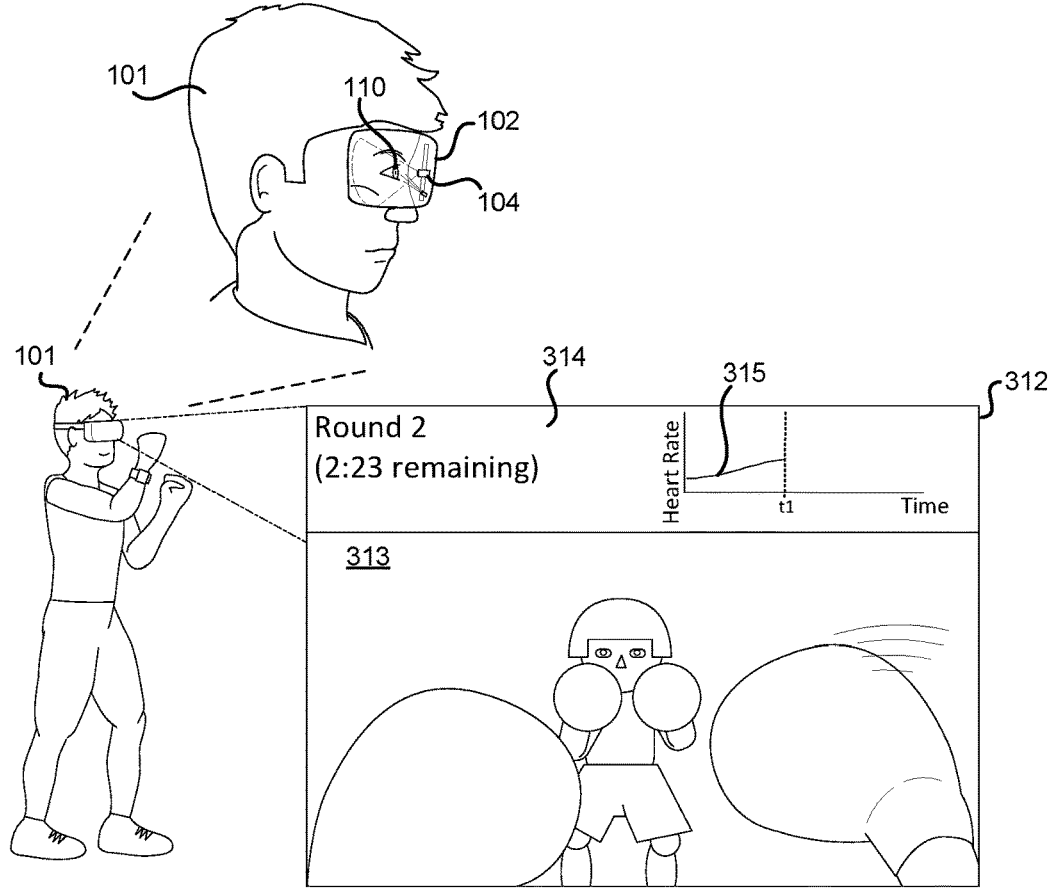

FIG. 3B shows the user 101 playing the boxing game at a first time (t1) as indicated by the user interface 312. The user interface 302 includes a boxing portion 313 showing the boxing gameplay and an information portion 314 that includes information about the time remaining in the round and heart rate information 315. In some embodiments, the heart rate information 315 is obtained from PPG measurements obtained via the head-wearable device 102. In some embodiments, the PPG measurements are obtained via the camera 104 from blood flow in the user's eye 110.

Figure 3C:
Figure 3C:
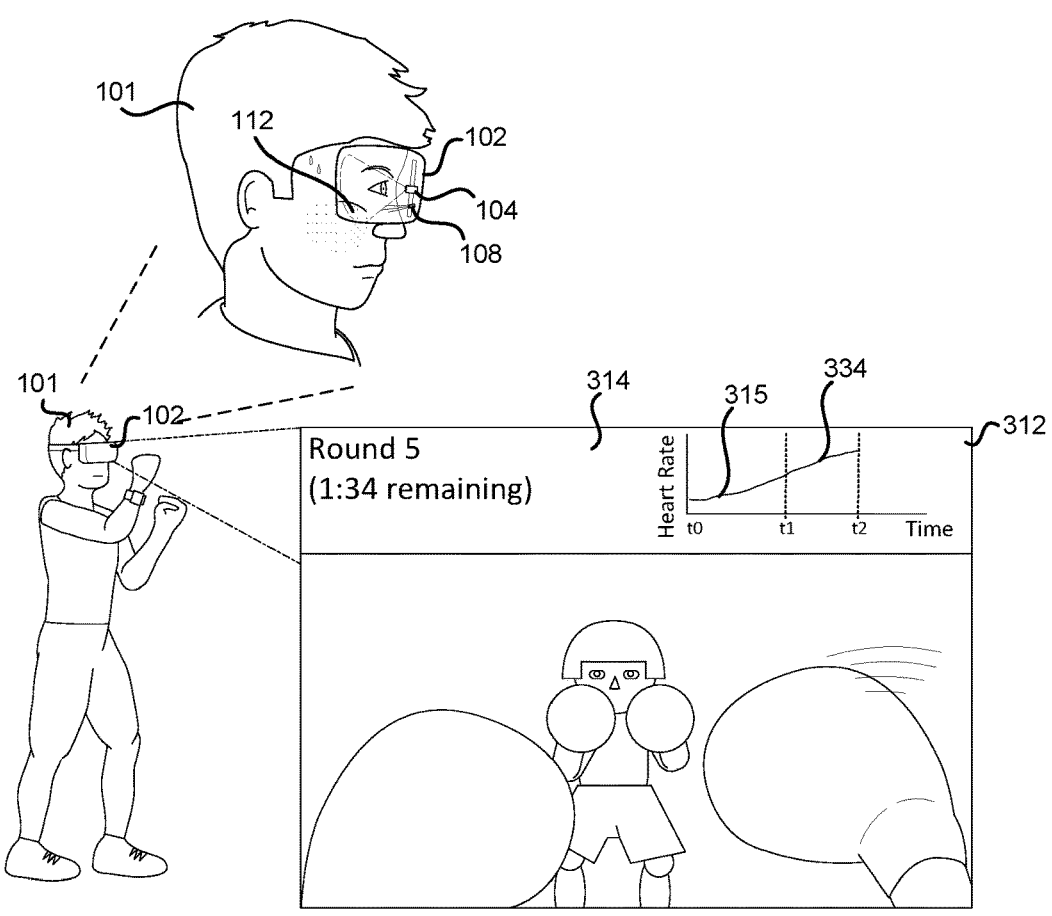

FIG. 3C shows the user 101 playing the boxing game at a second time, subsequent to the first time (t2), as indicated by the user interface 312. The information portion 314 in FIG. 3C is updated to include heart rate information 334 as well as heart rate information 315. In some embodiments, the heart rate information 334 is obtained from PPG measurements obtained via the head-wearable device 102. In some embodiments, the PPG measurements are obtained via the camera 104 from blood volume level changes in facial tissue 112 of the user (e.g., blush levels). In some embodiments, the facial tissue 112 is illuminated by the illumination source 108 (e.g., to assist the camera 104 in detecting blood volume levels). As illustrated in FIGS. 3B and 3C, the PPG measurements can be obtained from eye and/or facial tissue blood volume levels. For example, the head-wearable device 102 can obtain measurements from both the eye 110 and the facial tissue 112 and select the measurement with the least noise/variation to use to determine the user's heart rate information (e.g., select a PPG measurement source for a given period, such as 1 second, 10 seconds, 30 seconds, or 1 minute).

Figure 3D:
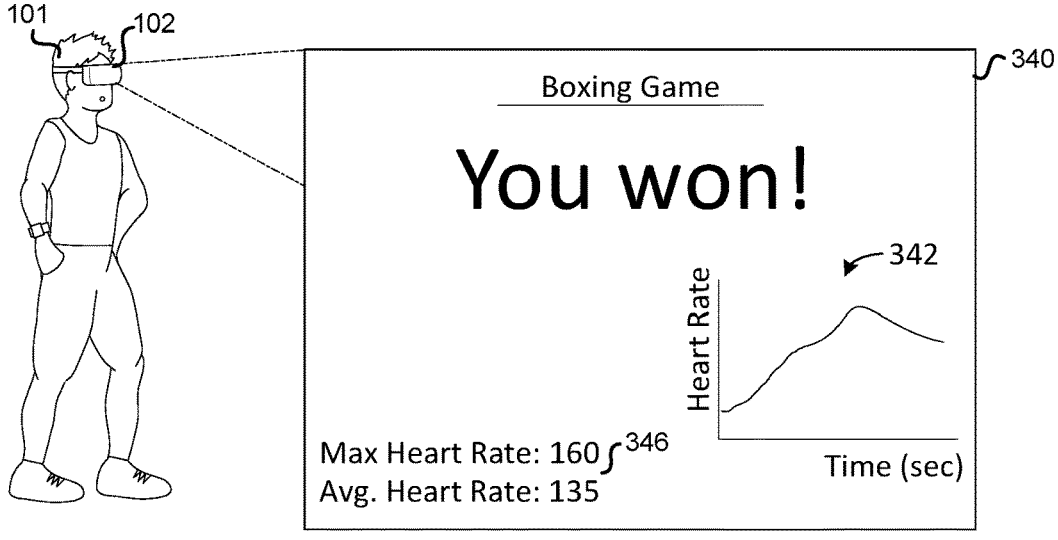

FIG. 3D shows the user 101 having completed the boxing game as indicated by the user interface 340. In accordance with some embodiments, the user interface 340 includes a heart rate graph 342 indicating the user's heart rate during the boxing match and heart rate information 346 indicating a maximum heart rate and average heart rate during the boxing match.

Figure 3E:
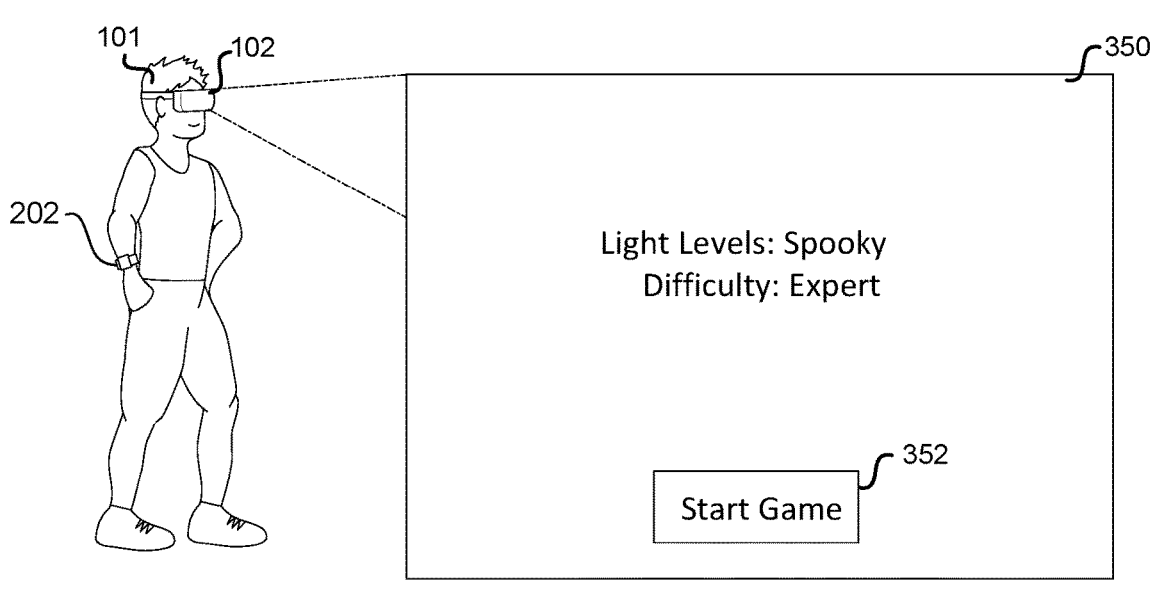
FIGS. 3E-3G illustrate another example user scenario of monitoring biometric data via a head-wearable device in accordance with some embodiments.
Figure 3F:
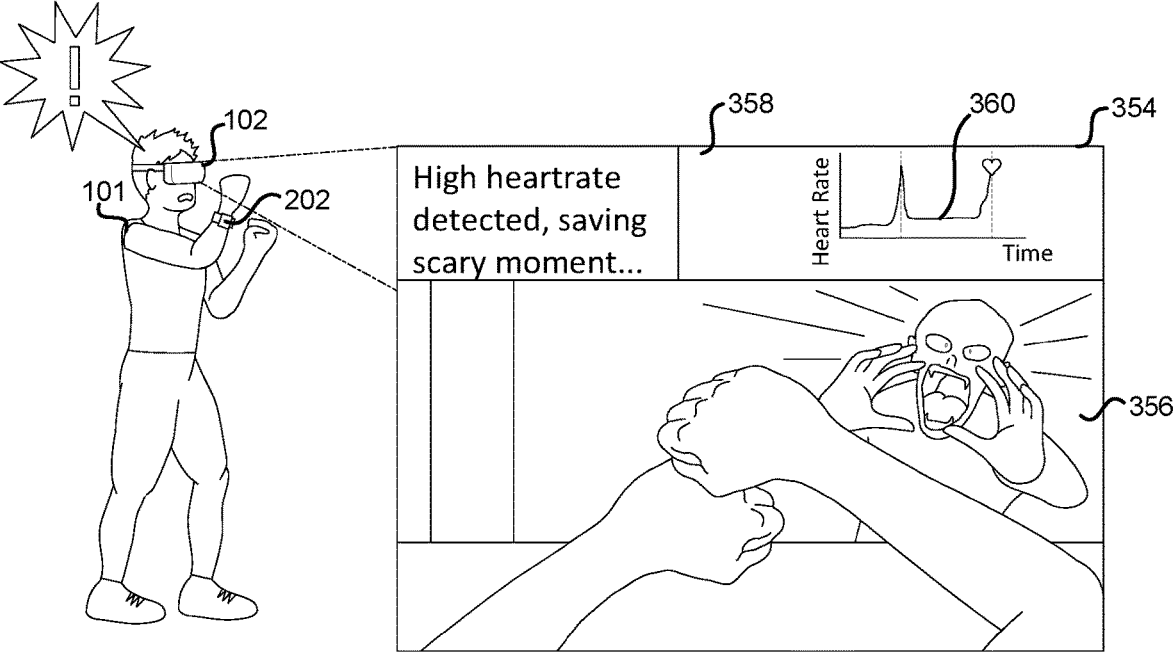
Figure 3G:
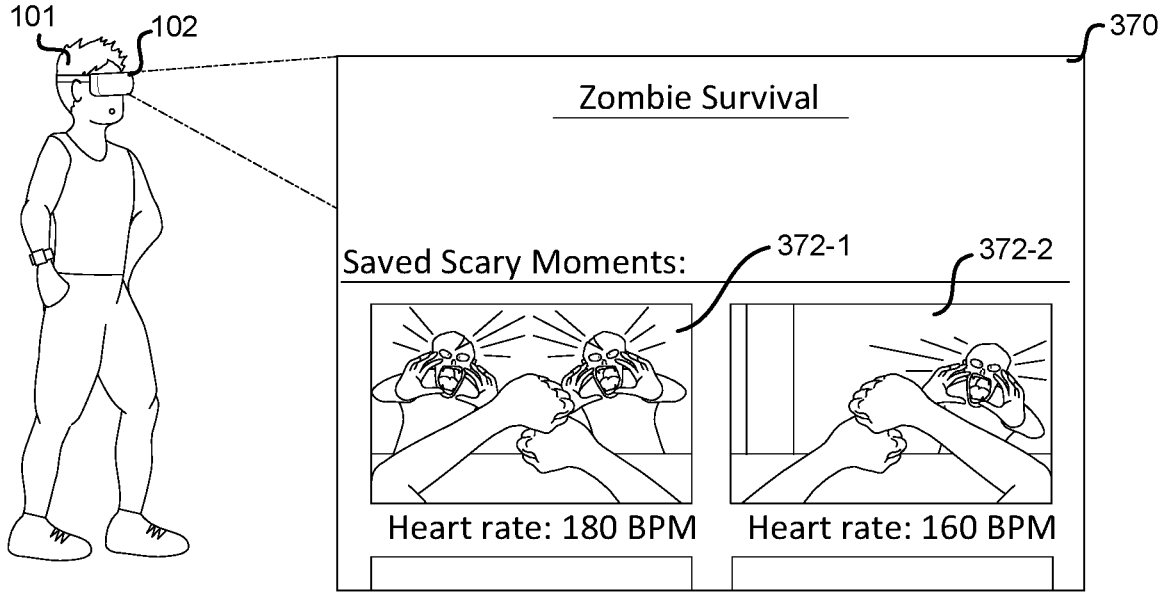

FIGS. 3E-3G illustrate another example user scenario of monitoring biometric data via the head-wearable device 102 in accordance with some embodiments. FIG. 3E shows the user 101 wearing the head-wearable device 102 and a wrist-wearable device 202. FIG. 3E further shows a user interface 350 (e.g., a horror game user interface) presented to the user 101 via the head-wearable device 102. The user interface 350 includes information about the horror game and a virtual button 352 to start playing the game.

FIG. 3F shows the user 101 playing the horror game as indicated by the user interface 354. The user interface 302 includes a gameplay portion 356 and an information portion 358 that includes a notification that a scary moment has been detected and heart rate information 360. The heart rate information 360 indicates the user's heart rate while playing the horror game. In some embodiments, the heart rate information 360 is obtained from PPG measurements obtained via the head-wearable device 102 and/or the wrist-wearable device 202. In some embodiments, the scary moment is detected based on the user's heart rate meeting or exceeding a preset threshold. In some embodiments, the scary moment is detected based on identification of a local maximum in the heart rate information 360. FIG. 3G shows the user 101 viewing a moments user interface 370, e.g., having stopped playing the horror game. The user interface 370 includes a plurality of scary moment clips 372, each with an associated heart rate measurement.

Figure 5A:
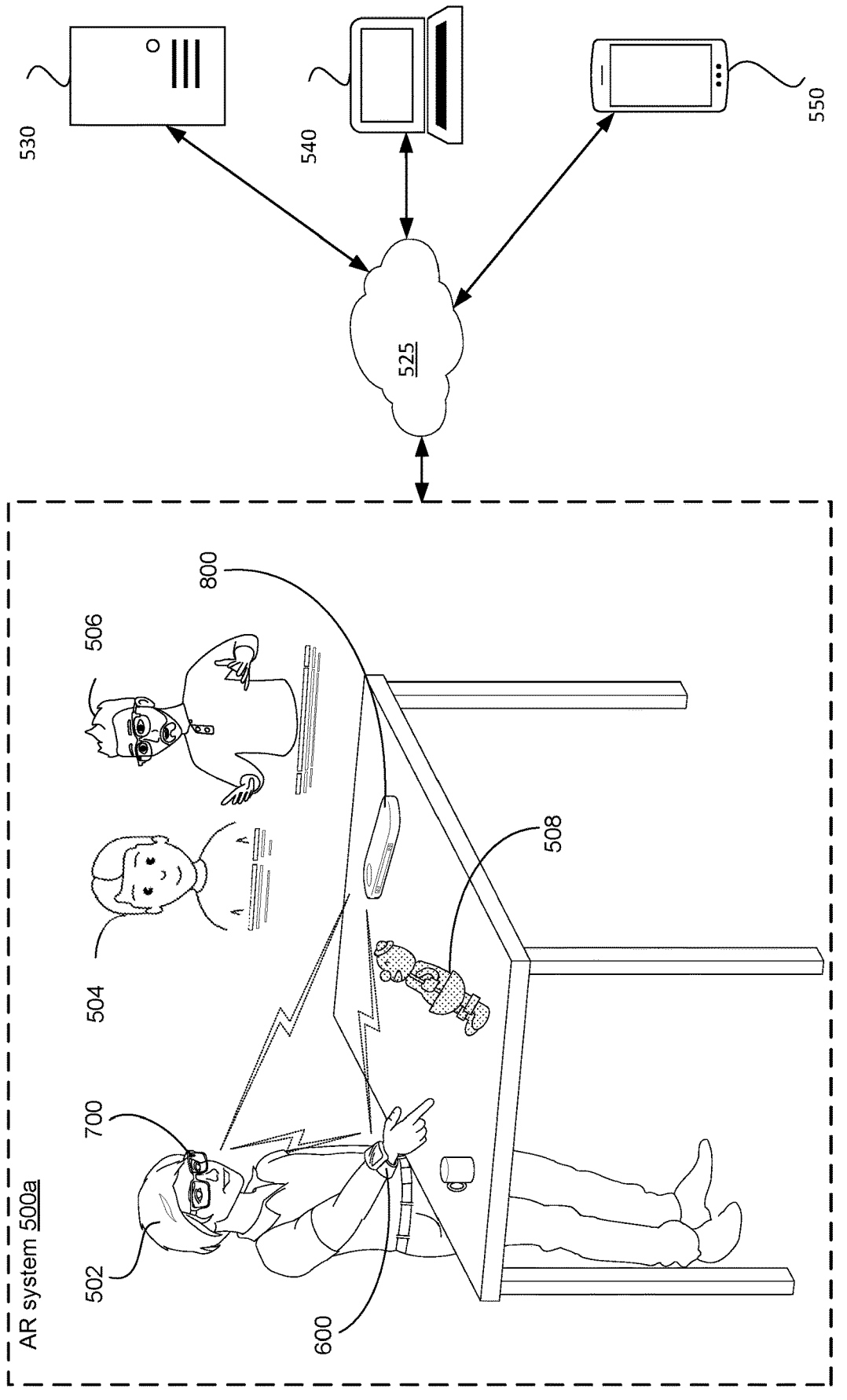
FIGS. 5A 5B, 5C-1, 5C-2, 5D-1, and 5D-2 illustrate example artificial-reality systems in accordance with some embodiments.
Figure 5B:
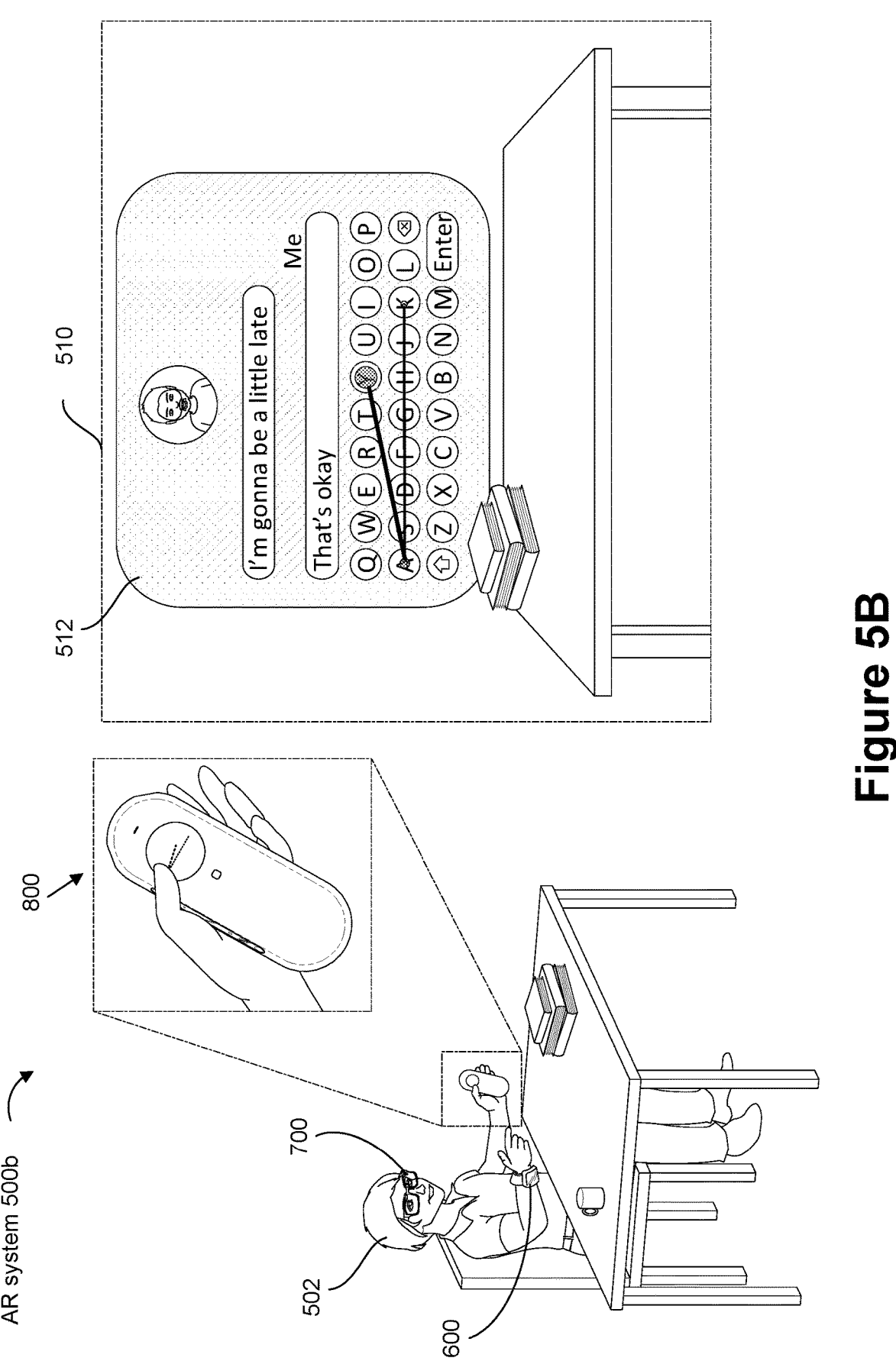
Figures 1, 5C:
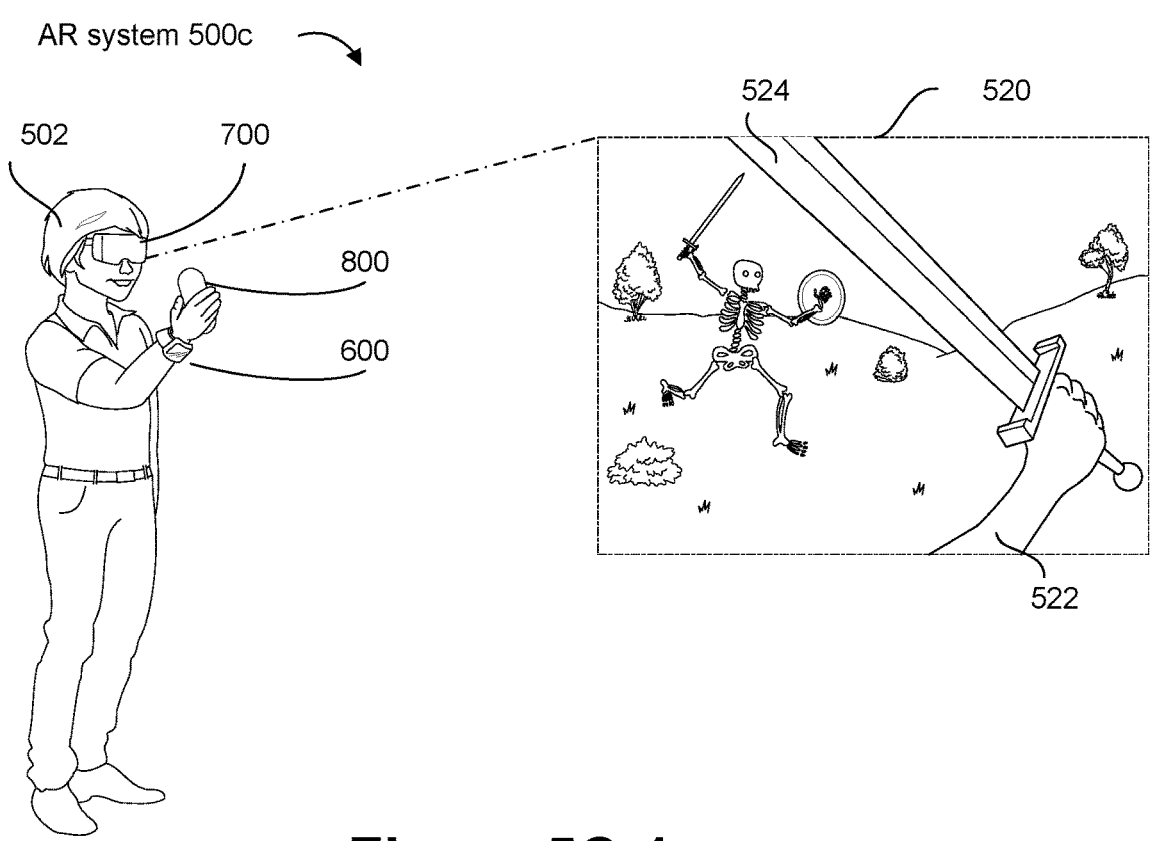
Figures 2, 5C:
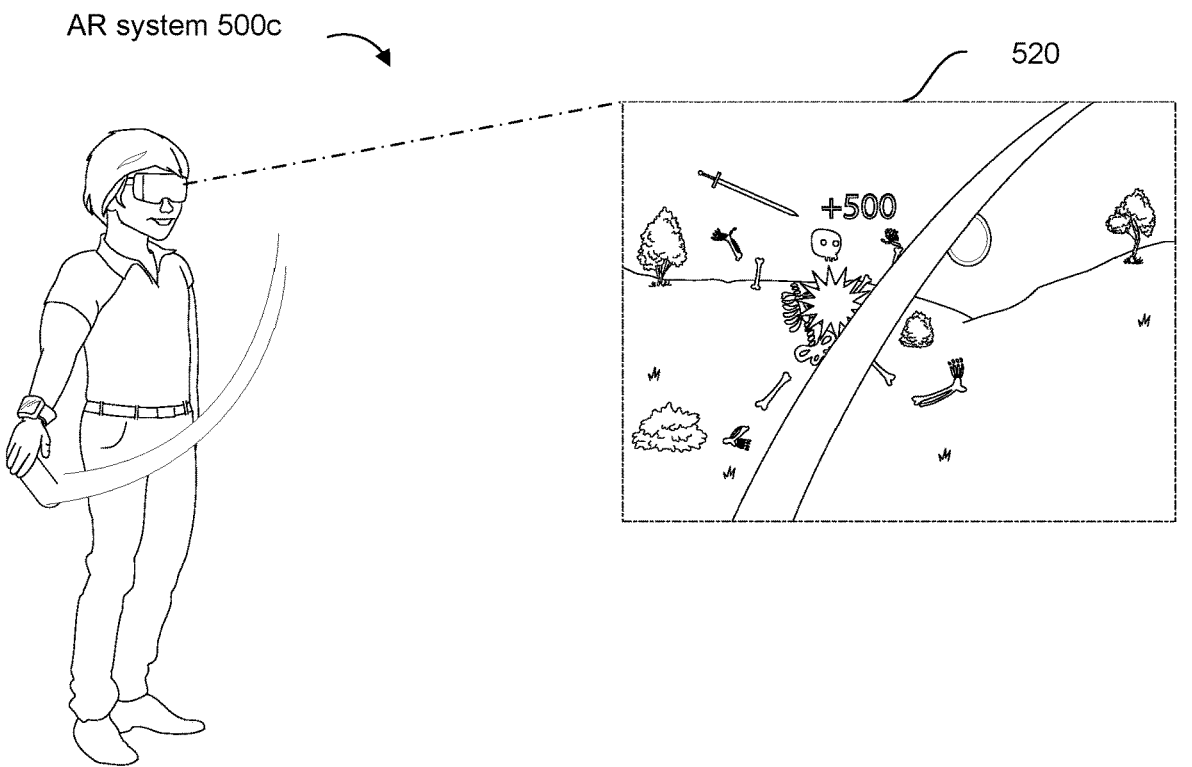

Additionally, although the user scenarios described with respect to the series of FIGS. 2 and 3 are described as separate sequences, in some embodiments the user scenarios are combined with one another. For example, the sequence described with respect to FIGS. 2A-2C could occur before (or after) the sequences described with respect to FIGS. 3A-3D and 3E-3G (e.g., all three sequences could occur while the user 101 is interacting with the head-wearable device 102).

The user scenarios described with respect to the series of FIGS. 2 and 3 involved specific user interface and applications, such as the user interfaces 204, 302, 312, 340, 350, 354, and 370. However, the sequences, gestures, actions, and operations can be used in conjunction with other types of user interfaces, menus, and applications such as web-browsing, note-taking, social media, word processing, data entry, programming, and the like.

Figure 4A:
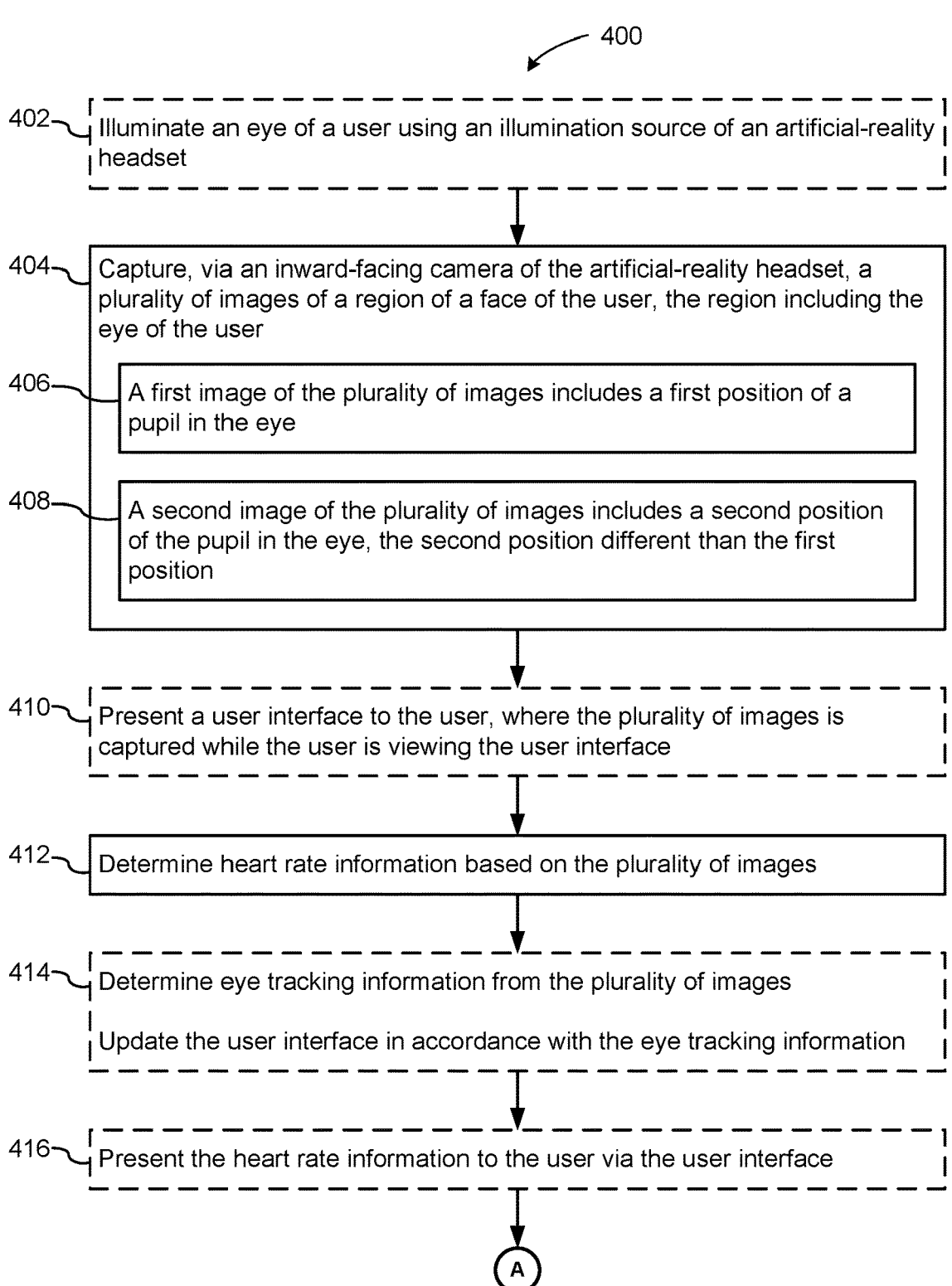

FIGS. 4A-4B are a flow diagram illustrating a method 400 for monitoring heart rate in accordance with some embodiments. The method 400 is performed at a computing system (e.g., a wearable device and/or an intermediary device) having one or more processors and memory. In some embodiments, the memory stores one or more programs configured for execution by the one or more processors. At least some of the operations shown in FIGS. 4A-4B correspond to instructions stored in a computer memory or a computer-readable storage medium (e.g., memory 650 of the wearable band 610, and/or memory 750A of the computing system 720). In some embodiments, the computing system is a wearable device such as the head-wearable device 102.

In some embodiments, the computing system is, or includes, an intermediary device such as a smartphone, personal computer, or video game console.

In some embodiments, the system illuminates (402) an eye (e.g., the eye 110) of a user using an illumination source (e.g., the illumination source 106) of an artificial-reality headset (e.g., the head-wearable device 102). In some embodiments, the illumination source emits infrared and/or near-infrared light.

The system captures (404), via an inward-facing camera (e.g., the camera 104) of the artificial-reality headset, a plurality of images of a region of a face of the user, the region including the eye of the user. For example, the region of the user's face can include the eye 110 and the facial tissue 112. In some embodiments, a first camera captures a plurality of images of an eye of the user and a second camera captures a plurality of images of facial tissue of the user (e.g., the system selects which to use for PPG and/or heart rate based on detected noise and/or variability).

A first image of the plurality of images includes (406) a first position of a pupil in the eye. A second image of the plurality of images includes (408) a second position of the pupil in the eye, the second position different than the first position. For example, PPG measurements are obtained based on blood flow in blood vessels of the retina, choroid, conjunctiva, and/or iris.

In some embodiments, the system presents (410) a user interface (e.g., the user interface 204) to the user, where the plurality of images is captured while the user is viewing the user interface. For example, the system presents user interfaces related to an application or video game and captures images of the user's eye while the user interacts with the user interfaces.

The system determines (412) heart rate information (e.g., heart rate information 118) based on the plurality of images. For example, the system measures PPG from the user's eye(s) and/or facial tissue and extrapolates heart rate information from the PPG.

In some embodiments, the system determines (414) eye-tracking information from the plurality of images and updates the user interface in accordance with the eye-tracking information. For example, the system allows a user to interact with the user interface based on eye movements, such as changing a field of view of a user or selecting a user interface element.

In some embodiments, the system presents (416) the heart rate information to the user via the user interface. For example, the system presents a heart rate graph (e.g., the heart rate graph 342), a maximum heart rate, and/or an average heart rate (e.g., the heart rate information 346).

In some embodiments, the system obtains (418) secondary heart rate information (e.g., from the PPG 222) from a wrist-wearable device (e.g., the wrist-wearable device 202) worn by the user. For example, the wrist-wearable device includes an image sensor focused on a wrist of the user and captures blood volume levels in the user's wrist. In this way, the system can obtain PPG measurements for the user and determine a user's heart rate based on the obtained PPG measurements. In some embodiments, the wrist-wearable device includes one or more non-image sensors for determining the user's heart rate.

In some embodiments, the system selects (420) the secondary heart rate information as selected heart rate information in accordance with the secondary heart rate information meeting one or more criteria, selects the heart rate information as the selected heart rate information in accordance with the secondary heart rate information not meeting one or more criteria, and presents the selected heart rate information to the user. For example, if the secondary heart rate information is too noisy and/or inconsistently obtained, the primary heart rate information is selected. In some cases, the secondary heart rate information is noisy and/or inconsistent due to the wrist-wearable device not being properly positioned (e.g., due to movement of the user).

In some embodiments, the system selects (422) the heart rate information as selected heart rate information in accordance with the heart rate information meeting one or more criteria, selects the secondary heart rate information as the selected heart rate information in accordance with the heart rate information not meeting one or more criteria, and presents the selected heart rate information to the user. For example, if the primary heart rate information is too noisy and/or inconsistently obtained, the secondary heart rate information is selected.

In some embodiments, the system aggregates (424) the heart rate information and the secondary heart rate information to obtain aggregated heart rate information; and presents the aggregated heart rate information to the user. For example, the system obtains average heart rate information from the heart rate information and the secondary heart rate information, and the system presents the average heart rate information to the user.

Figure 4C:
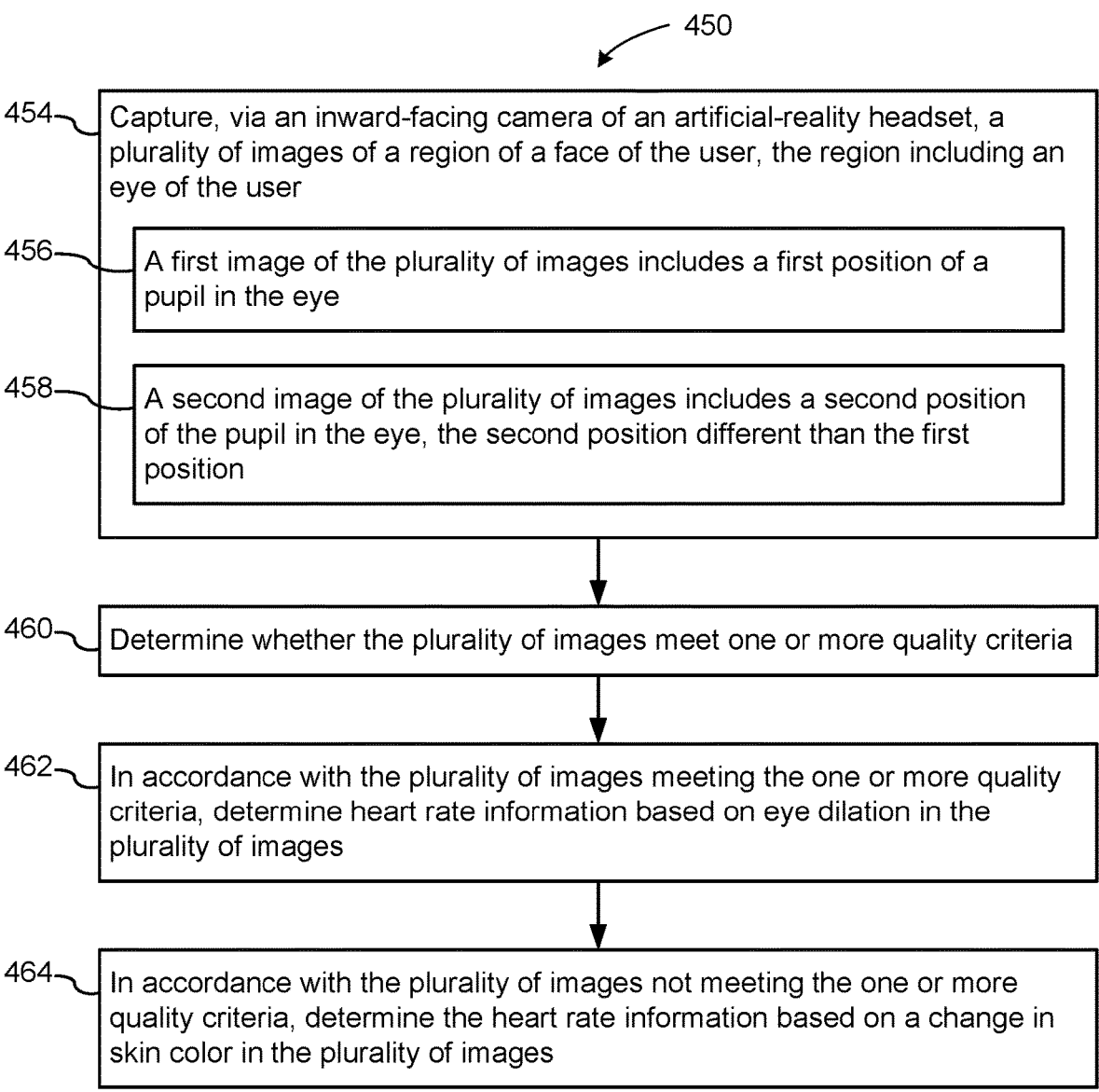
FIG. 4C is a flow diagram illustrating another example method for monitoring heart rate in accordance with some embodiments.

FIG. 4C is a flow diagram illustrating a method 450 for monitoring heart rate in accordance with some embodiments. The method 450 is performed at a computing system (e.g., a wearable device or intermediary device) having one or more processors and memory. In some embodiments, the memory stores one or more programs configured for execution by the one or more processors. At least some of the operations shown in FIG. 4C correspond to instructions stored in a computer memory or a computer-readable storage medium (e.g., memory 650 of the wearable band 610, and/or memory 750A of the computing system 720). In some embodiments, the computing system is a wearable device, such as the head-wearable device 102. In some embodiments, the computing system is, or includes, an intermediary device such as a smartphone, personal computer, or video game console.

The system captures (454), via an inward-facing camera (e.g., the camera 104) of an artificial-reality headset (e.g., the head-wearable device 102), a plurality of images of a region of a face of the user, the region including an eye of the user (e.g., the eye 110).

A first image of the plurality of images includes (456) a first position of a pupil in the eye. A second image of the plurality of images includes (458) a second position of the pupil in the eye, the second position different than the first position. For example, the user reads and/or looks around while the plurality of images is captured.

The system determines (460) whether the plurality of images meets one or more quality criteria. For example, the system determines whether blood volume levels for a particular region of the user's face are captured in the plurality of images. If the camera shifts with respect to the user's face or is obstructed or unfocused, the plurality of images may not meet the one or more quality criteria.

In accordance with the plurality of images meeting the one or more quality criteria, the system determines (462) heart rate information based the eye of the user in the plurality of images. For example, the heart rate information is determined based on movement of the eye, blood flow within the eye, and/or blood volume levels in the eye. For example, involuntary motion of the iris/pupil corresponds to a user's heartbeat and therefore corresponds to a heart rate of the user.

In accordance with the plurality of images not meeting the one or more quality criteria, the system determines (464) the heart rate information based on a change in skin color in the plurality of images. For example, the system determines whether the eye (e.g., the eye 110) of the user is visible and in focus in the plurality of images. In this example, if the eye of the user is obstructed or out of focus in at least a subset of the images, the system determines the heart rate information from facial tissue (e.g., the facial tissue 112) captured in the plurality of images.

It should be understood that the particular order in which the operations in FIGS. 4A-4C have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein (e.g., the method 400) are also applicable in an analogous manner to method 450 described above.

The operations described above with reference to FIGS. 4A-4C are, optionally, implemented by components depicted in FIGS. 1, 5A-5B, 5C-1, 5C-2, 5D-1, and 5D-2, 6A-6B, and 7A, 7B-1, 7B-2, 7C, 8A-8B, and 9A-9C. For example, the illuminate operation 402, capture operation 404, and determination operation 412 are, optionally, implemented by the illumination source 106, the imaging sensor 726 and the processor(s) 748A of the computing system 720. Similarly, it would be clear to a person having ordinary skill in the art how other processes can be implemented based on the components depicted in FIGS. 1, 5A-5B, 5C-1, 5C-2, 5D-1, and 5D-2, 6A-6B, and 7A, 7B-1, 7B-2, 7C, 8A-8B, and 9A-9C.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Having thus described example sequences and methods of operation that make use of the example sequences, attention will now be directed to system-level depictions of hardware and software on which (or with which) the methods can be implemented.

The devices described above are further detailed below, including systems, wrist-wearable devices, headset devices, and smart textile-based garments. Specific operations described above may occur as a result of specific hardware, such hardware is described in further detail below. The devices described below are not limiting and features on these devices can be removed or additional features can be added to these devices. The different devices can include one or more analogous hardware components. For brevity, analogous devices and components are described below. Any differences in the devices and components are described below in their respective sections.

As described herein, a processor (e.g., a central processing unit (CPU) or microcontroller unit (MCU)), is an electronic component that is responsible for executing instructions and controlling the operation of an electronic device (e.g., a wrist-wearable device 600, a head-wearable device, an HIPD 800, a smart textile-based garment 900, or other computer system). There are various types of processors that may be used interchangeably or specifically required by embodiments described herein. For example, a processor may be (i) a general processor designed to perform a wide range of tasks, such as running software applications, managing operating systems, and performing arithmetic and logical operations; (ii) a microcontroller designed for specific tasks such as controlling electronic devices, sensors, and motors; (iii) a graphics processing unit (GPU) designed to accelerate the creation and rendering of images, videos, and animations (e.g., virtual-reality animations, such as three-dimensional modeling); (iv) a field-programmable gate array (FPGA) that can be programmed and reconfigured after manufacturing and/or customized to perform specific tasks, such as signal processing, cryptography, and machine learning; (v) a digital signal processor (DSP) designed to perform mathematical operations on signals such as audio, video, and radio waves. One of skill in the art will understand that one or more processors of one or more electronic devices may be used in various embodiments described herein.

As described herein, controllers are electronic components that manage and coordinate the operation of other components within an electronic device (e.g., controlling inputs, processing data, and/or generating outputs). Examples of controllers can include (i) microcontrollers, including small, low-power controllers that are commonly used in embedded systems and Internet of Things (IoT) devices; (ii) programmable logic controllers (PLCs) that may be configured to be used in industrial automation systems to control and monitor manufacturing processes; (iii) system-on-a-chip (SoC) controllers that integrate multiple components such as processors, memory, I/O interfaces, and other peripherals into a single chip; and/or DSPs. As described herein, a graphics module is a component or software module that is designed to handle graphical operations and/or processes and can include a hardware module and/or a software module.

As described herein, memory refers to electronic components in a computer or electronic device that store data and instructions for the processor to access and manipulate. The devices described herein can include volatile and non-volatile memory. Examples of memory can include (i) random access memory (RAM), such as DRAM, SRAM, DDR RAM or other random access solid state memory devices, configured to store data and instructions temporarily; (ii) read-only memory (ROM) configured to store data and instructions permanently (e.g., one or more portions of system firmware and/or boot loaders); (iii) flash memory, magnetic disk storage devices, optical disk storage devices, other non-volatile solid state storage devices, which can be configured to store data in electronic devices (e.g., universal serial bus (USB) drives, memory cards, and/or solid-state drives (SSDs)); and (iv) cache memory configured to temporarily store frequently accessed data and instructions. Memory, as described herein, can include structured data (e.g., SQL databases, MongoDB databases, GraphQL data, or JSON data). Other examples of memory can include: (i) profile data, including user account data, user settings, and/or other user data stored by the user; (ii) sensor data detected and/or otherwise obtained by one or more sensors; (iii) media content data including stored image data, audio data, documents, and the like; (iv) application data, which can include data collected and/or otherwise obtained and stored during use of an application; and/or any other types of data described herein.

As described herein, a power system of an electronic device is configured to convert incoming electrical power into a form that can be used to operate the device. A power system can include various components, including (i) a power source, which can be an alternating current (AC) adapter or a direct current (DC) adapter power supply; (ii) a charger input that can be configured to use a wired and/or wireless connection (which may be part of a peripheral interface, such as a USB, micro-USB interface, near-field magnetic coupling, magnetic inductive and magnetic reso-nance charging, and/or radio frequency (RF) charging); (iii) a power-management integrated circuit, configured to dis-tribute power to various components of the device and ensure that the device operates within safe limits (e.g., regulating voltage, controlling current flow, and/or manag-ing heat dissipation); and/or (iv) a battery configured to store power to provide usable power to components of one or more electronic devices.

As described herein, peripheral interfaces are electronic components (e.g., of electronic devices) that allow elec-tronic devices to communicate with other devices or periph-erals and can provide a means for input and output of data and signals. Examples of peripheral interfaces can include (i) USB and/or micro-USB interfaces configured for con-necting devices to an electronic device; (ii) Bluetooth inter-faces configured to allow devices to communicate with each other, including Bluetooth low energy (BLE); (iii) near-field communication (NFC) interfaces configured to be short-range wireless interfaces for operations such as access control; (iv) POGO pins, which may be small, spring-loaded pins configured to provide a charging interface; (v) wireless charging interfaces; (vi) global-position system (GPS) inter-faces; (vii) Wi-Fi interfaces for providing a connection between a device and a wireless network; and (viii) sensor interfaces.

As described herein, sensors are electronic components (e.g., in and/or otherwise in electronic communication with electronic devices, such as wearable devices) configured to detect physical and environmental changes and generate electrical signals. Examples of sensors can include (i) imag-ing sensors for collecting imaging data (e.g., including one or more cameras disposed on a respective electronic device); (ii) biopotential-signal sensors; (iii) inertial measurement unit (e.g., IMUs) for detecting, for example, angular rate, force, magnetic field, and/or changes in acceleration; (iv) heart rate sensors for measuring a user's heart rate; (v) SpO2 sensors for measuring blood oxygen saturation and/or other biometric data of a user; (vi) capacitive sensors for detecting changes in potential at a portion of a user's body (e.g., a sensor-skin interface) and/or the proximity of other devices or objects; and (vii) light sensors (e.g., ToF sensors, infrared light sensors, or visible light sensors), and/or sensors for sensing data from the user or the user's environment. As described herein biopotential-signal-sensing components are devices used to measure electrical activity within the body (e.g., biopotential-signal sensors). Some types of bio-potential-signal sensors include: (i) electroencephalography (EEG) sensors configured to measure electrical activity in the brain to diagnose neurological disorders; (ii) electrocar-diography (ECG or EKG) sensors configured to measure electrical activity of the heart to diagnose heart problems; (iii) electromyography (EMG) sensors configured to mea-sure the electrical activity of muscles and diagnose neuro-muscular disorders; (iv) electrooculography (EOG) sensors configured to measure the electrical activity of eye muscles to detect eye movement and diagnose eye disorders.

As described herein, an application stored in memory of an electronic device (e.g., software) includes instructions stored in the memory. Examples of such applications include (i) games; (ii) word processors; (iii) messaging applications; (iv) media-streaming applications; (v) financial applications; (vi) calendars; (vii) clocks; (viii) web browsers; (ix) social media applications, (x) camera applications, (xi) web-based applications; (xii) health applications; (xiii) artificial-reality (AR) applications, and/or any other applications that can be stored in memory. The applications can operate in conjunc-tion with data and/or one or more components of a device or communicatively coupled devices to perform one or more operations and/or functions.

As described herein, communication interface modules can include hardware and/or software capable of data com-munications using any of a variety of custom or standard wireless protocols (e.g., IEEE 802.15.4, Wi-Fi, ZigBee, 6LoWPAN, Thread, Z-Wave, Bluetooth Smart, ISA100.11a, WirelessHART, or MiWi), custom or standard wired proto-cols (e.g., Ethernet or HomePlug), and/or any other suitable communication protocol, including communication proto-cols not yet developed as of the filing date of this document. A communication interface is a mechanism that enables different systems or devices to exchange information and data with each other, including hardware, software, or a combination of both hardware and software. For example, a communication interface can refer to a physical connector and/or port on a device that enables communication with other devices (e.g., USB, Ethernet, HDMI, or Bluetooth). In some embodiments, a communication interface can refer to a software layer that enables different software programs to communicate with each other (e.g., application program-ming interfaces (APIs) and protocols such as HTTP and TCP/IP).

As described herein, a graphics module is a component or software module that is designed to handle graphical opera-tions and/or processes, and can include a hardware module and/or a software module.

As described herein, non-transitory computer-readable storage media are physical devices or storage medium that can be used to store electronic data in a non-transitory form (e.g., such that the data is stored permanently until it is intentionally deleted or modified).

Example AR Systems 5A-5D-2

Figures 1, 5D:
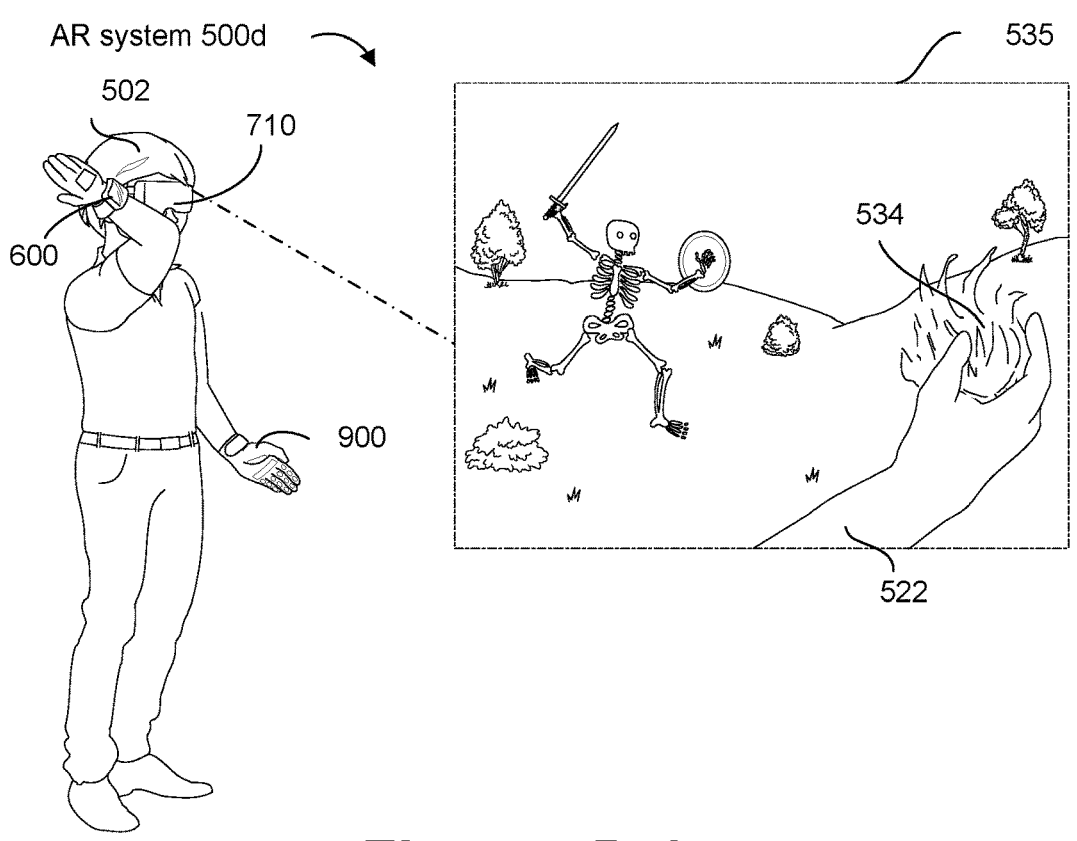
Figures 2, 5D:
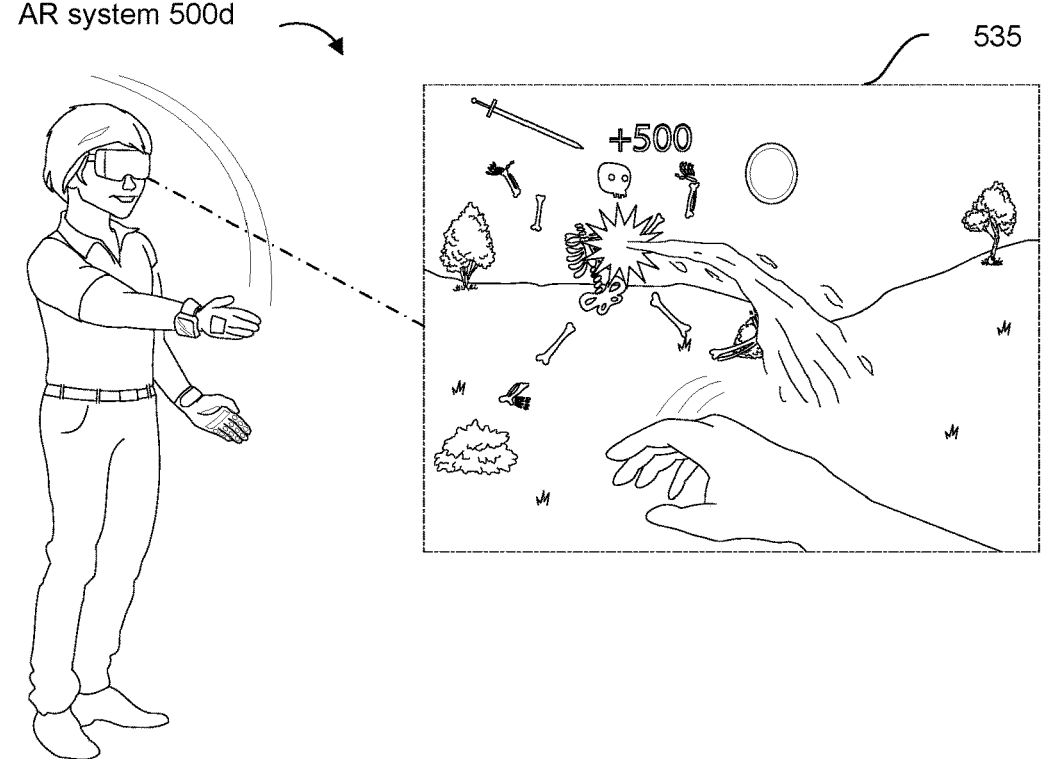

FIGS. 5A, 5B, 5C-1, 5C-2, 5D-1, and 5D-2 illustrate example AR systems in accordance with some embodiments. FIG. 5A shows a first AR system 500*a* and first example user interactions using a wrist-wearable device 600, a head-wearable device (e.g., AR device 700), and/or a handheld intermediary processing device (HIPD) 800. FIG. 5B shows a second AR system 500*b* and second example user interactions using a wrist-wearable device 600, AR device 700, and/or an HIPD 800. FIGS. 5C-1 and 5C-2 show a third AR system 500*c* and third example user interactions using a wrist-wearable device 600, a head-wearable device (e.g., virtual-reality (VR) device 710), and/or an HIPD 800. FIGS. 5D-1 and 5D-2 show a fourth AR system 500*d* and fourth example user interactions using a wrist-wearable device 600, VR device 710, and/or a smart textile-based garment 900 (e.g., wearable gloves, haptic gloves). As the skilled artisan will appreciate upon reading the descriptions provided herein, the above-example AR systems (described in detail below) can perform various functions and/or operations described above with reference to FIGS. 1A to 4C.

The wrist-wearable device 600 and its constituent components are described below in reference to FIGS. 6A-6B, the head-wearable devices and their constituent components are described below in reference to FIGS. 7A-7D, and the HIPD 800 and its constituent components are described below in reference to FIGS. 8A-8B. The smart textile-based garment 900 and its one or more components are described below in reference to FIGS. 9A-9C. The wrist-wearable device 600, the head-wearable devices, and/or the HIPD 800 can communicatively couple via a network 525 (e.g., cellular, near field, Wi-Fi, personal area network, or wireless LAN). Additionally, the wrist-wearable device 600, the head-wearable devices, and/or the HIPD 800 can also communicatively couple with one or more servers 530, computers 540 (e.g., laptops or computers), mobile devices 550 (e.g., smartphones or tablets), and/or other electronic devices via the network 525 (e.g., cellular, near field, Wi-Fi, personal area network, or wireless LAN). Similarly, the smart textile-based garment 900, when used, can also communicatively couple with the wrist-wearable device 600, the head-wearable devices, the HIPD 800, the one or more servers 530, the computers 540, the mobile devices 550, and/or other electronic devices via the network 525.

Turning to FIG. 5A, a user 502 is shown wearing the wrist-wearable device 600 and the AR device 700 and having the HIPD 800 on their desk. The wrist-wearable device 600, the AR device 700, and the HIPD 800 facilitate user interaction with an AR environment. In particular, as shown by the first AR system 500*a*, the wrist-wearable device 600, the AR device 700, and/or the HIPD 800 cause presentation of one or more avatars 504, digital representations of contacts 506, and virtual objects 508. As discussed below, the user 502 can interact with the one or more avatars 504, digital representations of the contacts 506, and virtual objects 508 via the wrist-wearable device 600, the AR device 700, and/or the HIPD 800.

The user 502 can use any of the wrist-wearable device 600, the AR device 700, and/or the HIPD 800 to provide user inputs. For example, the user 502 can perform one or more hand gestures that are detected by the wrist-wearable device 600 (e.g., using one or more EMG sensors and/or IMUs, described below in reference to FIGS. 6A-6B) and/or AR device 700 (e.g., using one or more image sensors or cameras, described below in reference to FIGS. 7A-7B) to provide a user input. Alternatively, or additionally, the user 502 can provide a user input via one or more touch surfaces of the wrist-wearable device 600, the AR device 700, and/or the HIPD 800, and/or voice commands captured by a microphone of the wrist-wearable device 600, the AR device

700, and/or the HIPD 800. In some embodiments, the wrist-wearable device 600, the AR device 700, and/or the HIPD 800 include a digital assistant to help the user in providing a user input (e.g., completing a sequence of operations, suggesting different operations or commands, providing reminders, or confirming a command). In some embodiments, the user 502 can provide a user input via one or more facial gestures and/or facial expressions. For example, cameras of the wrist-wearable device 600, the AR device 700, and/or the HIPD 800 can track the user 502's eyes for navigating a user interface.

The wrist-wearable device 600, the AR device 700, and/or the HIPD 800 can operate alone or in conjunction to allow the user 502 to interact with the AR environment. In some embodiments, the HIPD 800 is configured to operate as a central hub or control center for the wrist-wearable device 600, the AR device 700, and/or another communicatively coupled device. For example, the user 502 can provide an input to interact with the AR environment at any of the wrist-wearable device 600, the AR device 700, and/or the HIPD 800, and the HIPD 800 can identify one or more back-end and front-end tasks to cause the performance of the requested interaction and distribute instructions to cause the performance of the one or more back-end and front-end tasks at the wrist-wearable device 600, the AR device 700, and/or the HIPD 800. In some embodiments, a back-end task is a background-processing task that is not perceptible by the user (e.g., rendering content, decompression, or compression), and a front-end task is a user-facing task that is perceptible to the user (e.g., presenting information to the user or providing feedback to the user). As described below in reference to FIGS. 8A-8B, the HIPD 800 can perform the back-end tasks and provide the wrist-wearable device 600 and/or the AR device 700 operational data corresponding to the performed back-end tasks such that the wrist-wearable device 600 and/or the AR device 700 can perform the front-end tasks. In this way, the HIPD 800, which has more computational resources and greater thermal headroom than the wrist-wearable device 600 and/or the AR device 700, performs computationally intensive tasks and reduces the computer resource utilization and/or power usage of the wrist-wearable device 600 and/or the AR device 700.

In the example shown by the first AR system 500*a*, the HIPD 800 identifies one or more back-end tasks and front-end tasks associated with a user request to initiate an AR video call with one or more other users (represented by the avatar 504 and the digital representation of the contact 506) and distributes instructions to cause the performance of the one or more back-end tasks and front-end tasks. In particular, the HIPD 800 performs back-end tasks for processing and/or rendering image data (and other data) associated with the AR video call and provides operational data associated with the performed back-end tasks to the AR device 700 such that the AR device 700 performs front-end tasks for presenting the AR video call (e.g., presenting the avatar 504 and the digital representation of the contact 506).

In some embodiments, the HIPD 800 can operate as a focal or anchor point for causing the presentation of information. This allows the user 502 to be generally aware of where information is presented. For example, as shown in the first AR system 500*a*, the avatar 504 and the digital representation of the contact 506 are presented above the HIPD 800. In particular, the HIPD 800 and the AR device 700 operate in conjunction to determine a location for presenting the avatar 504 and the digital representation of the contact 506. In some embodiments, information can be presented within a predetermined distance from the HIPD 800 (e.g., within five meters). For example, as shown in the first AR system 500a, virtual object 508 is presented on the desk some distance from the HIPD 800. Similar to the above example, the HIPD 800 and the AR device 700 can operate in conjunction to determine a location for presenting the virtual object 508. Alternatively, in some embodiments, presentation of information is not bound by the HIPD 800. More specifically, the avatar 504, the digital representation of the contact 506, and the virtual object 508 do not have to be presented within a predetermined distance of the HIPD 800.

User inputs provided at the wrist-wearable device 600, the AR device 700, and/or the HIPD 800 are coordinated such that the user can use any device to initiate, continue, and/or complete an operation. For example, the user 502 can provide a user input to the AR device 700 to cause the AR device 700 to present the virtual object 508 and, while the virtual object 508 is presented by the AR device 700, the user 502 can provide one or more hand gestures via the wrist-wearable device 600 to interact and/or manipulate the virtual object 508.

FIG. 5B shows the user 502 wearing the wrist-wearable device 600 and the AR device 700, and holding the HIPD 800. In the second AR system 500b, the wrist-wearable device 600, the AR device 700, and/or the HIPD 800 are used to receive and/or provide one or more messages to a contact of the user 502. In particular, the wrist-wearable device 600, the AR device 700, and/or the HIPD 800 detect and coordinate one or more user inputs to initiate a messaging application and prepare a response to a received message via the messaging application.

In some embodiments, the user 502 initiates, via a user input, an application on the wrist-wearable device 600, the AR device 700, and/or the HIPD 800 that causes the application to initiate on at least one device. For example, in the second AR system 500b, the user 502 performs a hand gesture associated with a command for initiating a messaging application (represented by messaging user interface 512), the wrist-wearable device 600 detects the hand gesture, and, based on a determination that the user 502 is wearing AR device 700, causes the AR device 700 to present a messaging user interface 512 of the messaging application. The AR device 700 can present the messaging user interface 512 to the user 502 via its display (e.g., as shown by user 502's field of view 510). In some embodiments, the application is initiated and can be run on the device (e.g., the wrist-wearable device 600, the AR device 700, and/or the HIPD 800) that detects the user input to initiate the application, and the device provides another device operational data to cause the presentation of the messaging application. For example, the wrist-wearable device 600 can detect the user input to initiate a messaging application, initiate and run the messaging application, and provide operational data to the AR device 700 and/or the HIPD 800 to cause presentation of the messaging application. Alternatively, the application can be initiated and run at a device other than the device that detected the user input. For example, the wrist-wearable device 600 can detect the hand gesture associated with initiating the messaging application and cause the HIPD 800 to run the messaging application and coordinate the presentation of the messaging application.

Further, the user 502 can provide a user input provided at the wrist-wearable device 600, the AR device 700, and/or the HIPD 800 to continue and/or complete an operation initiated at another device. For example, after initiating the messaging application via the wrist-wearable device 600 and while the AR device 700 presents the messaging user interface 512, the user 502 can provide an input at the HIPD 800 to prepare a response (e.g., shown by the swipe gesture performed on the HIPD 800). The user 502's gestures performed on the HIPD 800 can be provided and/or displayed on another device. For example, the user 502's swipe gestures performed on the HIPD 800 are displayed on a virtual keyboard of the messaging user interface 512 displayed by the AR device 700.

In some embodiments, the wrist-wearable device 600, the AR device 700, the HIPD 800, and/or other communicatively coupled devices can present one or more notifications to the user 502. The notification can be an indication of a new message, an incoming call, an application update, a status update, etc. The user 502 can select the notification via the wrist-wearable device 600, the AR device 700, or the HIPD 800 and cause presentation of an application or operation associated with the notification on at least one device. For example, the user 502 can receive a notification that a message was received at the wrist-wearable device 600, the AR device 700, the HIPD 800, and/or other communicatively coupled device and provide a user input at the wrist-wearable device 600, the AR device 700, and/or the HIPD 800 to review the notification, and the device detecting the user input can cause an application associated with the notification to be initiated and/or presented at the wrist-wearable device 600, the AR device 700, and/or the HIPD 800.

While the above example describes coordinated inputs used to interact with a messaging application, the skilled artisan will appreciate upon reading the descriptions that user inputs can be coordinated to interact with any number of applications including, but not limited to, gaming applications, social media applications, camera applications, web-based applications, financial applications, etc. For example, the AR device 700 can present to the user 502 game application data and the HIPD 800 can use a controller to provide inputs to the game. Similarly, the user 502 can use the wrist-wearable device 600 to initiate a camera of the AR device 700, and the user can use the wrist-wearable device 600, the AR device 700, and/or the HIPD 800 to manipulate the image capture (e.g., zoom in or out or apply filters) and capture image data.

Turning to FIGS. 5C-1 and 5C-2, the user 502 is shown wearing the wrist-wearable device 600 and a VR device 710, and holding the HIPD 800. In the third AR system 500c, the wrist-wearable device 600, the VR device 710, and/or the HIPD 800 are used to interact within an AR environment, such as a VR game or other AR application. While the VR device 710 presents a representation of a VR game (e.g., first AR game environment 520) to the user 502, the wrist-wearable device 600, the VR device 710, and/or the HIPD 800 detect and coordinate one or more user inputs to allow the user 502 to interact with the VR game.

In some embodiments, the user 502 can provide a user input via the wrist-wearable device 600, the VR device 710, and/or the HIPD 800 that causes an action in a corresponding AR environment. For example, the user 502 in the third AR system 500c (shown in FIG. 5C-1) raises the HIPD 800 to prepare for a swing in the first AR game environment 520. The VR device 710, responsive to the user 502 raising the HIPD 800, causes the AR representation of the user 522 to perform a similar action (e.g., raise a virtual object, such as a virtual sword 524). In some embodiments, each device uses respective sensor data and/or image data to detect the user input and provide an accurate representation of the user 502's motion. For example, imaging sensors 854 (e.g., SLAM cameras or other cameras discussed below in FIGS.

8A and 8B) of the HIPD 800 can be used to detect a position of the 800 relative to the user 502's body such that the virtual object can be positioned appropriately within the first AR game environment 520; sensor data from the wrist-wearable device 600 can be used to detect a velocity at which the user 502 raises the HIPD 800 such that the AR representation of the user 522 and the virtual sword 524 are synchronized with the user 502's movements; and image sensors 726 (FIGS. 7A-7C) of the VR device 710 can be used to represent the user 502's body, boundary conditions, or real-world objects within the first AR game environment 520.

In FIG. 5C-2, the user 502 performs a downward swing while holding the HIPD 800. The user 502's downward swing is detected by the wrist-wearable device 600, the VR device 710, and/or the HIPD 800 and a corresponding action is performed in the first AR game environment 520. In some embodiments, the data captured by each device is used to improve the user's experience within the AR environment. For example, sensor data of the wrist-wearable device 600 can be used to determine a speed and/or force at which the downward swing is performed and image sensors of the HIPD 800 and/or the VR device 710 can be used to determine a location of the swing and how it should be represented in the first AR game environment 520, which, in turn, can be used as inputs for the AR environment (e.g., game mechanics, which can use detected speed, force, locations, and/or aspects of the user 502's actions to classify a user's inputs (e.g., user performs a light strike, hard strike, critical strike, glancing strike, miss) or calculate an output (e.g., amount of damage)).

While the wrist-wearable device 600, the VR device 710, and/or the HIPD 800 are described as detecting user inputs, in some embodiments, user inputs are detected at a single device (with the single device being responsible for distributing signals to the other devices for performing the user input). For example, the HIPD 800 can operate an application for generating the first AR game environment 520 and provide the VR device 710 with corresponding data for causing the presentation of the first AR game environment 520, as well as detect the 502's movements (while holding the HIPD 800) to cause the performance of corresponding actions within the first AR game environment 520. Additionally, or alternatively, in some embodiments, operational data (e.g., sensor data, image data, application data, device data, and/or other data) of one or more devices is provide to a single device (e.g., the HIPD 800) to process the operational data and cause respective devices to perform an action associated with processed operational data.

In FIGS. 5D-1 and 5D-2, the user 502 is shown wearing the wrist-wearable device 600, the VR device 710, and smart textile-based garments 900. In the fourth AR system 500*d*, the wrist-wearable device 600, the VR device 710, and/or the smart textile-based garments 900 are used to interact within an AR environment (e.g., any AR system described above in reference to FIGS. 5A-5C-2, as well as [INCLUDE ANY RELEVANT FIGURES]). While the VR device 710 presents a representation of a VR game (e.g., second AR game environment 535) to the user 502, the wrist-wearable device 600, the VR device 710, and/or the smart textile-based garments 900 detect and coordinate one or more user inputs to allow the user 502 to interact with the AR environment.

In some embodiments, the user 502 can provide a user input via the wrist-wearable device 600, the VR device 710, and/or the smart textile-based garments 900 that causes an action in a corresponding AR environment. For example, the user 502 in the fourth AR system 500*d* (shown in FIG. 5D-1)

raises a hand wearing the smart textile-based garments 900 to prepare to cast a spell or throw an object within the second AR game environment 535. The VR device 710, responsive to the user 502 holding up their hand (wearing smart textile-based garments 900), causes the AR representation of the user 522 to perform a similar action (e.g., hold a virtual object or throw a fireball 534). In some embodiments, each device uses respective sensor data and/or image data to detect the user input and provides an accurate representation of the user 502's motion.

In FIG. 5D-2, the user 502 performs a throwing motion while wearing the smart textile-based garment 900. The user 502's throwing motion is detected by the wrist-wearable device 600, the VR device 710, and/or the smart textile-based garments 900, and a corresponding action is performed in the second AR game environment 535. As described above, the data captured by each device is used to improve the user's experience within the AR environment. Although not shown, the smart textile-based garments 900 can be used in conjunction with an VR device 710 and/or an HIPD 800.

Having discussed example AR systems, devices for interacting with such AR systems, and other computing systems more generally, devices and components will now be discussed in greater detail below. Some definitions of devices and components that can be included in some or all of the example devices discussed below are defined here for ease of reference. A skilled artisan will appreciate that certain types of the components described below may be more suitable for a particular set of devices and less suitable for a different set of devices. But subsequent references to the components defined here should be considered to be encompassed by the definitions provided.

In some embodiments discussed below, example devices and systems, including electronic devices and systems, will be discussed. Such example devices and systems are not intended to be limiting, and one of skill in the art will understand that alternative devices and systems to the example devices and systems described herein may be used to perform the operations and construct the systems and devices that are described herein.

As described herein, an electronic device is a device that uses electrical energy to perform a specific function. It can be any physical object that contains electronic components such as transistors, resistors, capacitors, diodes, and integrated circuits. Examples of electronic devices include smartphones, laptops, digital cameras, televisions, gaming consoles, and music players, as well as the example electronic devices discussed herein. As described herein, an intermediary electronic device is a device that sits between two other electronic devices and/or a subset of components of one or more electronic devices, which facilitates communication, and/or data processing, and/or data transfer between the respective electronic devices and/or electronic components.

Example Wrist-Wearable Devices

Figure 6A:
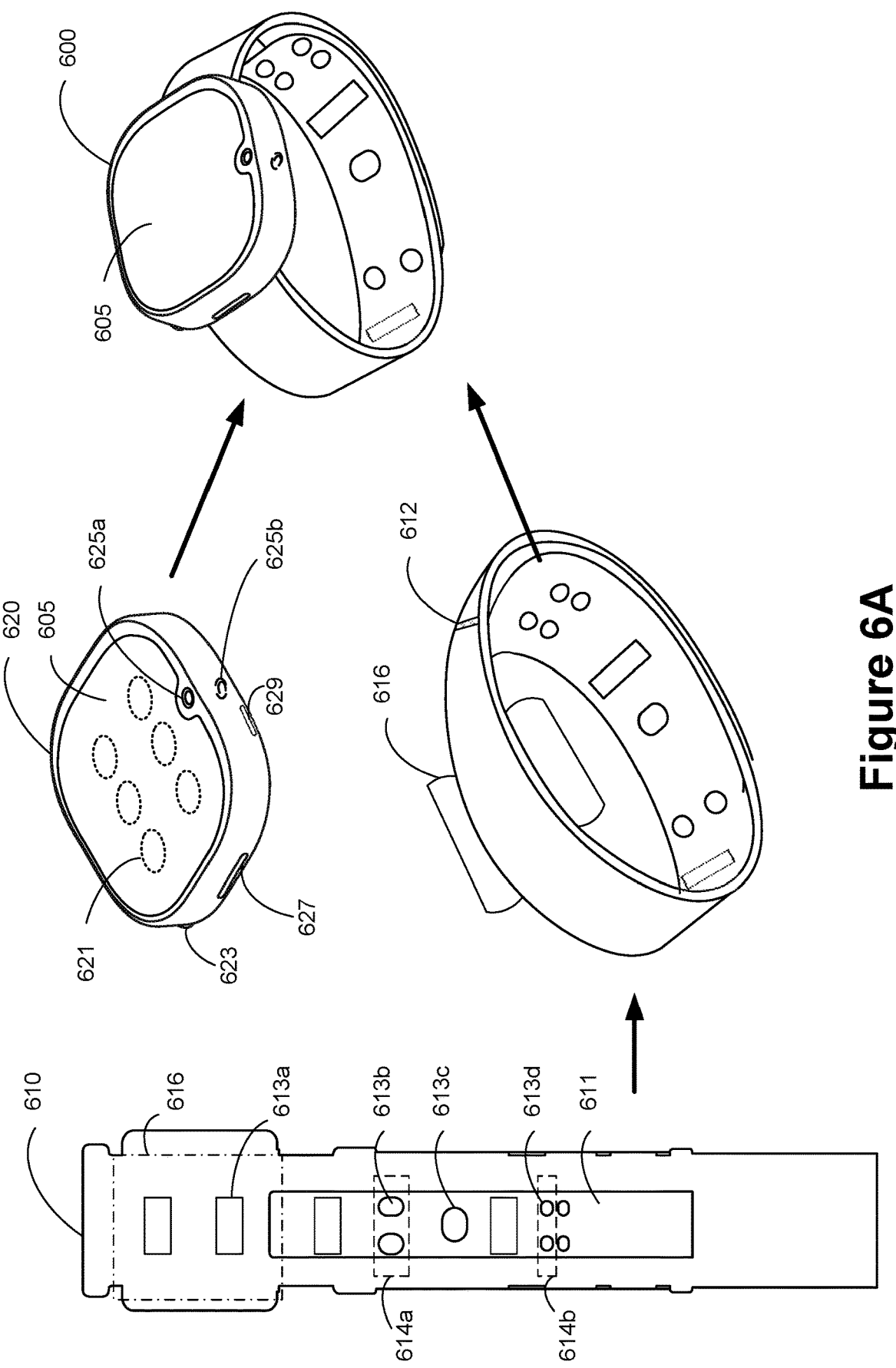
FIGS. 6A-6B illustrate an example wrist-wearable device 600 in accordance with some embodiments.
Figure 6B:
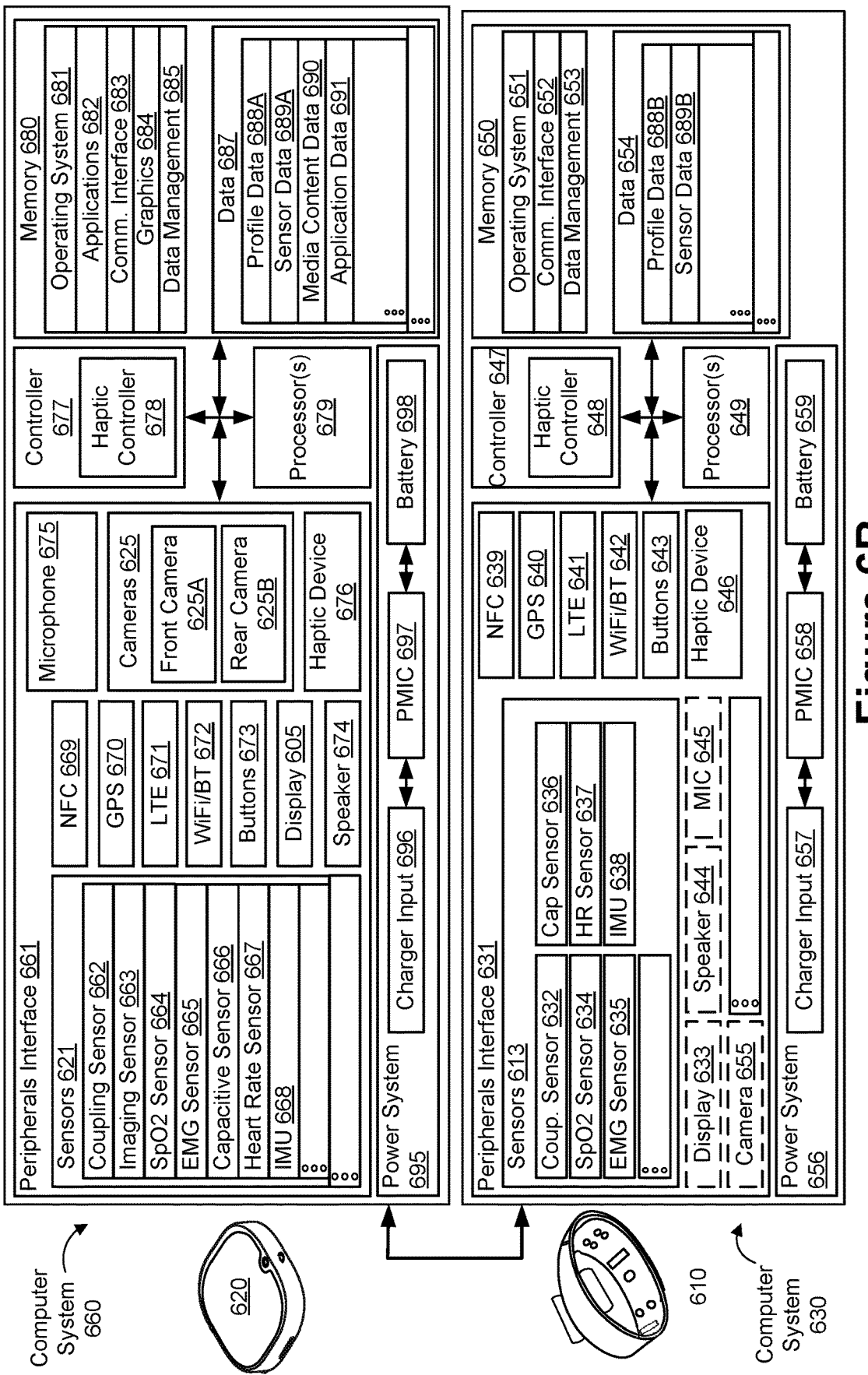

FIGS. 6A and 6B illustrate an example wrist-wearable device 600, in accordance with some embodiments. The wrist-wearable device 600 is an instance of the wrist-wearable device 202 described in reference to FIGS. 2A to 3G herein, such that the wrist-wearable device should be understood to have the features of the wrist-wearable device 600 and vice versa. FIG. 6A illustrates components of the wrist-wearable device 600, which can be used individually or in combination, including combinations that include other electronic devices and/or electronic components.

FIG. 6A shows a wearable band 610 and a watch body 620 (or capsule) being coupled, as discussed below, to form the wrist-wearable device 600. The wrist-wearable device 600 can perform various functions and/or operations associated with navigating through user interfaces and selectively opening applications, as well as the functions and/or operations described above with reference to FIGS. 2A to 3G.

As will be described in more detail below, operations executed by the wrist-wearable device 600 can include (i) presenting content to a user (e.g., displaying visual content via a display 605); (ii) detecting (e.g., sensing) user input (e.g., sensing a touch on peripheral button 623 and/or at a touch screen of the display 605, a hand gesture detected by sensors (e.g., biopotential sensors)); (iii) sensing biometric data via one or more sensors 613 (e.g., neuromuscular signals, heart rate, temperature, or sleep); messaging (e.g., text, speech, or video); image capture via one or more imaging devices or cameras 625; wireless communications (e.g., cellular, near field, Wi-Fi, or personal area network); location determination; financial transactions; providing haptic feedback; alarms; notifications; biometric authentication; health monitoring; and/or sleep monitoring.

The above-example functions can be executed independently in the watch body 620, independently in the wearable band 610, and/or via an electronic communication between the watch body 620 and the wearable band 610. In some embodiments, functions can be executed on the wrist-wearable device 600 while an AR environment is being presented (e.g., via one of the AR systems 500a to 500d). As the skilled artisan will appreciate upon reading the descriptions provided herein, the novel wearable devices described herein can be used with other types of AR environments.

The wearable band 610 can be configured to be worn by a user such that an inner (or inside) surface of the wearable structure 611 of the wearable band 610 is in contact with the user's skin. When worn by a user, sensors 613 contact the user's skin. The sensors 613 can sense biometric data such as a user's heart rate, saturated oxygen level, temperature, sweat level, neuromuscular-signal sensors, or a combination thereof. The sensors 613 can also sense data about a user's environment, including a user's motion, altitude, location, orientation, gait, acceleration, position, or a combination thereof. In some embodiments, the sensors 613 are configured to track a position and/or motion of the wearable band 610. The one or more sensors 613 can include any of the sensors defined above and/or discussed below with respect to FIG. 6B.

The one or more sensors 613 can be distributed on an inside and/or an outside surface of the wearable band 610. In some embodiments, the one or more sensors 613 are uniformly spaced along the wearable band 610. Alternatively, in some embodiments, the one or more sensors 613 are positioned at distinct points along the wearable band 610. As shown in FIG. 6A, the one or more sensors 613 can be the same or distinct. For example, in some embodiments, the one or more sensors 613 can be shaped as a pill (e.g., sensor 613a), an oval, a circle a square, an oblong (e.g., sensor 613c), and/or any other shape that maintains contact with the user's skin (e.g., such that neuromuscular signal and/or other biometric data can be accurately measured at the user's skin). In some embodiments, the one or more sensors 613 are aligned to form pairs of sensors (e.g., for sensing neuromuscular signals based on differential sensing within each respective sensor). For example, sensor 613b is aligned with an adjacent sensor to form sensor pair 614a, and sensor 613d is aligned with an adjacent sensor to form sensor pair 614b. In some embodiments, the wearable band 610 does not have a sensor pair. Alternatively, in some embodiments, the wearable band 610 has a predetermined number of sensor pairs (one pair of sensors, three pairs of sensors, four pairs of sensors, six pairs of sensors, or sixteen pairs of sensors).

The wearable band 610 can include any suitable number of sensors 613. In some embodiments, the amount and arrangements of sensors 613 depend on the particular application for which the wearable band 610 is used. For instance, a wearable band 610 configured as an armband, wristband, or chest-band may include a plurality of sensors 613 with a different number of sensors 613 and different arrangement for each use case, such as medical use cases, compared to gaming or general day-to-day use cases.

In accordance with some embodiments, the wearable band 610 further includes an electrical ground electrode and a shielding electrode. The electrical ground and shielding electrodes, like the sensors 613, can be distributed on the inside surface of the wearable band 610 such that they contact a portion of the user's skin. For example, the electrical ground and shielding electrodes can be at an inside surface of coupling mechanism 616 or an inside surface of a wearable structure 611. The electrical ground and shielding electrodes can be formed and/or use the same components as the sensors 613. In some embodiments, the wearable band 610 includes more than one electrical ground electrode and more than one shielding electrode.

The sensors 613 can be formed as part of the wearable structure 611 of the wearable band 610. In some embodiments, the sensors 613 are flush or substantially flush with the wearable structure 611 such that they do not extend beyond the surface of the wearable structure 611. While flush with the wearable structure 611, the sensors 613 are still configured to contact the user's skin (e.g., via a skin-contacting surface). Alternatively, in some embodiments, the sensors 613 extend beyond the wearable structure 611 a predetermined distance (e.g., 0.1 mm to 2 mm) to make contact and depress into the user's skin. In some embodiments, the sensors 613 are coupled to an actuator (not shown) configured to adjust an extension height (e.g., a distance from the surface of the wearable structure 611) of the sensors 613 such that the sensors 613 make contact and depress into the user's skin. In some embodiments, the actuators adjust the extension height between 0.01 mm to 1.2 mm. This allows the user to customize the positioning of the sensors 613 to improve the overall comfort of the wearable band 610 when worn while still allowing the sensors 613 to contact the user's skin. In some embodiments, the sensors 613 are indistinguishable from the wearable structure 611 when worn by the user.

The wearable structure 611 can be formed of an elastic material, elastomers, etc., configured to be stretched and fitted to be worn by the user. In some embodiments, the wearable structure 611 is a textile or woven fabric. As described above, the sensors 613 can be formed as part of a wearable structure 611. For example, the sensors 613 can be molded into the wearable structure 611 or be integrated into a woven fabric (e.g., the sensors 613 can be sewn into the fabric and mimic the pliability of fabric (e.g., the sensors 613 can be constructed from a series of woven strands of fabric)).

The wearable structure 611 can include flexible electronic connectors that interconnect the sensors 613, the electronic circuitry, and/or other electronic components (described below in reference to FIG. 6B) that are enclosed in the wearable band 610. In some embodiments, the flexible electronic connectors are configured to interconnect the sensors 613, the electronic circuitry, and/or other electronic components of the wearable band 610 with respective sensors and/or other electronic components of another electronic device (e.g., watch body 620). The flexible electronic connectors are configured to move with the wearable structure 611 such that the user adjustment to the wearable structure 611 (e.g., resizing, pulling, or folding) does not stress or strain the electrical coupling of components of the wearable band 610.

As described above, the wearable band 610 is configured to be worn by a user. In particular, the wearable band 610 can be shaped or otherwise manipulated to be worn by a user. For example, the wearable band 610 can be shaped to have a substantially circular shape such that it can be configured to be worn on the user's lower arm or wrist. Alternatively, the wearable band 610 can be shaped to be worn on another body part of the user, such as the user's upper arm (e.g., around a bicep), forearm, chest, legs, etc. The wearable band 610 can include a retaining mechanism 612 (e.g., a buckle or a hook and loop fastener) for securing the wearable band 610 to the user's wrist or other body part. While the wearable band 610 is worn by the user, the sensors 613 sense data (referred to as sensor data) from the user's skin. In particular, the sensors 613 of the wearable band 610 obtain (e.g., sense and record) neuromuscular signals.

The sensed data (e.g., sensed neuromuscular signals) can be used to detect and/or determine the user's intention to perform certain motor actions. In particular, the sensors 613 sense and record neuromuscular signals from the user as the user performs muscular activations (e.g., movements or gestures). The detected and/or determined motor action (e.g., phalange (or digits) movements, wrist movements, hand movements, and/or other muscle intentions) can be used to determine control commands or control information (instructions to perform certain commands after the data is sensed) for causing a computing device to perform one or more input commands. For example, the sensed neuromuscular signals can be used to control certain user interfaces displayed on the display 605 of the wrist-wearable device 600 and/or can be transmitted to a device responsible for rendering an AR environment (e.g., a head-mounted display) to perform an action in an associated AR environment, such as to control the motion of a virtual device displayed to the user. The muscular activations performed by the user can include static gestures, such as placing the user's hand palm down on a table; dynamic gestures, such as grasping a physical or virtual object; and covert gestures that are imperceptible to another person, such as slightly tensing a joint by co-contracting opposing muscles or using submuscular activations. The muscular activations performed by the user can include symbolic gestures (e.g., gestures mapped to other gestures, interactions, or commands, for example, based on a gesture vocabulary that specifies the mapping of gestures to commands).

The sensor data sensed by the sensors 613 can be used to provide a user with an enhanced interaction with a physical object (e.g., devices communicatively coupled with the wearable band 610) and/or a virtual object in an AR application generated by an AR system (e.g., user interface objects presented on the display 605 or another computing device (e.g., a smartphone)).

In some embodiments, the wearable band 610 includes one or more haptic devices 646 (FIG. 6B; e.g., a vibratory haptic actuator) that are configured to provide haptic feedback (e.g., a cutaneous and/or kinesthetic sensation) to the user's skin. The sensors 613 and/or the haptic devices 646 can be configured to operate in conjunction with multiple applications including, without limitation, health monitoring, social media, games, and AR (e.g., the applications associated with AR).

The wearable band 610 can also include a coupling mechanism 616 (e.g., a cradle or a shape of the coupling mechanism can correspond to the shape of the watch body 620 of the wrist-wearable device 600) for detachably coupling a capsule (e.g., a computing unit) or watch body 620 (via a coupling surface of the watch body 620) to the wearable band 610. In particular, the coupling mechanism 616 can be configured to receive a coupling surface proximate to the bottom side of the watch body 620 (e.g., a side opposite to a front side of the watch body 620 where the display 605 is located), such that a user can push the watch body 620 downward into the coupling mechanism 616 to attach the watch body 620 to the coupling mechanism 616. In some embodiments, the coupling mechanism 616 can be configured to receive a top side of the watch body 620 (e.g., a side proximate to the front side of the watch body 620 where the display 605 is located) that is pushed upward into the cradle, as opposed to being pushed downward into the coupling mechanism 616. In some embodiments, the coupling mechanism 616 is an integrated component of the wearable band 610 such that the wearable band 610 and the coupling mechanism 616 are a single unitary structure. In some embodiments, the coupling mechanism 616 is a type of frame or shell that allows the watch body 620 coupling surface to be retained within or on the wearable band 610 coupling mechanism 616 (e.g., a cradle, a tracker band, a support base, or a clasp).

The coupling mechanism 616 can allow for the watch body 620 to be detachably coupled to the wearable band 610 through a friction fit, a magnetic coupling, a rotation-based connector, a shear-pin coupler, a retention spring, one or more magnets, a clip, a pin shaft, a hook-and-loop fastener, or a combination thereof. A user can perform any type of motion to couple the watch body 620 to the wearable band 610 and to decouple the watch body 620 from the wearable band 610. For example, a user can twist, slide, turn, push, pull, or rotate the watch body 620 relative to the wearable band 610, or a combination thereof, to attach the watch body 620 to the wearable band 610 and to detach the watch body 620 from the wearable band 610. Alternatively, as discussed below, in some embodiments, the watch body 620 can be decoupled from the wearable band 610 by actuation of the release mechanism 629.

The wearable band 610 can be coupled with a watch body 620 to increase the functionality of the wearable band 610 (e.g., converting the wearable band 610 into a wrist-wearable device 600, adding an additional computing unit and/or battery to increase computational resources and/or a battery life of the wearable band 610, or adding additional sensors to improve sensed data). As described above, the wearable band 610 (and the coupling mechanism 616) is configured to operate independently (e.g., execute functions independently) from watch body 620. For example, the coupling mechanism 616 can include one or more sensors 613 that contact a user's skin when the wearable band 610 is worn by the user and provide sensor data for determining control commands.

A user can detach the watch body 620 (or capsule) from the wearable band 610 in order to reduce the encumbrance of the wrist-wearable device 600 to the user. For embodiments in which the watch body 620 is removable, the watch body 620 can be referred to as a removable structure, such that in these embodiments the wrist-wearable device 600 includes a wearable portion (e.g., the wearable band 610) and a removable structure (the watch body 620).

Turning to the watch body 620, the watch body 620 can have a substantially rectangular or circular shape. The watch body 620 is configured to be worn by the user on their wrist or on another body part. More specifically, the watch body 620 is sized to be easily carried by the user, attached on a portion of the user's clothing, and/or coupled to the wearable band 610 (forming the wrist-wearable device 600). As described above, the watch body 620 can have a shape corresponding to the coupling mechanism 616 of the wearable band 610. In some embodiments, the watch body 620 includes a single release mechanism 629 or multiple release mechanisms (e.g., two release mechanisms 629 positioned on opposing sides of the watch body 620, such as spring-loaded buttons) for decoupling the watch body 620 and the wearable band 610. The release mechanism 629 can include, without limitation, a button, a knob, a plunger, a handle, a lever, a fastener, a clasp, a dial, a latch, or a combination thereof.

A user can actuate the release mechanism 629 by pushing, turning, lifting, depressing, shifting, or performing other actions on the release mechanism 629. Actuation of the release mechanism 629 can release (e.g., decouple) the watch body 620 from the coupling mechanism 616 of the wearable band 610, allowing the user to use the watch body 620 independently from wearable band 610 and vice versa. For example, decoupling the watch body 620 from the wearable band 610 can allow the user to capture images using rear-facing camera 625b. Although the coupling mechanism 616 is shown positioned at a corner of watch body 620, the release mechanism 629 can be positioned anywhere on watch body 620 that is convenient for the user to actuate. In addition, in some embodiments, the wearable band 610 can also include a respective release mechanism for decoupling the watch body 620 from the coupling mechanism 616. In some embodiments, the release mechanism 629 is optional and the watch body 620 can be decoupled from the coupling mechanism 616, as described above (e.g., via twisting or rotating).

The watch body 620 can include one or more peripheral buttons 623 and 627 for performing various operations at the watch body 620. For example, the peripheral buttons 623 and 627 can be used to turn on or wake (e.g., transition from a sleep state to an active state) the display 605, unlock the watch body 620, increase or decrease volume, increase or decrease brightness, interact with one or more applications, interact with one or more user interfaces. Additionally, or alternatively, in some embodiments, the display 605 operates as a touch screen and allows the user to provide one or more inputs for interacting with the watch body 620.

In some embodiments, the watch body 620 includes one or more sensors 621. The sensors 621 of the watch body 620 can be the same or distinct from the sensors 613 of the wearable band 610. The sensors 621 of the watch body 620 can be distributed on an inside and/or an outside surface of the watch body 620. In some embodiments, the sensors 621 are configured to contact a user's skin when the watch body 620 is worn by the user. For example, the sensors 621 can be placed on the bottom side of the watch body 620 and the coupling mechanism 616 can be a cradle with an opening that allows the bottom side of the watch body 620 to directly contact the user's skin. Alternatively, in some embodiments, the watch body 620 does not include sensors that are configured to contact the user's skin (e.g., including sensors internal and/or external to the watch body 620 that are configured to sense data of the watch body 620 and the watch body 620's surrounding environment). In some embodiments, the sensors 613 are configured to track a position and/or a motion of the watch body 620.

The watch body 620 and the wearable band 610 can share data using a wired communication method (e.g., a Universal Asynchronous Receiver/Transmitter (UART) or a USB transceiver) and/or a wireless communication method (e.g., near-field communication or Bluetooth). For example, the watch body 620 and the wearable band 610 can share data sensed by the sensors 613 and 621, as well as application-and device-specific information (e.g., active and/or available applications), output devices (e.g., display or speakers), and/or input devices (e.g., touch screens, microphones, or imaging sensors).

In some embodiments, the watch body 620 can include, without limitation, a front-facing camera 625a and/or a rear-facing camera 625b, sensors 621 (e.g., a biometric sensor, an IMU sensor, a heart rate sensor, a saturated oxygen sensor, a neuromuscular-signal sensor, an altimeter sensor, a temperature sensor, a bioimpedance sensor, a pedometer sensor, an optical sensor (e.g., FIG. 6B; imaging sensor 663), a touch sensor, a sweat sensor). In some embodiments, the watch body 620 can include one or more haptic devices 676 (FIG. 6B; a vibratory haptic actuator) that is configured to provide haptic feedback (e.g., a cutaneous and/or kinesthetic sensation) to the user. The sensors 621 and/or the haptic device 676 can also be configured to operate in conjunction with multiple applications, including, without limitation, health-monitoring applications, social media applications, game applications, and AR applications (e.g., the applications associated with AR).

As described above, the watch body 620 and the wearable band 610, when coupled, can form the wrist-wearable device 600. When coupled, the watch body 620 and wearable band 610 operate as a single device to execute functions (e.g., operations, detections, or communications) described herein. In some embodiments, each device is provided with particular instructions for performing the one or more operations of the wrist-wearable device 600. For example, in accordance with a determination that the watch body 620 does not include neuromuscular-signal sensors, the wearable band 610 can include alternative instructions for performing associated instructions (e.g., providing sensed neuromuscular-signal data to the watch body 620 via a different electronic device). Operations of the wrist-wearable device 600 can be performed by the watch body 620 alone or in conjunction with the wearable band 610 (e.g., via respective processors and/or hardware components) and vice versa. In some embodiments, operations of the wrist-wearable device 600, the watch body 620, and/or the wearable band 610 can be performed in conjunction with one or more processors and/or hardware components of another communicatively coupled device (e.g., FIGS. 8A-8B; the HIPD 800).

As described below with reference to the block diagram of FIG. 6B, the wearable band 610 and/or the watch body 620 can each include independent resources required to independently execute functions. For example, the wearable band 610 and/or the watch body 620 can each include a power source (e.g., a battery), a memory, data storage, a processor (e.g., a CPU), communications, a light source, and/or input/output devices.

FIG. 6B shows block diagrams of a computing system 630 corresponding to the wearable band 610 and a computing system 660 corresponding to the watch body 620, according to some embodiments. A computing system of the wrist-wearable device 600 includes a combination of components of the wearable band computing system 630 and the watch body computing system 660, in accordance with some embodiments.

The watch body 620 and/or the wearable band 610 can include one or more components shown in watch body computing system 660. In some embodiments, a single integrated circuit includes all or a substantial portion of the components of the watch body computing system 660 that are included in a single integrated circuit. Alternatively, in some embodiments, components of the watch body computing system 660 are included in a plurality of integrated circuits that are communicatively coupled. In some embodiments, the watch body computing system 660 is configured to couple (e.g., via a wired or wireless connection) with the wearable band computing system 630, which allows the computing systems to share components, distribute tasks, and/or perform other operations described herein (individually or as a single device).

The watch body computing system 660 can include one or more processors 679, a controller 677, a peripherals interface 661, a power system 695, and memory (e.g., a memory 680), each of which are defined above and described in more detail below.

The power system 695 can include a charger input 696, a power-management integrated circuit (PMIC) 697, and a battery 698, each of which are defined above. In some embodiments, a watch body 620 and a wearable band 610 can have respective charger inputs (e.g., charger inputs 696 and 657), respective batteries (e.g., batteries 698 and 659), and can share power with each other (e.g., the watch body 620 can power and/or charge the wearable band 610 and vice versa). Although watch body 620 and/or the wearable band 610 can include respective charger inputs, a single charger input can charge both devices when coupled. The watch body 620 and the wearable band 610 can receive a charge using a variety of techniques. In some embodiments, the watch body 620 and the wearable band 610 can use a wired charging assembly (e.g., power cords) to receive the charge. Alternatively, or in addition, the watch body 620 and/or the wearable band 610 can be configured for wireless charging. For example, a portable charging device can be designed to mate with a portion of watch body 620 and/or wearable band 610 and wirelessly deliver usable power to a battery of watch body 620 and/or wearable band 610. The watch body 620 and the wearable band 610 can have independent power systems (e.g., power system 695 and 656) to enable each to operate independently. The watch body 620 and wearable band 610 can also share power (e.g., one can charge the other) via respective PMICs (e.g., PMICs 697 and 658) that can share power over power and ground conductors and/or over wireless charging antennas.

In some embodiments, the peripherals interface 661 can include one or more sensors 621, many of which listed below are defined above. The sensors 621 can include one or more coupling sensors 662 for detecting when the watch body 620 is coupled with another electronic device (e.g., a wearable band 610). The sensors 621 can include imaging sensors 663 (one or more of the cameras 625 and/or separate imaging sensors 663 (e.g., thermal-imaging sensors)). In some embodiments, the sensors 621 include one or more SpO2 sensors 664. In some embodiments, the sensors 621 include one or more biopotential-signal sensors (e.g., EMG sensors 665, which may be disposed on a user-facing portion of the watch body 620 and/or the wearable band 610). In some embodiments, the sensors 621 include one or more capacitive sensors 666. In some embodiments, the sensors 621 include one or more heart rate sensors 667. In some embodiments, the sensors 621 include one or more IMUs 668. In some embodiments, one or more IMUs 668 can be configured to detect movement of a user's hand or other location that the watch body 620 is placed or held.

In some embodiments, the peripherals interface 661 includes an NFC component 669, a GPS component 670, a long-term evolution (LTE) component 671, and/or a Wi-Fi and/or Bluetooth communication component 672. In some embodiments, the peripherals interface 661 includes one or more buttons 673 (e.g., the peripheral buttons 623 and 627 in FIG. 6A), which, when selected by a user, cause operations to be performed at the watch body 620. In some embodiments, the peripherals interface 661 includes one or more indicators, such as a light-emitting diode (LED), to provide a user with visual indicators (e.g., message received, low battery, an active microphone, and/or a camera).

The watch body 620 can include at least one display 605 for displaying visual representations of information or data to the user, including user-interface elements and/or three-dimensional (3D) virtual objects. The display can also include a touch screen for inputting user inputs, such as touch gestures, swipe gestures, and the like. The watch body 620 can include at least one speaker 674 and at least one microphone 675 for providing audio signals to the user and receiving audio input from the user. The user can provide user inputs through the microphone 675 and can also receive audio output from the speaker 674 as part of a haptic event provided by the haptic controller 678. The watch body 620 can include at least one camera 625, including a front-facing camera 625a and a rear-facing camera 625b. The cameras 625 can include ultra-wide-angle cameras, wide-angle cameras, fish-eye cameras, spherical cameras, telephoto cameras, depth-sensing cameras, or other types of cameras.

The watch body computing system 660 can include one or more haptic controllers 678 and associated componentry (e.g., haptic devices 676) for providing haptic events at the watch body 620 (e.g., a vibrating sensation or audio output in response to an event at the watch body 620). The haptic controllers 678 can communicate with one or more haptic devices 676, such as electroacoustic devices, including a speaker of the one or more speakers 674 and/or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). The haptic controller 678 can provide haptic events to respective haptic actuators that are capable of being sensed by a user of the watch body 620. In some embodiments, the one or more haptic controllers 678 can receive input signals from an application of the applications 682.

In some embodiments, the computer system 630 and/or the computer system 660 can include memory 680, which can be controlled by a memory controller of the one or more controllers 677 and/or one or more processors 679. In some embodiments, software components stored in the memory 680 include one or more applications 682 configured to perform operations at the watch body 620. In some embodiments, the one or more applications 682 include games, word processors, messaging applications, calling applications, web browsers, social media applications, media streaming applications, financial applications, calendars, clocks, etc. In some embodiments, software components stored in the memory 680 include one or more communication interface modules 683 as defined above. In some embodiments, software components stored in the memory

680 include one or more graphics modules 684 for rendering, encoding, and/or decoding audio and/or visual data; and one or more data management modules 685 for collecting, organizing, and/or providing access to the data 687 stored in memory 680. In some embodiments, one or more of applications 682 and/or one or more modules can work in conjunction with one another to perform various tasks at the watch body 620.

In some embodiments, software components stored in the memory 680 can include one or more operating systems 681 (e.g., a Linux-based operating system, an Android operating system, etc.). The memory 680 can also include data 687. The data 687 can include profile data 688A, sensor data 689A, media content data 690, and application data 691.

It should be appreciated that the watch body computing system 660 is an example of a computing system within the watch body 620, and that the watch body 620 can have more or fewer components than shown in the watch body computing system 660, combine two or more components, and/or have a different configuration and/or arrangement of the components. The various components shown in watch body computing system 660 are implemented in hardware, software, firmware, or a combination thereof, including one or more signal processing and/or application-specific integrated circuits.

Turning to the wearable band computing system 630, one or more components that can be included in the wearable band 610 are shown. The wearable band computing system 630 can include more or fewer components than shown in the watch body computing system 660, combine two or more components, and/or have a different configuration and/or arrangement of some or all of the components. In some embodiments, all, or a substantial portion of the components of the wearable band computing system 630 are included in a single integrated circuit. Alternatively, in some embodiments, components of the wearable band computing system 630 are included in a plurality of integrated circuits that are communicatively coupled. As described above, in some embodiments, the wearable band computing system 630 is configured to couple (e.g., via a wired or wireless connection) with the watch body computing system 660, which allows the computing systems to share components, distribute tasks, and/or perform other operations described herein (individually or as a single device).

The wearable band computing system 630, similar to the watch body computing system 660, can include one or more processors 649, one or more controllers 647 (including one or more haptics controller 648), a peripherals interface 631 that can include one or more sensors 613 and other peripheral devices, power source (e.g., a power system 656), and memory (e.g., a memory 650) that includes an operating system (e.g., an operating system 651), data (e.g., data 654 including profile data 688B, sensor data 689B, etc.), and one or more modules (e.g., a communications interface module 652, a data management module 653, etc.).

The one or more sensors 613 can be analogous to sensors 621 of the computer system 660 in light of the definitions above. For example, sensors 613 can include one or more coupling sensors 632, one or more SpO2 sensors 634, one or more EMG sensors 635, one or more capacitive sensors 636, one or more heart rate sensors 637, and one or more IMU sensors 638.

The peripherals interface 631 can also include other components analogous to those included in the peripheral interface 661 of the computer system 660, including an NFC component 639, a GPS component 640, an LTE component 641, a Wi-Fi and/or Bluetooth communication component

642, and/or one or more haptic devices 676 as described above in reference to peripherals interface 661. In some embodiments, the peripherals interface 631 includes one or more buttons 643, a display 633, a speaker 644, a microphone 645, and a camera 655. In some embodiments, the peripherals interface 631 includes one or more indicators, such as an LED.

It should be appreciated that the wearable band computing system 630 is an example of a computing system within the wearable band 610, and that the wearable band 610 can have more or fewer components than shown in the wearable band computing system 630, combine two or more components, and/or have a different configuration and/or arrangement of the components. The various components shown in wearable band computing system 630 can be implemented in one or a combination of hardware, software, and firmware, including one or more signal processing and/or application-specific integrated circuits.

The wrist-wearable device 600 with respect to FIG. 6A is an example of the wearable band 610 and the watch body 620 coupled, so the wrist-wearable device 600 will be understood to include the components shown and described for the wearable band computing system 630 and the watch body computing system 660. In some embodiments, wrist-wearable device 600 has a split architecture (e.g., a split mechanical architecture or a split electrical architecture) between the watch body 620 and the wearable band 610. In other words, all of the components shown in the wearable band computing system 630 and the watch body computing system 660 can be housed or otherwise disposed in a combined wrist-wearable device 600, or within individual components of the watch body 620, wearable band 610, and/or portions thereof (e.g., a coupling mechanism 616 of the wearable band 610).

The techniques described above can be used with any device for sensing neuromuscular signals, including the arm-wearable devices of FIG. 6A-6B, but could also be used with other types of wearable devices for sensing neuromuscular signals (such as body-wearable or head-wearable devices that might have neuromuscular sensors closer to the brain or spinal column).

In some embodiments, a wrist-wearable device 600 can be used in conjunction with a head-wearable device described below (e.g., AR device 700 and VR device 710) and/or an HIPD 800, and the wrist-wearable device 600 can also be configured to be used to allow a user to control aspect of the artificial reality (e.g., by using EMG-based gestures to control user interface objects in the artificial reality and/or by allowing a user to interact with the touchscreen on the wrist-wearable device to also control aspects of the artificial reality). In some embodiments, a wrist-wearable device 600 can also be used in conjunction with a wearable garment, such as smart textile-based garment 900 described below in reference to FIGS. 9A-9C. Having thus described example wrist-wearable device, attention will now be turned to example head-wearable devices, such AR device 700 and VR device 710.

Example Head-Wearable Devices

FIGS. 7A, 7B-1, 7B-2, and 7C show example head-wearable devices, in accordance with some embodiments. Head-wearable devices can include, but are not limited to, AR devices 700 (e.g., AR or smart eyewear devices, such as smart glasses, smart monocles, smart contacts, etc.), VR devices 710 (e.g., VR headsets or head-mounted displays (HMDs)), or other ocularly coupled devices. The AR devices 700 and the VR devices 710 are instances of the head-wearable device 102 described in reference to FIGS. 1A to 3G herein, such that the head-wearable device should be understood to have the features of the AR devices 700 and/or the VR devices 710 and vice versa. The AR devices 700 and the VR devices 710 can perform various functions and/or operations associated with navigating through user interfaces and selectively opening applications, as well as the functions and/or operations described above with reference to FIGS. 1A to 3G.

Figure 7A:
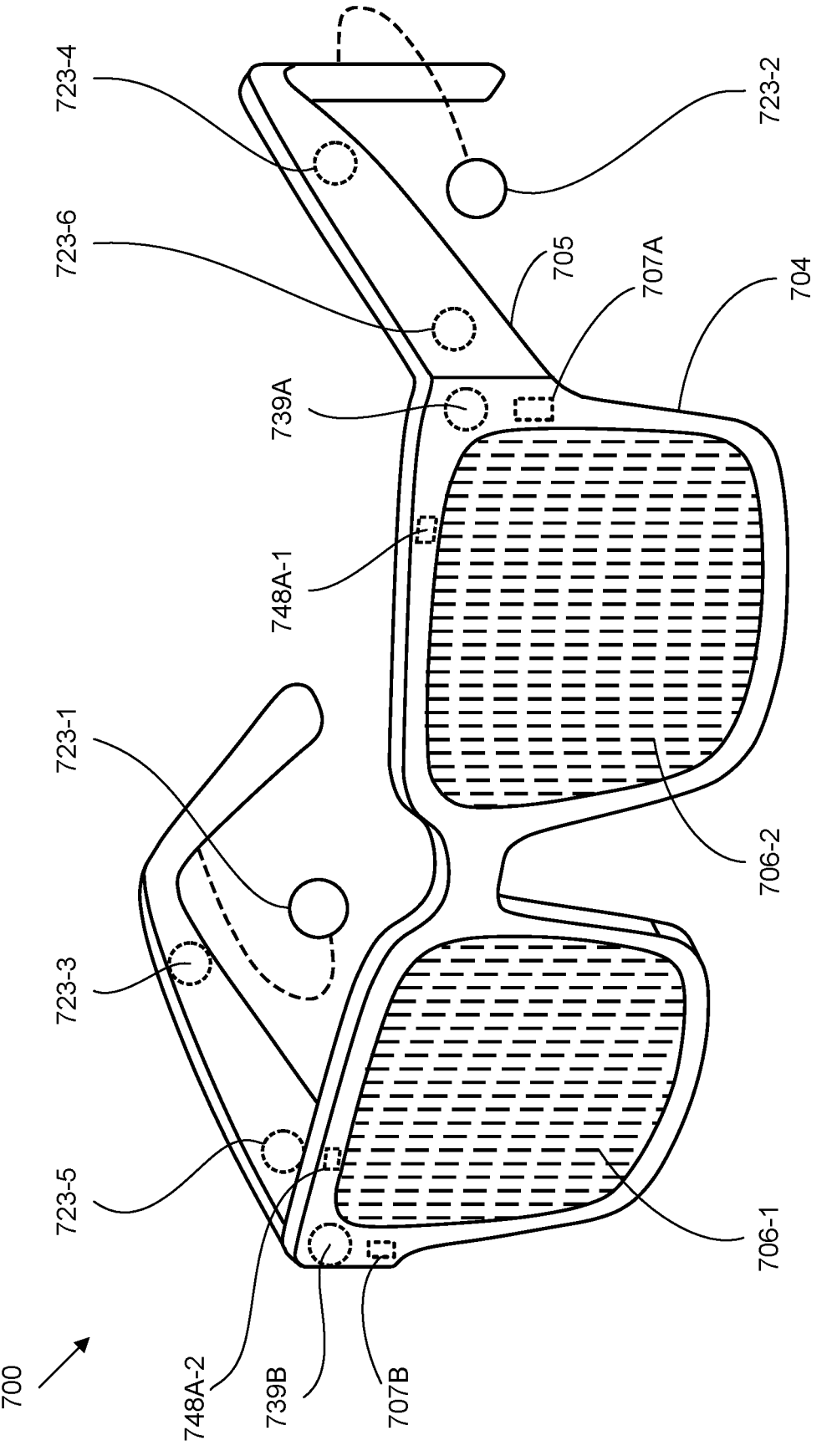
Figures 1, 7B:
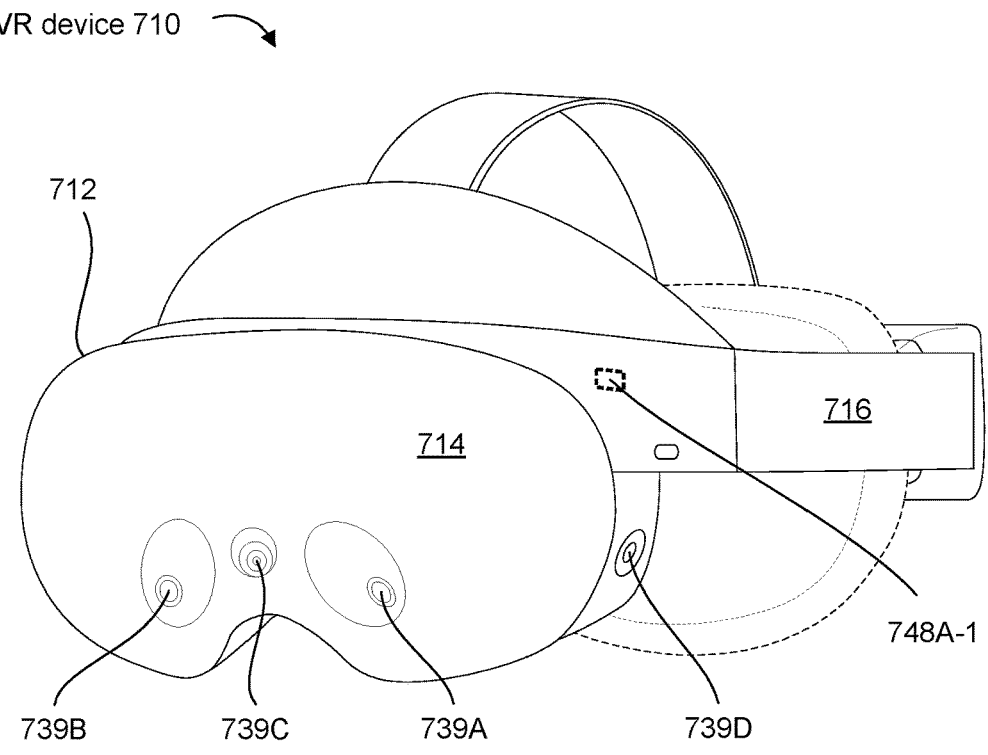
Figures 2, 7B:
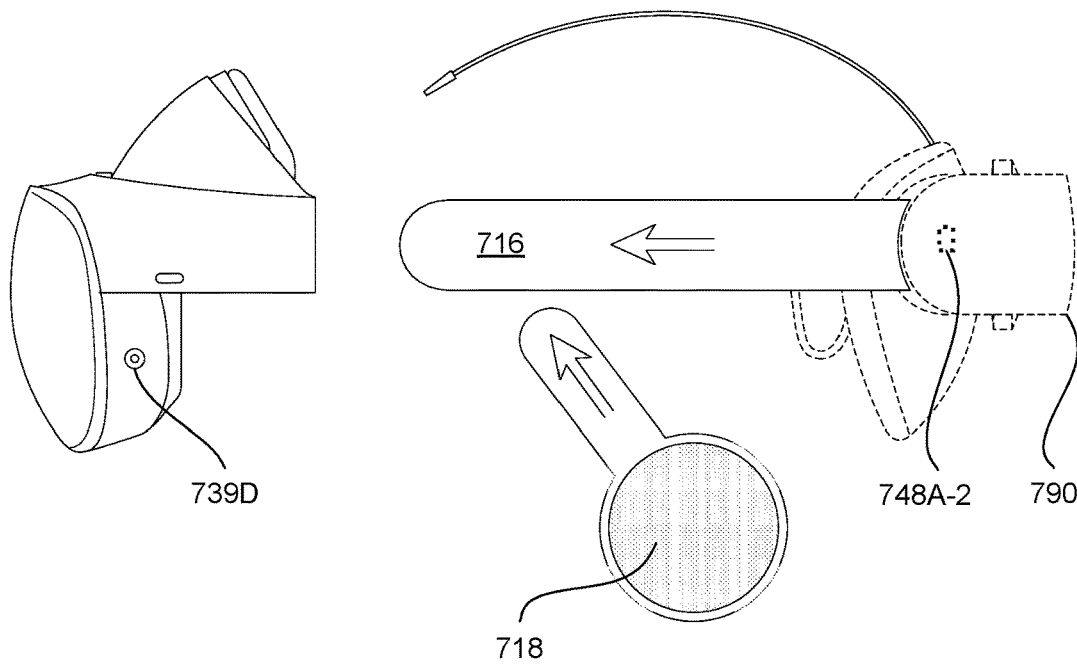

In some embodiments, an AR system (e.g., FIGS. 5A-5D-2; AR systems 500a-500d) includes an AR device 700 (as shown in FIG. 7A) and/or VR device 710 (as shown in FIGS. 7B-1-B-2). In some embodiments, the AR device 700 and the VR device 710 can include one or more analogous components (e.g., components for presenting interactive AR environments, such as processors, memory, and/or presentation devices, including one or more displays and/or one or more waveguides), some of which are described in more detail with respect to FIG. 7C. The head-wearable devices can use display projectors (e.g., display projector assemblies 707A and 707B) and/or waveguides for projecting representations of data to a user. Some embodiments of head-wearable devices do not include displays.

FIG. 7A shows an example visual depiction of the AR device 700 (e.g., which may also be described herein as augmented-reality glasses and/or smart glasses). The AR device 700 can work in conjunction with additional electronic components that are not shown in FIGS. 7A, such as a wearable accessory device and/or an intermediary processing device, in electronic communication or otherwise configured to be used in conjunction with the AR device 700. In some embodiments, the wearable accessory device and/or the intermediary processing device may be configured to couple with the AR device 700 via a coupling mechanism in electronic communication with a coupling sensor 724, where the coupling sensor 724 can detect when an electronic device becomes physically or electronically coupled with the AR device 700. In some embodiments, the AR device 700 can be configured to couple to a housing (e.g., a portion of frame 704 or temple arms 705), which may include one or more additional coupling mechanisms configured to couple with additional accessory devices. The components shown in FIG. 7A can be implemented in hardware, software, firmware, or a combination thereof, including one or more signal-processing components and/or application-specific integrated circuits (ASICs).

The AR device 700 includes mechanical glasses components, including a frame 704 configured to hold one or more lenses (e.g., one or both lenses 706-1 and 706-2). One of ordinary skill in the art will appreciate that the AR device 700 can include additional mechanical components, such as hinges configured to allow portions of the frame 704 of the AR device 700 to be folded and unfolded, a bridge configured to span the gap between the lenses 706-1 and 706-2 and rest on the user's nose, nose pads configured to rest on the bridge of the nose and provide support for the AR device 700, earpieces configured to rest on the user's ears and provide additional support for the AR device 700, temple arms 705 configured to extend from the hinges to the earpieces of the AR device 700, and the like. One of ordinary skill in the art will further appreciate that some examples of the AR device 700 can include none of the mechanical components described herein. For example, smart contact lenses configured to present AR to users may not include any components of the AR device 700.

The lenses 706-1 and 706-2 can be individual displays or display devices (e.g., a waveguide for projected representations). The lenses 706-1 and 706-2 may act together or independently to present an image or series of images to a user. In some embodiments, the lenses 706-1 and 706-2 can operate in conjunction with one or more display projector assemblies 707A and 707B to present image data to a user. While the AR device 700 includes two displays, embodiments of this disclosure may be implemented in AR devices with a single near-eye display (NED) or more than two NEDs.

The AR device 700 includes electronic components, many of which will be described in more detail below with respect to FIG. 7C. Some example electronic components are illustrated in FIG. 7A, including sensors 723-1, 723-2, 723-3, 723-4, 723-5, and 723-6, which can be distributed along a substantial portion of the frame 704 of the AR device 700. The different types of sensors are described below in reference to FIG. 7C. The AR device 700 also includes a left camera 739A and a right camera 739B, which are located on different sides of the frame 704. And the eyewear device includes one or more processors 748A and 748B (e.g., an integral microprocessor, such as an ASIC) that is embedded into a portion of the frame 704.

FIGS. 7B-1 and 7B-2 show an example visual depiction of the VR device 710 (e.g., a head-mounted display (HMD) 712, also referred to herein as an AR headset, a head-wearable device, or a VR headset). The HMD 712 includes a front body 714 and a frame 716 (e.g., a strap or band) shaped to fit around a user's head. In some embodiments, the front body 714 and/or the frame 716 includes one or more electronic elements for facilitating presentation of and/or interactions with an AR and/or VR system (e.g., displays, processors (e.g., processor 748A-1), IMUs, tracking emitters or detectors, or sensors). In some embodiments, the HMD 712 includes output audio transducers (e.g., an audio transducer 718-1), as shown in FIG. 7B-2. In some embodiments, one or more components, such as the output audio transducer(s) 718 and the frame 716, can be configured to attach and detach (e.g., are detachably attachable) to the HMD 712 (e.g., a portion or all of the frame 716 and/or the output audio transducer 718), as shown in FIG. 7B-2. In some embodiments, coupling a detachable component to the HMD 712 causes the detachable component to come into electronic communication with the HMD 712. The VR device 710 includes electronic components, many of which will be described in more detail below with respect to FIG. 7C.

FIGS. 7B-1 and 7B-2 also show that the VR device 710 having one or more cameras, such as the left camera 739A and the right camera 739B, which can be analogous to the left and right cameras on the frame 704 of the AR device 700. In some embodiments, the VR device 710 includes one or more additional cameras (e.g., cameras 739C and 739D), which can be configured to augment image data obtained by the cameras 739A and 739B by providing more information. For example, the camera 739C can be used to supply color information that is not discerned by cameras 739A and 739B. In some embodiments, one or more of the cameras 739A to 739D can include an optional IR (infrared) cut filter configured to remove IR light from being received at the respective camera sensors.

The VR device 710 can include a housing 790 storing one or more components of the VR device 710 and/or additional components of the VR device 710. The housing 790 can be a modular electronic device configured to couple with the VR device 710 (or an AR device 700) and supplement and/or extend the capabilities of the VR device 710 (or an AR device 700). For example, the housing 790 can include additional sensors, cameras, power sources, and processors (e.g., processor 748A-2). to improve and/or increase the functionality of the VR device 710. Examples of the different components included in the housing 790 are described below in reference to FIG. 7C.

Alternatively, or in addition, in some embodiments, the head-wearable device, such as the VR device 710 and/or the AR device 700, includes, or is communicatively coupled to, another external device (e.g., a paired device), such as an HIPD 800 (discussed below in reference to FIGS. 8A-8B) and/or an optional neckband. The optional neckband can couple to the head-wearable device via one or more connectors (e.g., wired or wireless connectors). The head-wearable device and the neckband can operate independently without any wired or wireless connection between them. In some embodiments, the components of the head-wearable device and the neckband are located on one or more additional peripheral devices paired with the head-wearable device, the neckband, or some combination thereof. Furthermore, the neckband is intended to represent any suitable type or form of paired device. Thus, the following discussion of neckbands may also apply to various other paired devices, such as smartwatches, smartphones, wrist bands, other wearable devices, hand-held controllers, tablet computers, or laptop computers.

In some situations, pairing external devices, such as an intermediary processing device (e.g., an HIPD device 800, an optional neckband, and/or a wearable accessory device) with the head-wearable devices (e.g., an AR device 700 and/or a VR device 710) enables the head-wearable devices to achieve a similar form factor of a pair of glasses while still providing sufficient battery and computational power for expanded capabilities. Some, or all, of the battery power, computational resources, and/or additional features of the head-wearable devices can be provided by a paired device or shared between a paired device and the head-wearable devices, thus reducing the weight, heat profile, and form factor of the head-wearable device overall while allowing the head-wearable device to retain its desired functionality. For example, the intermediary processing device (e.g., the HIPD 800) can allow components that would otherwise be included in a head-wearable device to be included in the intermediary processing device (and/or a wearable device or accessory device), thereby shifting a weight load from the user's head and neck to one or more other portions of the user's body. In some embodiments, the intermediary processing device has a larger surface area over which to diffuse and disperse heat to the ambient environment. Thus, the intermediary processing device can allow for greater battery and computational capacity than might otherwise have been possible on the head-wearable devices, standing alone. Because weight carried in the intermediary processing device can be less invasive to a user than weight carried in the head-wearable devices, a user may tolerate wearing a lighter eyewear device and carrying or wearing the paired device for greater lengths of time than the user would tolerate wearing a heavier eyewear device standing alone, thereby enabling an AR environment to be incorporated more fully into a user's day-to-day activities.

In some embodiments, the intermediary processing device is communicatively coupled with the head-wearable device and/or to other devices. The other devices may provide certain functions (e.g., tracking, localizing, depth mapping, processing, and/or storage) to the head-wearable device. In some embodiments, the intermediary processing device includes a controller and a power source. In some embodiments, sensors of the intermediary processing device are configured to sense additional data that can be shared with the head-wearable devices in an electronic format (analog or digital).

The controller of the intermediary processing device processes information generated by the sensors on the intermediary processing device and/or the head-wearable devices. The intermediary processing device, such as an HIPD 800, can process information generated by one or more of its sensors and/or information provided by other communicatively coupled devices. For example, a head-wearable device can include an IMU, and the intermediary processing device (a neckband and/or an HIPD 800) can compute all inertial and spatial calculations from the IMUs located on the head-wearable device. Additional examples of processing performed by a communicatively coupled device, such as the HIPD 800, are provided below in reference to FIGS. 8A and 8B.

AR systems may include a variety of types of visual feedback mechanisms. For example, display devices in the AR devices 700 and/or the VR devices 710 may include one or more liquid-crystal displays (LCDs), light emitting diode (LED) displays, organic LED (OLED) displays, and/or any other suitable type of display screen. AR systems may include a single display screen for both eyes or may provide a display screen for each eye, which may allow for additional flexibility for varifocal adjustments or for correcting a refractive error associated with the user's vision. Some AR systems also include optical subsystems having one or more lenses (e.g., conventional concave or convex lenses, Fresnel lenses, or adjustable liquid lenses) through which a user may view a display screen. In addition to or instead of using display screens, some AR systems include one or more projection systems. For example, display devices in the AR device 700 and/or the VR device 710 may include micro-LED projectors that project light (e.g., using a waveguide) into display devices, such as clear combiner lenses that allow ambient light to pass through. The display devices may refract the projected light toward a user's pupil and may enable a user to simultaneously view both AR content and the real world. AR systems may also be configured with any other suitable type or form of image projection system. As noted, some AR systems may instead of blending an artificial reality with actual reality, substantially replace one or more of a user's sensory perceptions of the real world with a virtual experience.

While the example head-wearable devices are respectively described herein as the AR device 700 and the VR device 710, either or both of the example head-wearable devices described herein can be configured to present fully immersive VR scenes presented in substantially all of a user's field of view, additionally or alternatively to, subtler augmented-reality scenes that are presented within a portion, less than all, of the user's field of view.

In some embodiments, the AR device 700 and/or the VR device 710 can include haptic feedback systems. The haptic feedback systems may provide various types of cutaneous feedback, including vibration, force, traction, shear, texture, and/or temperature. The haptic feedback systems may also provide various types of kinesthetic feedback, such as motion and compliance. The haptic feedback can be implemented using motors, piezoelectric actuators, fluidic systems, and/or a variety of other types of feedback mechanisms. The haptic feedback systems may be implemented independently of other AR devices, within other AR devices, and/or in conjunction with other AR devices (e.g., wrist-wearable devices that may be incorporated into headwear, gloves, body suits, handheld controllers, environmental devices (e.g., chairs or floormats), and/or any other type of device or system, such as a wrist-wearable device 600, an HIPD 800, smart textile-based garment 900), and/or other devices described herein.

Figure 7C:
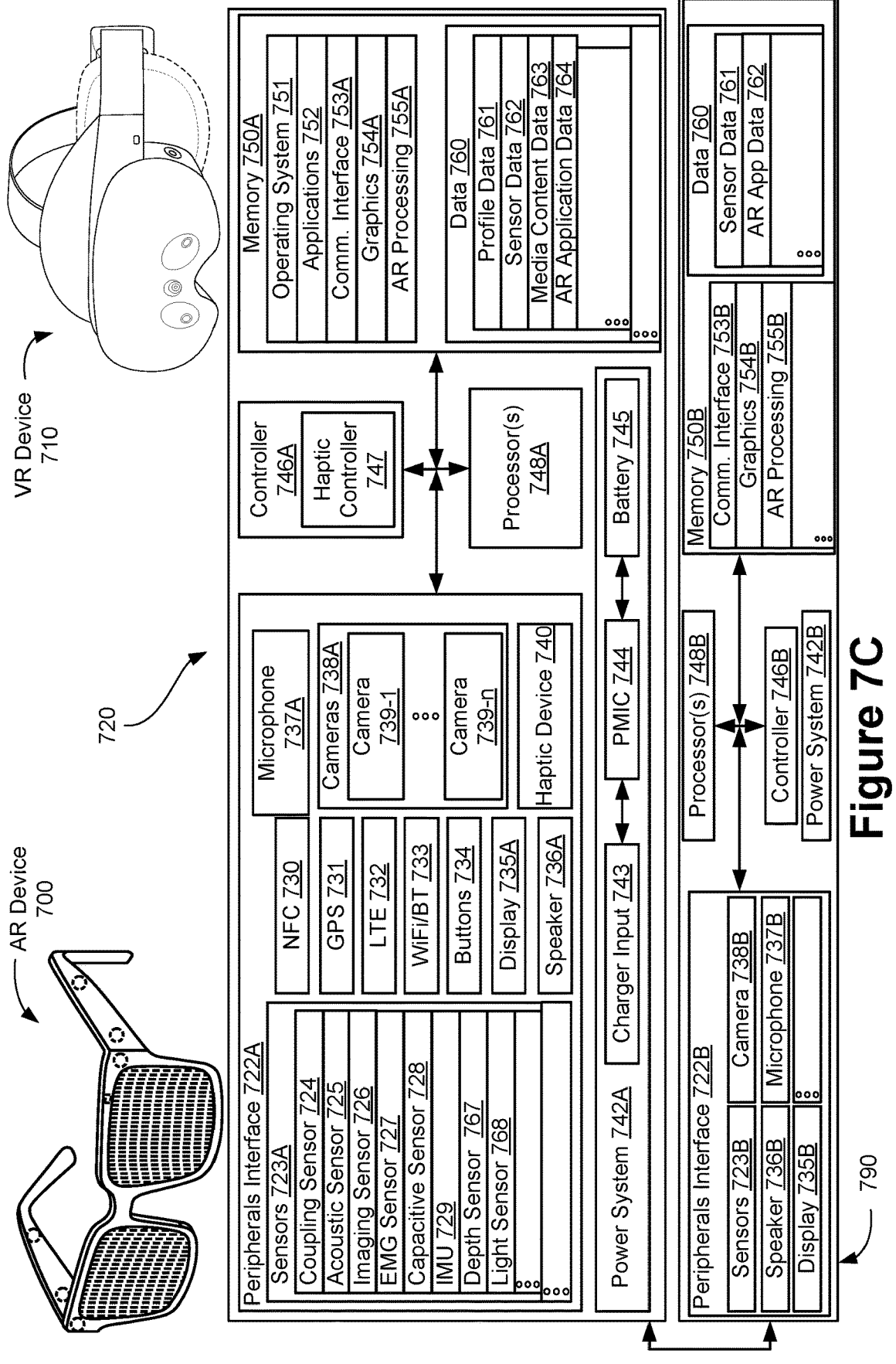

FIG. 7C illustrates a computing system 720 and an optional housing 790, each of which shows components that can be included in a head-wearable device (e.g., the AR device 700 and/or the VR device 710). In some embodiments, more or fewer components can be included in the optional housing 790 depending on practical restraints of the respective head-wearable device being described. Additionally, or alternatively, the optional housing 790 can include additional components to expand and/or augment the functionality of a head-wearable device.

In some embodiments, the computing system 720 and/or the optional housing 790 can include one or more peripheral interfaces 722A and 722B, one or more power systems 742A and 742B (including charger input 743, PMIC 744, and battery 745), one or more controllers 746A and 746B (including one or more haptic controllers 747), one or more processors 748A and 748B (as defined above, including any of the examples provided), and memory 750A and 750B, which can all be in electronic communication with each other. For example, the one or more processors 748A and/or 748B can be configured to execute instructions stored in the memory 750A and/or 750B, which can cause a controller of the one or more controllers 746A and/or 746B to cause operations to be performed at one or more peripheral devices of the peripherals interfaces 722A and/or 722B. In some embodiments, each operation described can occur based on electrical power provided by the power system 742A and/or 742B.

In some embodiments, the peripherals interface 722A can include one or more devices configured to be part of the computing system 720, many of which have been defined above and/or described with respect to wrist-wearable devices shown in FIGS. 6A and 6B. For example, the peripherals interface can include one or more sensors 723A. Some example sensors include one or more coupling sensors 724, one or more acoustic sensors 725, one or more imaging sensors 726, one or more EMG sensors 727, one or more capacitive sensors 728, and/or one or more IMUs 729. In some embodiments, the sensors 723A further include depth sensors 767, light sensors 768, and/or any other types of sensors defined above or described with respect to any other embodiments discussed herein.

In some embodiments, the peripherals interface can include one or more additional peripheral devices, including one or more NFC devices 730, one or more GPS devices 731, one or more LTE devices 732, one or more Wi-Fi and/or Bluetooth devices 733, one or more buttons 734 (e.g., including buttons that are slidable or otherwise adjustable), one or more displays 735A, one or more speakers 736A, one or more microphones 737A, one or more cameras 738A (e.g., including the first camera 739-1 through nth camera 739-n, which are analogous to the left camera 739A and/or the right camera 739B), one or more haptic devices 740, and/or any other types of peripheral devices defined above or described with respect to any other embodiments discussed herein.

The head-wearable devices can include a variety of types of visual feedback mechanisms (e.g., presentation devices). For example, display devices in the AR device 700 and/or the VR device 710 can include one or more liquid-crystal displays (LCDs), light emitting diode (LED) displays, organic LED (OLED) displays, micro-LEDs, and/or any other suitable types of display screens. The head-wearable devices can include a single display screen (e.g., configured to be seen by both eyes) and/or can provide separate display screens for each eye, which can allow for additional flexibility for varifocal adjustments and/or for correcting a refractive error associated with the user's vision. Some embodiments of the head-wearable devices also include optical subsystems having one or more lenses (e.g., conventional concave or convex lenses, Fresnel lenses, or adjustable liquid lenses) through which a user can view a display screen. For example, respective displays 735A can be coupled to each of the lenses 706-1 and 706-2 of the AR device 700. The displays 735A coupled to each of the lenses 706-1 and 706-2 can act together or independently to present an image or series of images to a user. In some embodiments, the AR device 700 and/or the VR device 710 includes a single display 735A (e.g., a near-eye display) or more than two displays 735A.

In some embodiments, a first set of one or more displays 735A can be used to present an augmented-reality environment, and a second set of one or more display devices 735A can be used to present a VR environment. In some embodiments, one or more waveguides are used in conjunction with presenting AR content to the user of the AR device 700 and/or the VR device 710 (e.g., as a means of delivering light from a display projector assembly and/or one or more displays 735A to the user's eyes). In some embodiments, one or more waveguides are fully or partially integrated into the AR device 700 and/or the VR device 710. Additionally, or alternatively, to display screens, some AR systems include one or more projection systems. For example, display devices in the AR device 700 and/or the VR device 710 can include micro-LED projectors that project light (e.g., using a waveguide) into display devices, such as clear combiner lenses that allow ambient light to pass through. The display devices can refract the projected light toward a user's pupil and can enable a user to simultaneously view both AR content and the real world. The head-wearable devices can also be configured with any other suitable type or form of image projection system. In some embodiments, one or more waveguides are provided, additionally or alternatively, to the one or more display(s) 735A.

In some embodiments of the head-wearable devices, ambient light and/or a real-world live view (e.g., a live feed of the surrounding environment that a user would normally see) can be passed through a display element of a respective head-wearable device presenting aspects of the AR system. In some embodiments, ambient light and/or the real-world live view can be passed through a portion, less than all, of an AR environment presented within a user's field of view (e.g., a portion of the AR environment co-located with a physical object in the user's real-world environment that is within a designated boundary (e.g., a guardian boundary) configured to be used by the user while they are interacting with the AR environment). For example, a visual user interface element (e.g., a notification user interface element) can be presented at the head-wearable devices, and an amount of ambient light and/or the real-world live view (e.g., 15%-50% of the ambient light and/or the real-world live view) can be passed through the user interface element, such that the user can distinguish at least a portion of the physical environment over which the user interface element is being displayed.

The head-wearable devices can include one or more external displays 735A for presenting information to users. For example, an external display 735A can be used to show a current battery level, network activity (e.g., connected, disconnected), current activity (e.g., playing a game, in a call, in a meeting, or watching a movie), and/or other relevant information. In some embodiments, the external displays 735A can be used to communicate with others. For example, a user of the head-wearable device can cause the external displays 735A to present a "do not disturb" notification. The external displays 735A can also be used by the user to share any information captured by the one or more components of the peripherals interface 722A and/or generated by the head-wearable device (e.g., during operation and/or performance of one or more applications).

The memory 750A can include instructions and/or data executable by one or more processors 748A (and/or processors 748B of the housing 790) and/or a memory controller of the one or more controllers 746A (and/or controller 746B of the housing 790). The memory 750A can include one or more operating systems 751, one or more applications 752, one or more communication interface modules 753A, one or more graphics modules 754A, one or more AR processing modules 755A, and/or any other types of modules or components defined above or described with respect to any other embodiments discussed herein.

The data 760 stored in memory 750A can be used in conjunction with one or more of the applications and/or programs discussed above. The data 760 can include profile data 761, sensor data 762, media content data 763, AR application data 764, and/or any other types of data defined above or described with respect to any other embodiments discussed herein.

In some embodiments, the controller 746A of the head-wearable devices processes information generated by the sensors 723A on the head-wearable devices and/or another component of the head-wearable devices and/or communicatively coupled with the head-wearable devices (e.g., components of the housing 790, such as components of peripherals interface 722B). For example, the controller 746A can process information from the acoustic sensors 725 and/or image sensors 726. For each detected sound, the controller 746A can perform a direction of arrival (DOA) estimation to estimate a direction from which the detected sound arrived at a head-wearable device. As one or more of the acoustic sensors 725 detect sounds, the controller 746A can populate an audio data set with the information (e.g., represented by sensor data 762).

In some embodiments, a physical electronic connector can convey information between the head-wearable devices and another electronic device, and/or between one or more processors 748A of the head-wearable devices and the controller 746A. The information can be in the form of optical data, electrical data, wireless data, or any other transmittable data form. Moving the processing of information generated by the head-wearable devices to an intermediary processing device can reduce weight and heat in the eyewear device, making it more comfortable and safer for a user. In some embodiments, an optional accessory device (e.g., an electronic neckband or an HIPD 800) is coupled to the head-wearable devices via one or more connectors. The connectors can be wired or wireless connectors and can include electrical and/or non-electrical (e.g., structural) components. In some embodiments, the head-wearable devices and the accessory device can operate independently without any wired or wireless connection between them.

The head-wearable devices can include various types of computer vision components and subsystems. For example, the AR device 700 and/or the VR device 710 can include one or more optical sensors such as two-dimensional (2D) or three-dimensional (3D) cameras, ToF depth sensors, single-beam or sweeping laser rangefinders, 3D LiDAR sensors, and/or any other suitable type or form of optical sensor. A head-wearable device can process data from one or more of these sensors to identify a location of a user and/or aspects of the user's real-world physical surroundings, including the locations of real-world objects within the real-world physical surroundings. In some embodiments, the methods described herein are used to map the real world, to provide a user with context about real-world surroundings, and/or to generate interactable virtual objects (which can be replicas or digital twins of real-world objects that can be interacted with an AR environment), among a variety of other functions. For example, FIGS. 7B-1 and 7B-2 show the VR device 710 having cameras 739A-739D, which can be used to provide depth information for creating a voxel field and a 2D mesh to provide object information to the user to avoid collisions.

The optional housing 790 can include analogous components to those describe above with respect to the computing system 720. For example, the optional housing 790 can include a respective peripherals interface 722B, including more or fewer components to those described above with respect to the peripherals interface 722A. As described above, the components of the optional housing 790 can be used to augment and/or expand on the functionality of the head-wearable devices. For example, the optional housing 790 can include respective sensors 723B, speakers 736B, displays 735B, microphones 737B, cameras 738B, and/or other components to capture and/or present data. Similarly, the optional housing 790 can include one or more processors 748B, controllers 746B, and/or memory 750B (including respective communication interface modules 753B, one or more graphics modules 754B, one or more AR processing modules 755B) that can be used individually and/or in conjunction with the components of the computing system 720.

The techniques described above in FIGS. 7A-7C can be used with different head-wearable devices. In some embodiments, the head-wearable devices (e.g., the AR device 700 and/or the VR device 710) can be used in conjunction with one or more wearable devices such as a wrist-wearable device 600 (or components thereof) and/or a smart textile-based garment 900 (FIGS. 9A-9C), as well as an HIPD 800. Having thus described example the head-wearable devices, attention will now be turned to example handheld intermediary processing devices, such as HIPD 800.

Example Handheld Intermediary Processing Devices

Figure 8A:
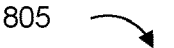
Figure 8A:
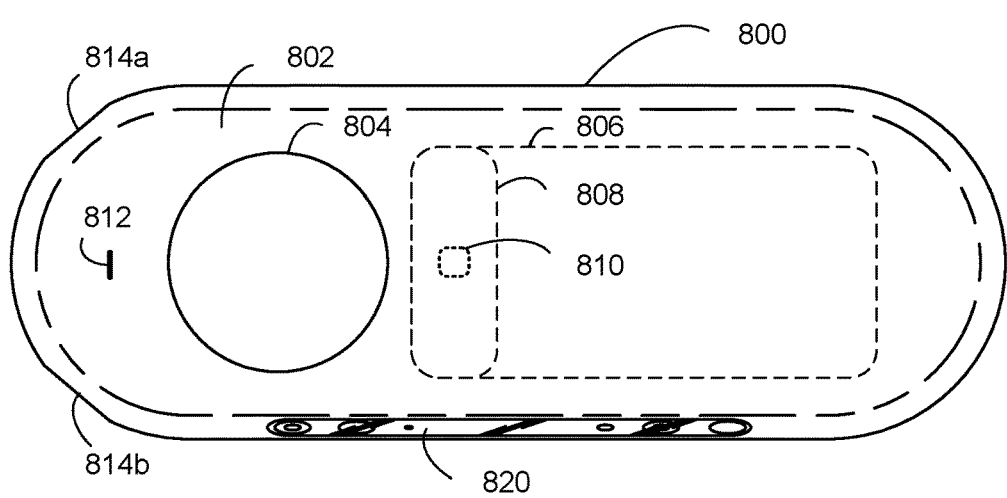
Figure 8A:
Figure 8A:
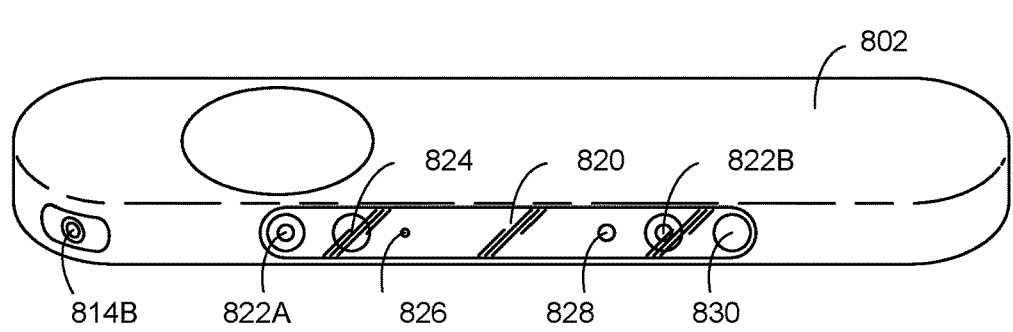

FIGS. 8A and 8B illustrate an example handheld intermediary processing device (HIPD) 800, in accordance with some embodiments. The HIPD 800 can perform various functions and/or operations associated with navigating through user interfaces and selectively opening applications, as well as the functions and/or operations described above with reference to FIGS. 1A to 4C.

FIG. 8A shows a top view 805 and a side view 825 of the HIPD 800. The HIPD 800 is configured to communicatively couple with one or more wearable devices (or other electronic devices) associated with a user. For example, the HIPD 800 is configured to communicatively couple with a user's wrist-wearable device 600 (or components thereof, such as the watch body 620 and the wearable band 610), AR device 700, and/or VR device 710. The HIPD 800 can be configured to be held by a user (e.g., as a handheld controller), carried on the user's person (e.g., in their pocket or in their bag), placed in proximity of the user (e.g., placed on their desk while seated at their desk or on a charging dock), and/or placed at or within a predetermined distance from a wearable device or other electronic device (e.g., where, in some embodiments, the predetermined distance is the maximum distance (e.g., 10 meters) at which the HIPD 800 can successfully be communicatively coupled with an electronic device, such as a wearable device).

The HIPD 800 can perform various functions independently and/or in conjunction with one or more wearable devices (e.g., wrist-wearable device 600, AR device 700, and/or VR device 710). The HIPD 800 is configured to increase and/or improve the functionality of communicatively coupled devices, such as the wearable devices. The HIPD 800 is configured to perform one or more functions or operations associated with interacting with user interfaces and applications of communicatively coupled devices, interacting with an AR environment, interacting with a VR environment, and/or operating as a human-machine interface controller. Additionally, as will be described in more detail below, functionality and/or operations of the HIPD 800 can include, without limitation, task offloading and/or handoffs, thermals offloading and/or handoffs, 6 degrees of freedom (6DoF) raycasting and/or gaming (e.g., using imaging devices or cameras 814A and 814B, which can be used for simultaneous localization and mapping (SLAM), and/or with other image processing techniques), portable charging; messaging, image capturing via one or more imaging devices or cameras (e.g., cameras 822A and 822B), sensing user input (e.g., sensing a touch on a multi-touch input surface 802), wireless communications and/or interlining (e.g., cellular, near field, Wi-Fi, or personal area network), location determination, financial transactions, providing haptic feedback, alarms, notifications, biometric authentication, health monitoring, sleep monitoring. The above-example functions can be executed independently in the HIPD 800 and/or in communication between the HIPD 800 and another wearable device described herein. In some embodiments, functions can be executed on the HIPD 800 in conjunction with an AR environment. As the skilled artisan will appreciate upon reading the descriptions provided herein, the HIPD 800 described herein can be used with any type of suitable AR environment.

While the HIPD 800 is communicatively coupled with a wearable device and/or other electronic device, the HIPD 800 is configured to perform one or more operations initiated at the wearable device and/or the other electronic device. In particular, one or more operations of the wearable device and/or the other electronic device can be offloaded to the HIPD 800 to be performed. The HIPD 800 performs one or more operations of the wearable device and/or the other electronic device and provides data corresponding to the completed operations to the wearable device and/or the other electronic device. For example, a user can initiate a video stream using the AR device 700 and back-end tasks associated with performing the video stream (e.g., video rendering) can be offloaded to the HIPD 800, which the HIPD 800 performs and provides corresponding data to the AR device 700 to perform remaining front-end tasks associated with the video stream (e.g., presenting the rendered video data via a display of the AR device 700). In this way, the HIPD 800, which has more computational resources and greater thermal headroom than a wearable device can perform computationally intensive tasks for the wearable device, improving performance of an operation performed by the wearable device.

The HIPD 800 includes a multi-touch input surface 802 on a first side (e.g., a front surface) that is configured to detect one or more user inputs. In particular, the multi-touch input surface 802 can detect single-tap inputs, multi-tap inputs, swipe gestures and/or inputs, force-based and/or pressure-based touch inputs, held taps, and the like. The multi-touch input surface 802 is configured to detect capacitive touch inputs and/or force (and/or pressure) touch inputs. The multi-touch input surface 802 includes a first touch-input surface 804 defined by a surface depression, and a second touch-input surface 806 defined by a substantially planar portion. The first touch-input surface 804 can be disposed adjacent to the second touch-input surface 806. In some embodiments, the first touch-input surface 804 and the second touch-input surface 806 can be different dimensions, shapes, and/or cover different portions of the multi-touch input surface 802. For example, the first touch-input surface 804 can be substantially circular and the second touch-input surface 806 is substantially rectangular. In some embodiments, the surface depression of the multi-touch input surface 802 is configured to guide user handling of the HIPD 800. In particular, the surface depression is configured such that the user holds the HIPD 800 upright when held in a single hand (e.g., such that the using imaging devices or cameras 814A and 814B are pointed toward a ceiling or the sky). Additionally, the surface depression is configured such that the user's thumb rests within the first touch-input surface 804.

In some embodiments, the different touch-input surfaces include a plurality of touch-input zones. For example, the second touch-input surface 806 includes at least a first touch-input zone 808 within a second touch-input zone 806 and a third touch-input zone 810 within the first touch-input zone 808. In some embodiments, one or more of the touch-input zones are optional and/or user defined (e.g., a user can specific a touch-input zone based on their preferences). In some embodiments, each touch-input surface and/or touch-input zone is associated with a predetermined set of commands. For example, a user input detected within the first touch-input zone 808 causes the HIPD 800 to perform a first command and a user input detected within the second touch-input zone 806 causes the HIPD 800 to perform a second command, distinct from the first. In some embodiments, different touch-input surfaces and/or touch-input zones are configured to detect one or more types of user inputs. The different touch-input surfaces and/or touch-input zones can be configured to detect the same or distinct types of user inputs. For example, the first touch-input zone 808 can be configured to detect force touch inputs (e.g., a magnitude at which the user presses down) and capacitive touch inputs, and the second touch-input zone 806 can be configured to detect capacitive touch inputs.

The HIPD 800 includes one or more sensors 851 for sensing data used in the performance of one or more operations and/or functions. For example, the HIPD 800 can include an IMU that is used in conjunction with cameras 814 for 3-dimensional object manipulation (e.g., enlarging, moving, destroying, etc. an object) in an AR or VR environment. Non-limiting examples of the sensors 851 included in the HIPD 800 include a light sensor, a magnetometer, a depth sensor, a pressure sensor, and a force sensor. Additional examples of the sensors 851 are provided below in reference to FIG. 8B.

The HIPD 800 can include one or more light indicators 812 to provide one or more notifications to the user. In some embodiments, the light indicators are LEDs or other types of illumination devices. The light indicators 812 can operate as a privacy light to notify the user and/or others near the user that an imaging device and/or microphone are active. In some embodiments, a light indicator is positioned adjacent to one or more touch-input surfaces. For example, a light indicator can be positioned around the first touch-input surface 804. The light indicators can be illuminated in different colors and/or patterns to provide the user with one or more notifications and/or information about the device. For example, a light indicator positioned around the first touch-input surface 804 can flash when the user receives a notification (e.g., a message), change red when the HIPD 800 is out of power, operate as a progress bar (e.g., a light ring that is closed when a task is completed (e.g., 0% to 100%)), operates as a volume indicator, etc.).

In some embodiments, the HIPD 800 includes one or more additional sensors on another surface. For example, as shown FIG. 8A, HIPD 800 includes a set of one or more sensors (e.g., sensor set 820) on an edge of the HIPD 800. The sensor set 820, when positioned on an edge of the of the HIPD 800, can be pe positioned at a predetermined tilt angle (e.g., 26 degrees), which allows the sensor set 820 to be angled toward the user when placed on a desk or other flat surface. Alternatively, in some embodiments, the sensor set 820 is positioned on a surface opposite the multi-touch input surface 802 (e.g., a back surface). The one or more sensors of the sensor set 820 are discussed in detail below.

The side view 825 of the of the HIPD 800 shows the sensor set 820 and camera 814B. The sensor set 820 includes one or more cameras 822A and 822B, a depth projector 824, an ambient light sensor 828, and a depth receiver 830. In some embodiments, the sensor set 820 includes a light indicator 826. The light indicator 826 can operate as a privacy indicator to let the user and/or those around them know that a camera and/or microphone is active. The sensor set 820 is configured to capture a user's facial expression such that the user can puppet a custom avatar (e.g., showing emotions, such as smiles, laughter, etc., on the avatar or a digital representation of the user). The sensor set 820 can be configured as a side stereo red-green-blue (RGB) system, a rear indirect time-of-flight (iToF) system, or a rear stereo RGB system. As the skilled artisan will appreciate upon reading the descriptions provided herein, the HIPD 800 described herein can use different sensor set 820 configurations and/or sensor set 820 placement.

In some embodiments, the HIPD 800 includes one or more haptic devices 871 (FIG. 8B; e.g., a vibratory haptic actuator) that are configured to provide haptic feedback (e.g., kinesthetic sensation). The sensors 851, and/or the haptic devices 871 can be configured to operate in conjunction with multiple applications and/or communicatively coupled devices including, without limitation, a wearable devices, health monitoring applications, social media applications, game applications, and artificial reality applications (e.g., the applications associated with artificial reality).

The HIPD 800 is configured to operate without a display. However, in optional embodiments, the HIPD 800 can include a display 868 (FIG. 8B). The HIPD 800 can also income one or more optional peripheral buttons 867 (FIG. 8B). For example, the peripheral buttons 867 can be used to turn on or turn off the HIPD 800. Further, the HIPD 800 housing can be formed of polymers and/or elastomer elastomers. The HIPD 800 can be configured to have a non-slip surface to allow the HIPD 800 to be placed on a surface without requiring a user to watch over the HIPD 800. In other words, the HIPD 800 is designed such that it would not easily slide off a surfaces. In some embodiments, the HIPD 800 include one or magnets to couple the HIPD 800 to another surface. This allows the user to mount the HIPD 800 to different surfaces and provide the user with greater flexibility in use of the HIPD 800.

As described above, the HIPD 800 can distribute and/or provide instructions for performing the one or more tasks at the HIPD 800 and/or a communicatively coupled device. For example, the HIPD 800 can identify one or more back-end tasks to be performed by the HIPD 800 and one or more front-end tasks to be performed by a communicatively coupled device. While the HIPD 800 is configured to offload and/or handoff tasks of a communicatively coupled device, the HIPD 800 can perform both back-end and front-end tasks (e.g., via one or more processors, such as CPU 877; FIG. 8B). The HIPD 800 can, without limitation, can be used to perform augmenting calling (e.g., receiving and/or sending 3D or 2.5D live volumetric calls, live digital human representation calls, and/or avatar calls), discreet messaging, 6DoF portrait/landscape gaming, AR/VR object manipulation, AR/VR content display (e.g., presenting content via a virtual display), and/or other AR/VR interactions. The HIPD 800 can perform the above operations alone or in conjunction with a wearable device (or other communicatively coupled electronic device).

FIG. 8B shows block diagrams of a computing system 840 of the HIPD 800 (described herein as an HIPD computing system), in accordance with some embodiments. The HIPD 800, described in detail above, can include one or more components shown in HIPD computing system 840. The HIPD 800 will be understood to include the components shown and described below for the HIPD computing system 840. In some embodiments, all, or a substantial portion of the components of the HIPD computing system 840 are included in a single integrated circuit. Alternatively, in some embodiments, components of the HIPD computing system 840 are included in a plurality of integrated circuits that are communicatively coupled.

The HIPD computing system 840 can include a processor (e.g., a CPU 877, a GPU, and/or a CPU with integrated graphics), a controller 875, a peripherals interface 850 that includes one or more sensors 851 and other peripheral devices, a power source (e.g., a power system 895), and memory (e.g., a memory 878) that includes an operating system (e.g., an operating system 879), data (e.g., data 888), one or more applications (e.g., applications 880), and one or more modules (e.g., a communications interface module 881, a graphics module 882, a task and processing management module 883, an interoperability module 884, an AR processing module 885, a data management module 886, etc.). The HIPD computing system 840 further includes a power system 895 that includes a charger input and output 896, a PMIC 897, and a battery 898, all of which are defined above.

In some embodiments, the peripherals interface 850 can include one or more sensors 851. The sensors 851 can include analogous sensors to those described above in reference to FIG. 6B. For example, the sensors 851 can include imaging sensors 854, (optional) EMG sensors 856, IMUs 858, and capacitive sensors 860. In some embodiments, the sensors 851 can include one or more pressure sensor 852 for sensing pressure data, an altimeter 853 for sensing an altitude of the HIPD 800, a magnetometer 855 for sensing a magnetic field, a depth sensor 857 (or a time-of flight sensor) for determining a difference between the camera and the subject of an image, a position sensor 859 (e.g., a flexible position sensor) for sensing a relative displacement or position change of a portion of the HIPD 800, a force sensor 861 for sensing a force applied to a portion of the HIPD 800, and a light sensor 862 (e.g., an ambient light sensor) for detecting an amount of lighting. The sensors 851 can include one or more sensors not shown in FIG. 8B.

Analogous to the peripherals described above in reference to FIGS. 6B, the peripherals interface 850 can also include an NFC component 863, a GPS component 864, an LTE component 865, a Wi-Fi and/or Bluetooth communication component 866, a speaker 869, a haptic device 871, and a microphone 873. As described above in reference to FIG. 8A, the HIPD 800 can optionally include a display 868 and/or one or more buttons 867. The peripherals interface 850 can further include one or more cameras 870, touch surfaces 872, and/or one or more light emitters 874. The multi-touch input surface 802 described above in reference to FIG. 8A is an example of touch surface 872. The light emitters 874 can be one or more LEDs, lasers, etc. and can be used to project or present information to a user. For example, the light emitters 874 can include light indicators 812 and 826 described above in reference to FIG. 8A. The cameras 870 (e.g., cameras 814A, 814B, and 822 described above in FIG. 8A) can include one or more wide angle cameras, fish-eye cameras, spherical cameras, compound eye cameras (e.g., stereo and multi cameras), depth cameras, RGB cameras, ToF cameras, RGB-D cameras (depth and ToF cameras), and/or other available cameras. Cameras 870 can be used for SLAM; 6 DoF ray casting, gaming, object manipulation, and/or other rendering; facial recognition and facial expression recognition, etc.

Similar to the watch body computing system 660 and the watch band computing system 630 described above in reference to FIG. 6B, the HIPD computing system 840 can include one or more haptic controllers 876 and associated componentry (e.g., haptic devices 871) for providing haptic events at the HIPD 800.

Memory 878 can include high-speed random-access memory and/or non-volatile memory, such as one or more magnetic disk storage devices, flash memory devices, or other non-volatile solid-state memory devices. Access to the memory 878 by other components of the HIPD 800, such as the one or more processors and the peripherals interface 850, can be controlled by a memory controller of the controllers 875.

In some embodiments, software components stored in the memory 878 include one or more operating systems 879, one or more applications 880, one or more communication interface modules 881, one or more graphics modules 882, one or more data management modules 885, which are analogous to the software components described above in reference to FIG. 6B.

In some embodiments, software components stored in the memory 878 include a task and processing management module 883 for identifying one or more front-end and back-end tasks associated with an operation performed by the user, performing one or more front-end and/or back-end tasks, and/or providing instructions to one or more communicatively coupled devices that cause performance of the one or more front-end and/or back-end tasks. In some embodiments, the task and processing management module 883 uses data 888 (e.g., device data 890) to distribute the one or more front-end and/or back-end tasks based on communicatively coupled devices' computing resources, available power, thermal headroom, ongoing operations, and/or other factors. For example, the task and processing management module 883 can cause the performance of one or more back-end tasks (of an operation performed at communicatively coupled AR device 700) at the HIPD 800 in accordance with a determination that the operation is utilizing a predetermined amount (e.g., at least 70%) of computing resources available at the AR device 700.

In some embodiments, software components stored in the memory 878 include an interoperability module 884 for exchanging and utilizing information received and/or provided to distinct communicatively coupled devices. The interoperability module 884 allows for different systems, devices, and/or applications to connect and communicate in a coordinated way without user input. In some embodiments, software components stored in the memory 878 include an AR module 885 that is configured to process signals based at least on sensor data for use in an AR and/or VR environment. For example, the AR processing module 885 can be used for 3D object manipulation, gesture recognition, facial and facial expression, recognition, etc.

The memory 878 can also include data 888, including structured data. In some embodiments, the data 888 can include profile data 889, device data 890 (including device data of one or more devices communicatively coupled with the HIPD 800, such as device type, hardware, software, configurations, etc.), sensor data 891, media content data 892, and application data 893.

It should be appreciated that the HIPD computing system 840 is an example of a computing system within the HIPD 800, and that the HIPD 800 can have more or fewer components than shown in the HIPD computing system 840, combine two or more components, and/or have a different configuration and/or arrangement of the components. The various components shown in HIPD computing system 840 are implemented in hardware, software, firmware, or a combination thereof, including one or more signal processing and/or application-specific integrated circuits.

Figure 9B:
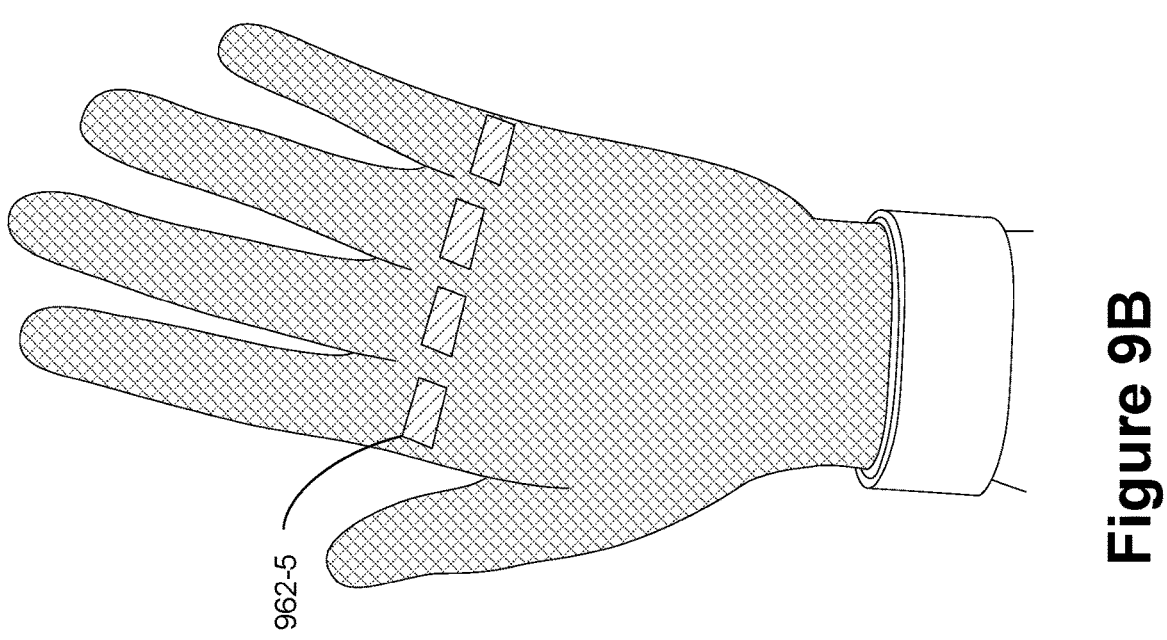
FIGS. 9A-9C illustrate an example smart textile-based garment in accordance with some embodiments.
Figure 9A:
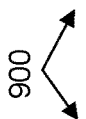
Figure 9A:
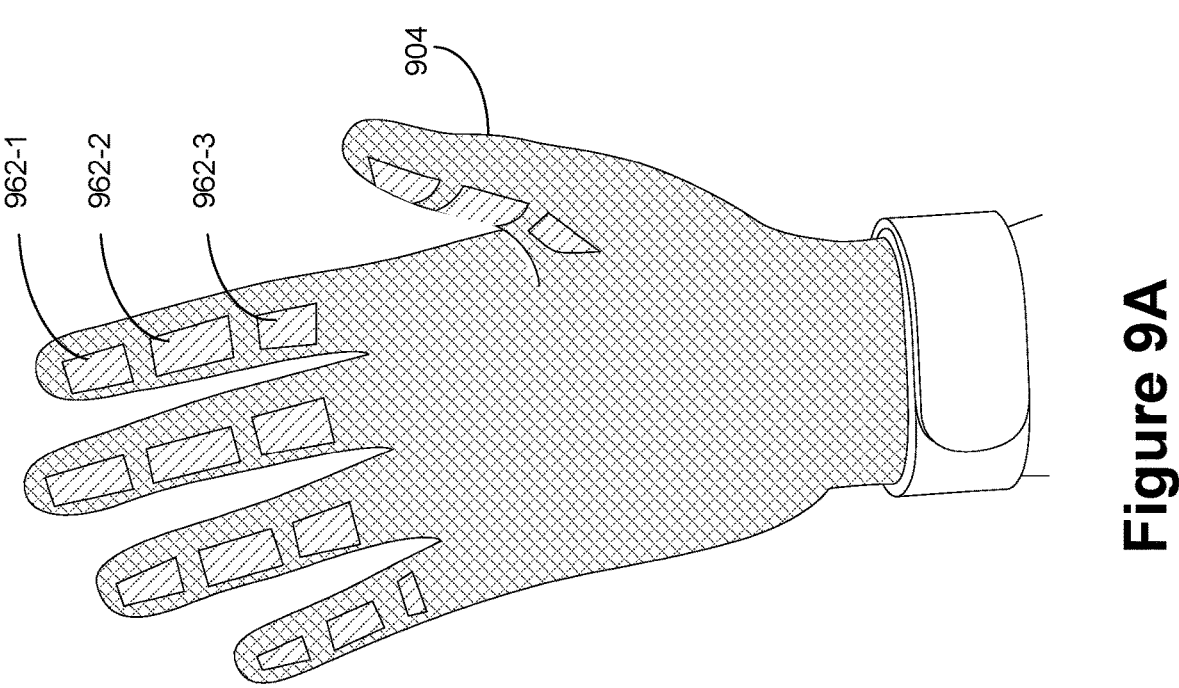
Figure 9C:
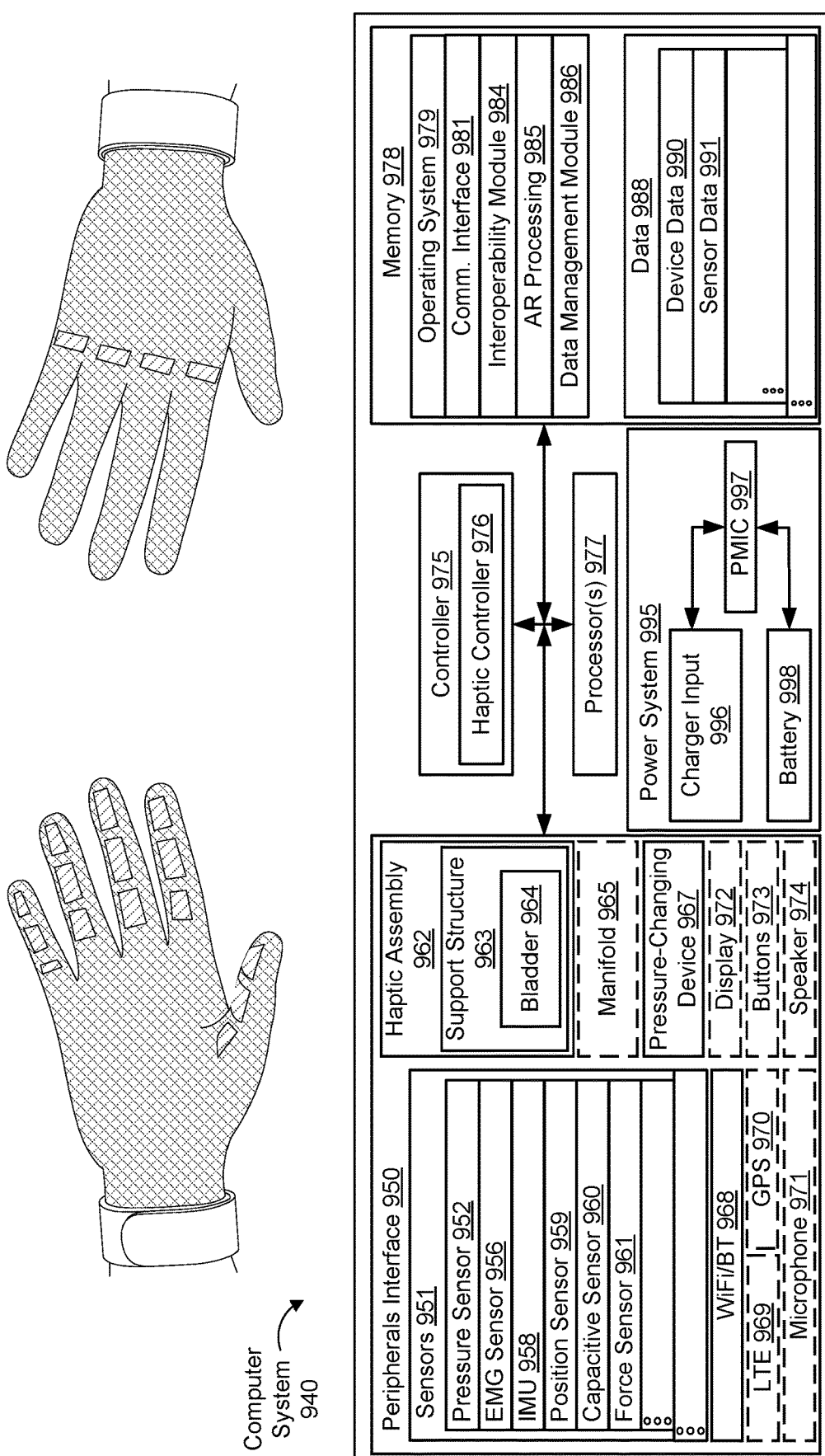

The techniques described above in FIG. 8A-8B can be used with any device used as a human-machine interface controller. In some embodiments, an HIPD 800 can be used in conjunction with one or more wearable device such as a head-wearable device (e.g., AR device 700 and VR device 710) and/or a wrist-wearable device 600 (or components thereof). In some embodiments, an HIPD 800 can also be used in conjunction with a wearable garment, such as smart textile-based garment 900 (FIGS. 9A-9C). Having thus described the HIPD 800, attention will now be turned to example feedback devices, such as smart textile-based garment 900.

Example Smart Textile-Based Garments

FIGS. 9A and 9B illustrate an example smart textile-based garment, in accordance with some embodiments. The smart textile-based garment 900 (e.g., wearable gloves, a shirt, a headband, a wristbands, socks, etc.) is configured to communicatively couple with one or more electronic devices, such as a wrist-wearable device 600, a head-wearable device, an HIPD 800, a laptop, tablet, and/or other computing devices. The smart textile-based garment 900 can perform various functions and/or operations associated with navigating through user interfaces and selectively opening applications, as well as the functions and/or operations described above with reference to FIGS. 2A to 2C.

The smart textile-based garment 900 can be part of an AR system, such as AR system 500d described above in reference to FIGS. 5D-1 and 5D-2. The smart textile-based garment 900 is also configured to provide feedback (e.g., tactile or other haptic feedback) to a user based on the user's interactions with a computing system (e.g., navigation of a user interface, operation of an application (e.g., game vibrations, media responsive haptics), device notifications, etc.)), and/or the user's interactions within an AR environment. In some embodiments, the smart textile-based garment 900 receives instructions from a communicatively coupled device (e.g., the wrist-wearable device 600, a head-wearable device, and HIPD 800, etc.) for causing the performance of a feedback response. Alternatively, or in addition, in some embodiments, the smart textile-based garment 900 determines one or more feedback responses to provide a user. The smart textile-based garment 900 can determine the one or more feedback responses based on sensor data captured by one or more of its sensors (e.g., sensors 951; FIG. 9C) or communicatively coupled sensors (e.g., sensors of a wrist-wearable device 600, a head-wearable device, an HIPD 800, and/or other computing device).

Non-limiting examples of the feedback determined by the smart textile-based garment 900 and/or a communicatively coupled device include visual feedback, audio feedback, haptic (e.g., tactile, kinesthetic, etc.) feedback, thermal or temperature feedback, and/or other sensory perceptible feedback. The smart textile-based garment 900 can include respective feedback devices (e.g., a haptic device or assembly 962 or other feedback devices or assemblies) to provide the feedback responses to the user. Similarly, the smart textile-based garment 900 can communicatively couple with another device (and/or the other device's feedback devices) to coordinate the feedback provided to the user. For example, a VR device 710 can present an AR environment to a user and as the user interacts with objects within the AR environment, such as a virtual cup, the smart textile-based garment 900 provides respective response to the user. In particular, the smart textile-based garment 900 can provide haptic feedback to prevent (or, at a minimum, hinder/resist movement of) one or more of the user's fingers from bending past a certain point to simulate the sensation of touching a solid cup and/or thermal feedback to simulate the sensation of a cold or warm beverage.

Additionally or alternatively, in some embodiments, the smart textile-based garment 900 is configured to operate as a controller configured to perform one or more functions or operations associated with interacting with user interfaces and applications of communicatively coupled devices, interacting with an AR environment, interacting with VR environment, and/or operating as a human-machine interface controller, as well as functions and/or operations described above with reference to FIGS. 1A to 4C.

FIG. 9A shows one or more haptic assemblies 962 (e.g., first through fourth haptic assemblies 962-1 through 962-4) on a portion of the smart textile-based garment 900 adjacent to a palmar side of the user's hand and FIG. 9B shows additional haptic assemblies (e.g., a fifth haptic assembly 962-5) on a portion of the smart textile-based garment 900 adjacent to a dorsal side of the user's hand. In some embodiments, the haptic assemblies 962 include a mechanism that, at a minimum, provide resistance when a respective haptic assembly 962 is transitioned from a first state (e.g., a first pressurized state (e.g., at atmospheric pressure or deflated)) to a second state (e.g., a second pressurized state (e.g., inflated to a threshold pressure)). In other words, the haptic assemblies 962 described can transition between a first pressurized state and a second pressurized state to provide haptic feedback to the user. Structures of haptic assemblies 962 can be integrated into various devices configured to be in contact or proximity to a user's skin, including, but not limited to devices such as glove worn devices, body worn clothing device, headset devices. Each of the haptic assemblies 962 can be included in or physically coupled to a garment component 904 of the smart textile-based garment 900. For example, each of the haptic assemblies 962-1, 962-2, 962-3, . . . 962-N are physically coupled to the garment 904 are configured to contact respective phalanges of a user's thumb and fingers.

Due to the ever-changing nature of artificial-reality, the haptic assemblies 962 may be required to transition between the multiple states hundreds, or perhaps thousands of times, during a single use. Thus, the haptic assemblies 962 described herein are durable and designed to quickly transition from state to state. To provide some context, in a first pressurized state, the haptic assemblies 962 do not impede free movement of a portion of the wearer's body. For example, one or more haptic assemblies 962 incorporated into a glove are made from flexible materials that do not impede free movement of the wearer's hand and fingers (e.g., an electrostatic-zipping actuator). The haptic assemblies 962 are configured to conform to a shape of the portion of the wearer's body when in the first pressurized state. However, once in a second pressurized state, the haptic assemblies 962 can be configured to restrict and/or impede free movement of the portion of the wearer's body (e.g., appendages of the user's hand). For example, the respective haptic assembly 962 (or multiple respective haptic assemblies) can restrict movement of a wearer's finger (e.g., prevent the finger from curling or extending) when the haptic assembly 962 is in the second pressurized state. Moreover, once in the second pressurized state, the haptic assemblies 962 may take different shapes, with some haptic assemblies 962 configured to take a planar, rigid shape (e.g., flat and rigid), while some other haptic assemblies 962 are configured to curve or bend, at least partially.

The smart textile-based garment 900 can be one of a plurality of devices in an AR system (e.g., AR systems of FIGS. 5A-5D-2). For example, a user can wear a pair of gloves (e.g., a first type of smart textile-based garment 900), wear a haptics component of a wrist-wearable device 600 (FIGS. 6A-6B), wear a headband (e.g., a second type of smart textile-based garment 900), hold an HIPD 800, etc. As explained above, the haptic assemblies 962 are configured to provide haptic simulations to a wearer of the smart textile-based garments 900. The garment 904 of each smart textile-based garment 900 can be one of various articles of clothing (e.g., gloves, socks, shirts, pants, etc.). Thus, a user may wear multiple smart textile-based garments 900 that are each configured to provide haptic stimulations to respective parts of the body where the smart textile-based garments 900 are being worn. Although the smart textile-based garment 900 are described as an individual device, in some embodiments, the smart textile-based garment 900 can be combined with other wearable devices described herein. For example, the smart textile-based garment 900 can form part of a VR device 710 (e.g., a headband portion).

FIG. 9C shows block diagrams of a computing system 940 of the haptic assemblies 962, in accordance with some embodiments. The computing system 940 can include one or more peripheral interfaces 950, one or more power systems 995 (including charger input 996, PMIC 997, and battery 998), one or more controllers 975 (including one or more haptic controllers 976), one or more processors 977 (as defined above, including any of the examples provided), and memory 978, which can all be in electronic communication with each other. For example, the one or more processors 977 can be configured to execute instructions stored in the memory 978, which can cause a controller of the one or more controllers 975 to cause operations to be performed at one or more peripheral devices of the peripherals interface 950. In some embodiments, each operation described can occur based on electrical power provided by the power system 995.

In some embodiments, the peripherals interface 950 can include one or more devices configured to be part of the computing system 940, many of which have been defined above and/or described with respect to wrist-wearable devices shown in FIGS. 6A-8B. For example, the peripherals interface 950 can include one or more sensors 951, such as one or more pressure sensors 952, one or more EMG sensors 956, one or more IMUs 958, one or more position sensors 959, one or more capacitive sensors 960, one or more force sensors 961; and/or any other types of sensors defined above or described with respect to any other embodiments discussed herein. In some embodiments, the peripherals interface can include one or more additional peripheral devices, including one or more Wi-Fi and/or Bluetooth devices 968, an LTE component 969, a GPS component 970, a microphone 971, one or more haptic assemblies 962, one or more support structures 963 which can include one or more bladders 964, one or more manifolds 965, one or more pressure-changing devices 967, one or more displays 972, one or more buttons 973, one or more speakers 974, and/or any other types of peripheral devices defined above or described with respect to any other embodiments discussed herein. In some embodiments, computing system 940 includes more or fewer components than those shown in FIG. 9C.

In some embodiments, each haptic assembly 962 includes a support structure 963 and at least one bladder 964. The bladder 964 (e.g., a membrane) is a sealed, inflatable pocket made from a durable and puncture-resistant material, such as thermoplastic polyurethane (TPU), a flexible polymer, or the like. The bladder 964 contains a medium (e.g., a fluid such as air, inert gas, or even a liquid) that can be added to or removed from the bladder 964 to change pressure (e.g., fluid pressure) inside the bladder 964. The support structure 963 is made from a material that is stronger and stiffer than the material of the bladder 964. A respective support structure 963 coupled to a respective bladder 964 is configured to reinforce the respective bladder 964 as the respective bladder changes shape and size due to changes in pressure (e.g., fluid pressure) inside the bladder. The above example haptic assembly 962 is non-limiting. The haptic assembly 962 can include eccentric rotating mass (ERM), linear resonant actuators (LRA), voice coil motor (VCM), piezo haptic actuator, thermoelectric devices, solenoid actuators, ultrasonic transducers, thermo-resistive heaters, Peltier devices, and/or other devices configured to generate a perceptible response.

The smart textile-based garment 900 also includes a haptic controller 976 and a pressure-changing device 967. Alternatively, in some embodiments, the computing system 940 is communicatively coupled with a haptic controller 976 and/or pressure-changing device 967 (e.g., in electronic communication with one or more processors 977 of the computing system 940). The haptic controller 976 is configured to control operation of the pressure-changing device 967, and in turn operation of the smart textile-based garments 900. For example, the haptic controller 976 sends one or more signals to the pressure-changing device 967 to activate the pressure-changing device 967 (e.g., turn it on and off). The one or more signals can specify a desired pressure (e.g., pounds per square inch) to be output by the pressure-changing device 967. Generation of the one or more signals, and in turn the pressure output by the pressure-changing device 967, can be based on information collected by sensors 951 of the smart textile-based garment 900 and/or other communicatively coupled device. For example, the haptic controller 976 can provide one or more signals, based on collected sensor data, to cause the pressure-changing device 967 to increase the pressure (e.g., fluid pressure) inside a first haptic assembly 962 at a first time, and provide one or more additional signals, based on additional sensor data, to the pressure-changing device 967, to cause the pressure-changing device 967 to further increase the pressure inside a second haptic assembly 962 at a second time after the first time. Further, the haptic controller 976 can provide one or more signals to cause the pressure-changing device 967 to inflate one or more bladders 964 in a first portion of a smart textile-based garment 900 (e.g., a first finger), while one or more bladders 964 in a second portion of the smart textile-based garment 900 (e.g., a second finger) remain unchanged. Additionally, the haptic controller 976 can provide one or more signals to cause the pressure-changing device 967 to inflate one or more bladders 964 in a first smart textile-based garment 900 to a first pressure and inflate one or more other bladders 964 in the first smart textile-based garment 900 to a second pressure different from the first pressure. Depending on the number of smart textile-based garments 900 serviced by the pressure-changing device 967, and the number of bladders therein, many different inflation configurations can be achieved through the one or more signals, and the examples above are not meant to be limiting.

The smart textile-based garment 900 may include an optional manifold 965 between the pressure-changing device 967, the haptic assemblies 962, and/or other portions of the smart textile-based garment 900. The manifold 965 may include one or more valves (not shown) that pneumatically couple each of the haptic assemblies 962 with the pressure-changing device 967 via tubing. In some embodiments, the manifold 965 is in communication with the controller 975, and the controller 975 controls the one or more valves of the manifold 965 (e.g., the controller generates one or more control signals). The manifold 965 is configured to switchably couple the pressure-changing device 967 with one or more haptic assemblies 962 of the smart textile-based garment 900. In some embodiments, one or more smart textile-based garments 900 or other haptic devices can be coupled in a network of haptic devices, and the manifold 965 can distribute the fluid between the coupled smart textile-based garments 900.

In some embodiments, instead of using the manifold 965 to pneumatically couple the pressure-changing device 967 with the haptic assemblies 962, the smart textile-based garment 900 may include multiple pressure-changing devices 967, where each pressure-changing device 967 is pneumatically coupled directly with a single (or multiple) haptic assembly 962. In some embodiments, the pressure-changing device 967 and the optional manifold 965 can be configured as part of one or more of the smart textile-based garments 900 (not illustrated) while, in other embodiments, the pressure-changing device 967 and the optional manifold 965 can be configured as external to the smart textile-based garments 900. In some embodiments, a single pressure-changing device 967 can be shared by multiple smart textile-based garments 900 or other haptic devices. In some embodiments, the pressure-changing device 967 is a pneumatic device, hydraulic device, a pneudraulic device, or some other device capable of adding and removing a medium (e.g., fluid, liquid, or gas) from the one or more haptic assemblies 962.

The memory 978 includes instructions and data, some or all of which may be stored as non-transitory computer-readable storage media within the memory 978. For example, the memory 978 can include one or more operating systems 979, one or more communication interface applications 981, one or more interoperability modules 984, one or more AR processing applications 985, one or more data-management modules 986, and/or any other types of data defined above or described with respect to FIGS. 6A-8B.

The memory 978 also includes data 988, which can be used in conjunction with one or more of the applications discussed above. The data 988 can include device data 990, sensor data 991, and/or any other types of data defined above or described with respect to FIGS. 6A-8B.

The different components of the computing system 940 (and the smart textile-based garment 900) shown in FIGS. 9A-9C can be coupled via a wired connection (e.g., via busing). Alternatively, one or more of the devices shown in FIGS. 9A-9C may be wirelessly connected (e.g., via short-range communication signals).

Example Embodiments

Turning now to some example embodiments of the methods, devices, systems, and computer-readable storage media described earlier.

(A1) In one aspect, some embodiments include a method (e.g., the method 400) of monitoring heart rate of a user. In some embodiments, the method is performed at a wearable device (e.g., the head-wearable device 102 and/or the wrist-wearable device 202) having memory (e.g., memory 650 of the wearable band 610, and/or memory 750A of the computing system 720) and one or more processors (e.g., the processor(s) 649 of the wearable band 610, and/or the processor(s) 748A of the computing system 720). The method includes (i) capturing, via an inward-facing camera (e.g., the camera 104) of an artificial-reality headset (e.g., the head-wearable device 102), a plurality of images of a region of a face of the user, the region including an eye of the user (e.g., the eye 110), where (a) a first image of the plurality of images includes a first position of a pupil in the eye; and (b) a second image of the plurality of images includes a second position of the pupil in the eye, the second position different than the first position; and (ii) determining heart rate information (e.g., the heart rate information 118) based on the plurality of images. In some embodiments, the heart rate information is determined based on PPG measurements from the plurality of images. In some embodiments, the camera is configured to have a large enough field of view to capture user expressions (e.g., a large enough field of view to capture the user's eyes and surrounding facial tissue).

(A2) In some embodiments of A1, the method further includes (i) determining eye tracking information from the plurality of images, and (ii) updating a user interface (e.g., the user interface 204) in accordance with the eye-tracking information. In some embodiments, the camera 104 is used to track the user's eyes and the images from the camera 104 are used to determine PPG information and heart rate information.

(A3) In some embodiments of A2, updating the user interface in accordance with the eye-tracking information includes updating a point of focus in the user interface based on a gaze direction of the user. For example, the user interface 204 may be caused to move within the field of view of the user based on detecting that the user 101 has a different gaze direction than they did at a previous point. In some embodiments, updating the user interface includes changing a perspective and/or field of view in accordance with the user's eye movement. In some embodiments, updating the user interface includes selecting a user interface element in accordance with the user's eye movement.

(A4) In some embodiments of any of A1-A3, the method further includes illuminating the eye using an illumination source (e.g., the illumination source 106 and/or 108) of the artificial-reality headset. For example, the headset is a VR headset with limited external light (e.g., controlled light between the headset and the user). In some embodiments, the artificial-reality headset is configured to restrict ambient light from entering the space between the headset and the user's eyes.

(A5) In some embodiments of A4, the illumination source is configured to operate in at least one of an infrared or near-infrared band. In some embodiments, the illumination source is configured to emit red light, near-infrared light, and/or infrared light. In some embodiments, the camera is configured to capture red light, near-infrared light, and/or infrared light. For example, the camera 104 may be configured to sense infrared and/or near-infrared wavelengths.

(A6) In some embodiments of any of A1-A5, the method further includes presenting a user interface to the user, where the plurality of images is captured while the user is viewing the user interface (e.g., the user interface 312 and/or 354). In some embodiments, the plurality of images is captured while the user is navigating or otherwise interacting with the user interface.

(A7) In some embodiments of A6, the method further includes presenting the heart rate information to the user via the user interface (e.g., the heart rate graph 342). For example, the heart rate information is presented in accordance with the user completing an activity, viewing a particular user interface, and/or inputting a request. For example, the heart rate information is presented after the user has completed gameplay of a video game so as not to distract the user during the gameplay (and/or obscure the user's vision during the gameplay).

(A8) In some embodiments of A6 or A7, the user interface corresponds to an application executing at the artificial-reality headset. For example, the application is a virtual reality or augmented reality application. For example, the user interface is presented via a display of the head-wearable device 102. In some embodiments, the user interface is displayed on a display that is distinct from the artificial-reality headset. For example, the application may be a fitness application or a video game.

(A9) In some embodiments of any of A1-A8, the inward-facing camera is configured to operate in a near-infrared range. In some embodiments, the inward-facing camera (e.g., the camera 104) is configured to operate in the near-infrared range and a visible light range. In some embodiments, the inward-facing camera is configured to operate in a range from infrared to visible light. The infrared band can be beneficial, as blood has an increased opacity in the infrared band as compared to the visible band. Additionally, eye-tracking cameras benefit from operating in the infrared band, as an infrared (IR) illumination source for eye tracking will not interfere with the user's vision.

(A10) In some embodiments of any of A1-A9, the heart rate information is based on a change in dilation of the eye calculated based on the plurality of images. In some embodiments, the heart rate information is based on blood flow within the eye (e.g., the eye 110). In some embodiments, the heart rate information is based on blood volume levels within the eye.

(A11) In some embodiments of any of A1-A10, the heart rate information is based on a change in skin color of the user calculated based on the plurality of images. In some embodiments, the heart rate information is based on blood volume levels in tissue of the user.

(A12) In some embodiments of A11, the change in skin color of the user corresponds to blood flow in the face of the user (e.g., an amount of blush in the cheek). For example, in some embodiments the field of view of the camera 104 is configured to capture a portion of the facial expression of the user 101, including a portion of skin surrounding the eye 110 of the user 101.

(A13) In some embodiments of any of A1-A12, the method further includes obtaining secondary heart rate information (e.g., the PPG information 222) from a wrist-wearable device (e.g., the wrist-wearable device 202) worn by the user. In some embodiments, the wrist-wearable device includes one or more image sensors for determining PPG based on blood volume levels in the user's tissue. In some embodiments, the wrist-wearable device includes one or more non-image sensors for use in determining the heart rate information.

(A14) In some embodiments of A13, the method further includes (i) aggregating the heart rate information and the secondary heart rate information to obtain aggregated heart rate information and (ii) presenting the aggregated heart rate information to the user. In some embodiments, the heart rate information and the secondary heart rate information are combined to obtain a median and/or mean heart rate. In some embodiments, one of the heart rate information and the secondary heart rate information is selected based on quality of the heart rate information and/or the secondary heart rate information.

(A15) In some embodiments of A13 or A14, the method further includes (i) in accordance with the secondary heart rate information meeting one or more criteria, selecting the secondary heart rate information as selected heart rate information; (ii) in accordance with the secondary heart rate information not meeting one or more criteria, selecting the heart rate information as the selected heart rate information; and (iii) presenting the selected heart rate information to the user. For example, the one or more criteria are selected to evaluate a coupling between the wrist-wearable device and a wrist of the user. In some embodiments, the one or more criteria are based on an amount of movement of the wrist of the user (e.g., IMU-based movement detection). In some embodiments, the one or more criteria include one or more quality criteria (e.g., amount of noise). In some embodiments, the one or more criteria include one or more criteria regarding quality of images from a camera. For example, movement of the user (e.g., while engaging in a physical activity and/or playing a video game) can cause sensors of the wrist-wearable device move/decouple with respect to the user's body. Additionally, blood volume levels in a user's hand/wrist are generally significantly lower than blood volume levels in the user's face/eyes, and therefore it can be beneficial to obtain PPG information from the face/eyes.

(A16) In some embodiments of any of A13-A15, the method further includes (i) in accordance with the heart rate information meeting one or more criteria, selecting the heart rate information as selected heart rate information; (ii) in accordance with the heart rate information not meeting one or more criteria, selecting the secondary heart rate information as the selected heart rate information; and (iii) presenting the selected heart rate information to the user. For example, the one or more criteria are selected to evaluate an image quality of the plurality of images. In some embodiments, the one or more criteria include one or more quality criteria (e.g., amount of noise).

(A17) In some embodiments of any of A1-A16, the heart rate information includes information about a heart rate of the user over a period (e.g., from t0 to t2 in FIG. 3C). For example, the heart rate information includes a median and/or mean heart rate for the period. In some embodiments, the heart rate information is presented to the user (e.g., including presenting a graph, an average, a maximum, and/or a minimum).

(B1) In another aspect, some embodiments include a method of monitoring a heart rate of a user. In some embodiments, the method is performed at a wearable device (e.g., the head-wearable device 102 and/or the wrist-wearable device 202) having memory (e.g., memory 650 of the wearable band 610, and/or memory 750A of the computing system 720) and one or more processors (e.g., the processor(s) 649 of the wearable band 610, and/or the processor(s) 748A of the computing system 720). The method includes (i) capturing, via an inward-facing camera (e.g., the camera 104) of an artificial-reality headset (e.g., the head-wearable device 102), a plurality of images of a region of a face of the user, the region including an eye of the user (e.g., the eye 110), where (a) a first image of the plurality of images includes a first position of a pupil in the eye, and (b) a second image of the plurality of images includes a second position of the pupil in the eye, the second position different than the first position; (ii) determining whether the plurality of images meet one or more quality criteria (e.g., determining whether a portion of the eye is obstructed and/or out of focus in at least a subset of the images); (iii) in accordance with the plurality of images meeting the one or more quality criteria, determining heart rate information based the eye in the plurality of images; and (iv) in accordance with the plurality of images not meeting the one or more quality criteria, determining the heart rate information based on a change in skin color in the plurality of images. For example, if the eye is obscured or out of focus, PPG information is obtained from blood volume levels in facial tissue of the user. As another example, if the eye is in focus and unobscured in the images, PPG information is obtained from eye movement, blood flow, and/or blood volume levels in the eye. In some embodiments, multiple areas of the user's skin are identified from the plurality of images and PPG is performed on each area. In some embodiments, the area with the highest quality PPG (e.g., least noise) is selected for using to determine heart rate information. In some embodiments, an area of the user's skin is selected for PPG analysis in accordance with positioning of the headset and/or camera with respect to the user's face.

(B2) In some embodiments of B1, the one or more quality criteria include a criterion corresponding to a portion of the pupil shown in the plurality of images. For example, if a portion of the pupil is obscured or blurry in at least a subset of the images, then the eye is not used to determine the heart rate information, e.g., PPG information and/or heart rate information is obtained from facial tissue or other parts of the user's body.

(B3) In some embodiments of B1 or B2, the one or more quality criteria include a criterion corresponding to an illumination of the pupil shown in the plurality of images. For example, if at least a portion of the pupil is too dark or too bright to determine blood flow/volume information in at least a subset of the images, then the eye is not used to determine the heart rate information for the corresponding period. For example, as discussed with respect to FIG. 1C, in some cases the eye-based PPG information 114 is unavailable because the view of the eye 110 from the camera 104 is obstructed.

(B4) In some embodiments of any of B1-B3, the one or more quality criteria include a criterion corresponding to an illumination of skin of the user in the plurality of images. For example, if the skin is too dark or too bright to determine blood flow/volume information in at least a subset of the images, then the skin is not used to determine the heart rate information for the corresponding period.

(B5) In some embodiments of any of B1-B4, the one or more quality criteria include a criterion corresponding to an amount of skin of the user in the plurality of images. For example, if the amount of skin shown in the images is insufficient to determine blood flow/volume information, then the skin is not used to determine the heart rate information for the corresponding period.

(B6) In some embodiments of any of B1-B5, the one or more quality criteria include a criterion corresponding to a point of focus in the plurality of images. For example, if the user's facial tissue is in focus and the user's eye is not in focus (e.g., blurry) in some of the images, then the facial tissue may be used to determine the heart rate information for the corresponding period.

(B7) In some embodiments of any of B1-B6, the one or more quality criteria include a criterion corresponding to relative quality of the pupil shown in the plurality of images and skin of the user in the plurality of images. For example, the system (e.g., the headset) selects the eye for PPG measurements if the eye is in focus and unobscured in the images, and the system selects the skin for the PPG measurements if the eye is out of focus or obscured in the images.

(B8) In some embodiments of any of B1-B7, the method further includes (i) determining eye-tracking information from the plurality of images and (ii) updating a user interface in accordance with the eye-tracking information. In some embodiments, the camera 104 is used to track the user's eyes and the images from the camera 104 are used to determine PPG information and heart rate information.

(B9) In some embodiments of B8, updating the user interface in accordance with the eye-tracking information includes updating a point of focus in the user interface based on a gaze direction of the user. In some embodiments, updating the user interface includes changing a perspective and/or field of view in accordance with the user's eye movement. In some embodiments, updating the user interface includes selecting a user interface element in accordance with the user's eye movement. For example, the scene shown in the user interface 312 (e.g., the field of view) is updated in accordance with the user's gaze.

(B10) In some embodiments of any of B1-B9, the method further includes illuminating the eye using an illumination source (e.g., the illumination source 106 and/or 108) of the artificial-reality headset. For example, the headset is a virtual-reality headset designed to limit/prevent external light from entering the space between the headset and the user's eyes.

(B11) In some embodiments of B10, the illumination source is configured to operate in at least one of an infrared or near-infrared band. In some embodiments, the illumination source is configured to emit red light, near-infrared light, and/or infrared light. Infrared and/or near-infrared light is not visible by most users and thus does not interfere with the user's viewing experience.

(B12) In some embodiments of any of B1-B11, the method further includes presenting a user interface to the user, where the plurality of images is captured while the user is viewing the user interface.

(B13) In some embodiments of B12, the method further includes presenting the heart rate information to the user via the user interface (e.g., the user interface 204).

(B14) In some embodiments of B12 or B13, the user interface corresponds to an application executing at the artificial-reality headset (e.g., an application of applications 752 of the computing system 720).

(B15) In some embodiments of any of B1-B14, the inward-facing camera is configured to operate in a near-infrared range. In some embodiments, the inward-facing camera is configured to operate in the near-infrared range and a visible light range. In some embodiments, the inward-facing camera is configured to operate in a range from infrared to visible light.

(B16) In some embodiments of any of B1-B15, the method further includes obtaining secondary heart rate information from a wrist-wearable device worn by the user (e.g., the wrist-wearable device 600, and/or the wearable band 610. In some embodiments, primary PPG information (e.g., the PPG 220) is obtained from the headset, and secondary PPG information (e.g., the PPG 222) is obtained from the wrist-wearable device.

(B17) In some embodiments of B16, the method further includes (i) aggregating the heart rate information and the secondary heart rate information to obtain aggregated heart rate information, and (ii) presenting the aggregated heart rate information to the user. In some embodiments, aggregating the heart rate information and the secondary heart rate information includes selecting heart rate information for a first period using the heart rate information and selecting heart rate information for a second period using the secondary heart rate information.

(B18) In some embodiments of B16 or B17, the method further includes (i) in accordance with the secondary heart rate information meeting one or more criteria, selecting the secondary heart rate information as selected heart rate information; (ii) in accordance with the secondary heart rate information not meeting one or more criteria, selecting the heart rate information as the selected heart rate information; and (iii) presenting the selected heart rate information to the user.

(B19) In some embodiments of any of B16-B18, the method further includes (i) in accordance with the heart rate information meeting one or more criteria, selecting the heart rate information as selected heart rate information; (ii) in accordance with the heart rate information not meeting one or more criteria, selecting the secondary heart rate information as the selected heart rate information; and (iii) presenting the selected heart rate information to the user. In some embodiments, the heart rate information and the secondary heart rate information are each assessed for quality and the one with the higher assessed quality is becomes the selected heart rate information. For example, the heart rate measurements presented within the moments user interface 370 may correspond to the selected heart rate information, which may be the heart rate information or the secondary heart rate information.

(B20) In some embodiments of any of B1-19, the heart rate information includes information about a heart rate of the user over a period (e.g., the heart rate information from t0 to t2 shown in FIG. 2C).

In another aspect, some embodiments include a computing system including one or more processors and memory coupled to the one or more processors, the memory storing one or more programs configured to be executed by the one or more processors, and the one or more programs including instructions for performing any of the methods described herein (e.g., the methods 400, 450, A1-A17, or B1-20 above).

In yet another aspect, some embodiments include a non-transitory computer-readable storage medium storing one or more programs for execution by one or more processors of a computing system, the one or more programs including instructions for performing any of the methods described herein (e.g., the methods 400, 450, A1-A17, or B1-20 above).

Any data collection performed by the devices described herein and/or any devices configured to perform or cause the performance of the different embodiments described above in reference to any of the Figures, hereinafter the "devices," is done with user consent and in a manner that is consistent with all applicable privacy laws. Users are given options to allow the devices to collect data, as well as the option to limit or deny collection of data by the devices. A user is able to opt in or opt out of any data collection at any time. Further, users are given the option to request the removal of any collected data.

It will be understood that, although the terms "first," "second," etc., may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" can be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" can be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

What is claimed is:

1. A method of monitoring heart rate of a user, the method comprising:

illuminating, via an illumination source of an artificial-reality headset, an eye of the user;

capturing, via an inward-facing camera of the artificial-reality headset, a plurality of images of a region of a face of the user, the region including the eye of the user, wherein:

a first image of the plurality of images includes a first position of a pupil in the eye; and a second image of the plurality of images includes a second position of the pupil in the eye, the second position different than the first position;

determining heart rate information based on the plurality of images;

in accordance with a determination that the heart rate information meets one or more quality criteria, causing the heart rate information to be presented to the user, wherein the one or more quality criteria comprise at least one of:

the region of the face of the user being unobstructed; and the illumination of the pupil being within a predetermined range; and in accordance with a determination that the heart rate information does not meet the one or more quality criteria, forgoing causing the heart rate information to be presented to the user.

2. The method of claim 1, further comprising:

determining eye-tracking information from the plurality of images; and updating a user interface in accordance with the eye-tracking information.

3. The method of claim 2, wherein updating the user interface in accordance with the eye-tracking information includes updating a point of focus in the user interface based on a gaze direction of the user.

4. The method of claim 1, wherein the heart rate information is based on a change in dilation of the eye calculated based on the plurality of images.

5. The method of claim 1, wherein the heart rate information is based on a change in skin color of the user calculated based on the plurality of images.

6. The method of claim 1, further comprising obtaining secondary heart rate information from a wrist-wearable device worn by the user.

7. The method of claim 6, further comprising:

aggregating the heart rate information and the secondary heart rate information to obtain aggregated heart rate information; and presenting the aggregated heart rate information to the user.

8. The method of claim 6, further comprising:

in accordance with the determination that the heart rate information does not meet the one or more quality criteria and the secondary heart rate information meeting the one or more quality criteria, presenting the secondary heart rate information.

9. A system, comprising:

an artificial-reality headset including an inward-facing camera and an illumination source; and one or more processors that are in communication with the inward-facing camera, the one or more processors configured to perform operations for:

illuminating, via the illumination source of the artificial-reality headset, an eye of a user;

capturing, via the inward-facing camera of the artificial-reality headset, a plurality of images of a region of a face of the user, the region including the eye of the user, wherein:

a first image of the plurality of images includes a first position of a pupil in the eye; and a second image of the plurality of images includes a second position of the pupil in the eye, the second position different than the first position;

determining heart rate information based on the plurality of images;

in accordance with a determination that the heart rate information meets one or more quality criteria, causing the heart rate information to be presented to the user, wherein the one or more quality criteria comprise at least one of:

the region of the face of the user being unobstructed; and the illumination of the pupil being within a predetermined range; and in accordance with a determination that the heart rate information does not meet the one or more quality criteria, forgoing causing the heart rate information to be presented to the user.

10. The system of claim 9, wherein the one or more processors are further configured to perform operations for:

determining eye-tracking information from the plurality of images; and updating a user interface in accordance with the eye-tracking information.

11. The system of claim 10, wherein updating the user interface in accordance with the eye-tracking information includes updating a point of focus in the user interface based on a gaze direction of the user.

12. The system of claim 9, wherein the heart rate information is based on a change in dilation of the eye calculated based on the plurality of images.

13. The system of claim 9, wherein the heart rate information is based on a change in skin color of the user calculated based on the plurality of images.

14. The system of claim 9, the one or more processors further configured to perform the operations for:

obtaining secondary heart rate information from a wrist-wearable device worn by the user.

15. The system of claim 14, the one or more processors further configured to perform the operations for:

aggregating the heart rate information and the secondary heart rate information to obtain aggregated heart rate information; and presenting the aggregated heart rate information to the user.

16. The system of claim 14, the one or more processors further configured to perform the operations for:

in accordance with the determination that the heart rate information does not meet the one or more quality criteria and the secondary heart rate information meeting the one or more quality criteria, presenting the secondary heart rate information.

17. A non-transitory, computer-readable storage medium including instructions that, when executed by a system comprising one or more processors and memory, causes the system to perform operations for:

illuminating, via an illumination source of an artificial-reality headset, an eye of a user;

capturing, via an inward-facing camera of the artificial-reality headset, a plurality of images of a region of a face of the user, the region including the eye of the user, wherein:

a first image of the plurality of images includes a first position of a pupil in the eye; and a second image of the plurality of images includes a second position of the pupil in the eye, the second position different than the first position;

determining heart rate information based on the plurality of images;

in accordance with a determination that the heart rate information meets one or more quality criteria, causing the heart rate information to be presented to the user, wherein the one or more quality criteria comprise at least one of:

the region of the face of the user being unobstructed; and the illumination of the pupil being within a predetermined range; and in accordance with a determination that the heart rate information does not meet the one or more quality criteria, forgoing causing the heart rate information to be presented to the user.

18. The non-transitory, computer-readable storage medium of claim 17, wherein the heart rate information is based on a change in dilation of the eye calculated based on the plurality of images.

19. The non-transitory, computer-readable storage medium of claim 17, the processor further including instructions that, when executed by the system cause the system to perform operations for:

obtaining secondary heart rate information from a wrist-wearable device worn by the user.

20. The non-transitory, computer-readable storage medium of claim 19, the processor further including instructions that, when executed by the system cause the system to perform operations for:

in accordance with the determination that the heart rate information does not meet the one or more quality criteria and the secondary heart rate information meeting the one or more quality criteria, presenting the secondary heart rate information.

* * * * *